US007943636B2

(12) United States Patent
Hays et al.

(10) Patent No.: US 7,943,636 B2
(45) Date of Patent: May 17, 2011

(54) 1-SUBSTITUTED PYRAZOLO (3,4-C) RING COMPOUNDS AS MODULATORS OF CYTOKINE BIOSYNTHESIS FOR THE TREATMENT OF VIRAL INFECTIONS AND NEOPLASTIC DISEASES

(75) Inventors: David S. Hays, Woodbury, MN (US); Ryan B. Prince, St. Paul, MN (US); Chad A. Haraldson, Apple Valley, MN (US); Jason D. Bonk, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 467 days.

(21) Appl. No.: 11/887,492

(22) PCT Filed: Mar. 31, 2006

(86) PCT No.: PCT/US2006/012263
§ 371 (c)(1),
(2), (4) Date: Nov. 14, 2008

(87) PCT Pub. No.: WO2006/107851
PCT Pub. Date: Oct. 12, 2006

(65) Prior Publication Data
US 2009/0163533 A1 Jun. 25, 2009

Related U.S. Application Data

(60) Provisional application No. 60/667,869, filed on Apr. 1, 2005, provisional application No. 60/733,037, filed on Nov. 3, 2005.

(51) Int. Cl.
*A61K 31/4375* (2006.01)
*C07D 471/04* (2006.01)
*C07D 471/14* (2006.01)
*A61P 35/00* (2006.01)
*A61P 31/12* (2006.01)

(52) U.S. Cl. ........... 514/293; 514/303; 546/82; 546/119

(58) Field of Classification Search .................. 546/82, 546/119; 514/293, 303
See application file for complete search history.

(56) References Cited

U.S. PATENT DOCUMENTS

| | | | |
|---|---|---|---|
| 3,314,941 A | 4/1967 | Lundquist, Jr. et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster et al. |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster et al. |
| 5,268,376 A | 12/1993 | Gester |
| 5,274,113 A | 12/1993 | Kang et al. |
| 5,346,905 A | 9/1994 | Gerster |
| 5,352,680 A | 10/1994 | Portoghese et al. |

(Continued)

FOREIGN PATENT DOCUMENTS

AU 2004220534 A1 9/2004

(Continued)

OTHER PUBLICATIONS

Colotta et al., Journal of Medicinal Chemistry (2000), 43(16), 3118-3124 .* International Search Report and Written Opinion for PCT/US2006/012263 mailed Aug. 28, 2006.
International Preliminary Report on Patentability for PCT/US2006/012263 mailed Oct. 11, 2007.
[No. Author Listed] "Aqueous cream." Wikipedia. Available at http://en.wikipedia.org/wiki/Aqueous_cream. Last accessed Sep. 15, 2010.
[No. Author Listed] "Comparative Tests." Filed Apr. 8, 2005 during prosecution for EP 00938205.2, EP 00950215.4 and EP 00938211.0 in the name of 3M Innovative Properties Co.
[No. Author Listed] Chemical Abstracts. 1964;61(1):6060g.
[No. Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.

(Continued)

*Primary Examiner* — Janet L Andres
*Assistant Examiner* — Niloofar Rahmani
(74) *Attorney, Agent, or Firm* — Kathleen B. Gross

(57) ABSTRACT

Pyrazolo[3,4-c] ring compounds of Formula (I), e.g., pyrazolo[3,4-c]pyridines, pyrazolo[3,4-c]quinolines, 6,7,8,9-tetrahydro pyrazolo[3,4-c]quinolines, and pyrazolo[3,4-c]naphthyridines, substituted at the 1-position, pharmaceutical compositions containing the compounds, intermediates, methods of making and methods of use of these compounds as immunomodulators, for inducing cytokine biosynthesis in animals and in the treatment of diseases including viral and neoplastic diseases are disclosed.

22 Claims, No Drawings

U.S. PATENT DOCUMENTS

| | | |
|---|---|---|
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |

| Patent/Pub No. | Date | Inventor |
|---|---|---|
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0166384 A1 | 7/2007 | Zarraga |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |

| | | | |
|---|---|---|---|
| 2009/0105295 A1 | 4/2009 | Kshirsagar et al. | |
| 2009/0124611 A1 | 5/2009 | Hays et al. | |
| 2009/0163532 A1 | 6/2009 | Perman et al. | |
| 2009/0176821 A1 | 7/2009 | Kshirsagar et al. | |
| 2009/0240055 A1 | 9/2009 | Krepski et al. | |
| 2009/0253695 A1 | 10/2009 | Kshirsagar et al. | |
| 2009/0270443 A1 | 10/2009 | Stoermer et al. | |
| 2009/0318435 A1 | 12/2009 | Hays et al. | |
| 2010/0113565 A1 | 5/2010 | Gorden et al. | |
| 2010/0240693 A1 | 9/2010 | Lundquist, Jr. et al. | |

FOREIGN PATENT DOCUMENTS

| | | |
|---|---|---|
| AU | 2004229478 A1 | 10/2004 |
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 A1 | 10/1990 |
| EP | 0 425 306 A2 | 5/1991 |
| EP | 0 510 260 A2 | 10/1992 |
| EP | 0 556 008 A1 | 8/1993 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 | 6/2001 |
| EP | 1 145 340 A2 | 10/2001 |
| EP | 1 256 582 A1 | 11/2002 |
| EP | 1 341 791 B1 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 1180156 A | 7/1989 |
| JP | 4066571 A | 3/1992 |
| JP | 4327587 A | 11/1992 |
| JP | 5286973 A | 11/1993 |
| JP | 9208584 A | 8/1997 |
| JP | 11222432 A | 8/1999 |
| JP | 2000247884 A | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO 91/06682 A1 | 5/1991 |
| WO | WO 92/06093 A1 | 4/1992 |
| WO | WO 92/15581 A1 | 9/1992 |
| WO | WO 92/15582 A1 | 9/1992 |
| WO | WO 93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO 95/02598 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304-AI | 12/2000 |
| WO | WO-00/76505 A1 | 12/2000 |
| WO | WO-00/76518-AI | 12/2000 |
| WO | WO-00/76519 A1 | 12/2000 |
| WO | WO-01/34709 A1 | 5/2001 |
| WO | WO-01/51486 A1 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO-02/36592 A1 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A2 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944-AI | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/009593 A1 | 1/2004 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO 2004/058759 | 7/2004 |
| WO | WO-2004/071459 A2 | 8/2004 |
| WO | WO-2004/075865 A2 | 9/2004 |
| WO | WO 2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO-2005/016273 A2 | 2/2005 |
| WO | WO-2005/016275 A2 | 2/2005 |
| WO | WO-2005/018551 A2 | 3/2005 |
| WO | WO-2005/018555 A2 | 3/2005 |
| WO | WO-2005/018556 A2 | 3/2005 |
| WO | WO-2005/020999 A1 | 3/2005 |
| WO | WO-2005/023190 A2 | 3/2005 |
| WO | WO-2005/025614 A3 | 3/2005 |
| WO | WO-2005/029037 A2 | 3/2005 |
| WO | WO-2005/032484 A3 | 4/2005 |
| WO | WO-2005/041891 A2 | 5/2005 |
| WO | WO-2005/048933 A2 | 6/2005 |
| WO | WO-2005/048945 A2 | 6/2005 |
| WO | WO-2005/049076 A1 | 6/2005 |
| WO | WO-2005/051317 A2 | 6/2005 |
| WO | WO-2005/051324 A2 | 6/2005 |
| WO | WO-2005/054237 A1 | 6/2005 |
| WO | WO-2005/054238 A1 | 6/2005 |

| | | |
|---|---|---|
| WO | WO-2005/065678 A1 | 7/2005 |
| WO | WO-2005/066169 A2 | 7/2005 |
| WO | WO-2005/066170 A1 | 7/2005 |
| WO | WO-2005/066172 A1 | 7/2005 |
| WO | WO-2005/067500 A2 | 7/2005 |
| WO | WO-2005/076783 A2 | 8/2005 |
| WO | 2005079195 * | 9/2005 |
| WO | WO 2005/079195 | 9/2005 |
| WO | WO-2005/094531 A2 | 10/2005 |
| WO | WO-2005/110013 A2 | 11/2005 |
| WO | WO-2005/123079 A2 | 12/2005 |
| WO | WO-2005/123080 A2 | 12/2005 |
| WO | WO-2006/004737 A2 | 1/2006 |
| WO | WO-2006/009826 A1 | 1/2006 |
| WO | WO-2006/009832 A1 | 1/2006 |
| WO | WO-2006/026760 A2 | 3/2006 |
| WO | WO-2006/028451 A1 | 3/2006 |
| WO | WO 2006/028545 | 3/2006 |
| WO | WO-2006/028962 A2 | 3/2006 |
| WO | WO-2006/029115 A2 | 3/2006 |
| WO | WO-2006/031878 A2 | 3/2006 |
| WO | WO-2006/038923 A2 | 4/2006 |
| WO | WO-2006/063072 A2 | 6/2006 |
| WO | WO-2006/063152 A2 | 6/2006 |
| WO | WO-2006/065280 A2 | 6/2006 |
| WO | WO-2006/073940 A2 | 7/2006 |
| WO | WO-2006/074003 A2 | 7/2006 |
| WO | WO-2006/074045 A2 | 7/2006 |
| WO | WO-2006/083440 A2 | 8/2006 |
| WO | WO-2006/084251 A2 | 8/2006 |
| WO | WO-2006/086449 A2 | 8/2006 |
| WO | WO-2006/086633 A2 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO 2006/107753 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/002646 A2 | 1/2008 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov-Dec 1987;5(6):487-91.
Auwers, [Uber die Isomerie-Verhaltnisse in der Pyrazol-Reihe. Berichte. VI.] 1926;601-607. German.
Bachman et al., Synthesis of substituted quinolylamines. Derivatives of 4-amino-7- chloroquinoline. J Org Chem. 1950;15(6):1278-84.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with *Porphyromonas gingivalis* and induced alveolar bone loss in immunocompetent and severe combined immunodeficient mice. Arch Oral Biol. Dec. 1994; 39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Baranov et al., Imidazo[4-5c]quinolines. In Chemical Abstracts. 1976;85:637. Abstract 94362z.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (–)- Methadone from D-(–)- Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Berenyi et al., Ring transformation of condensed dihyrdo-astriazines. J Heterocyclic Chem. 1981;18:1537-40.
Bernstein et al., Daily or weekly therapy with resiquimod (R-848) reduces genital recurrences in herpes simplex virus-infected guinea pigs during and after treatment. J Infect Dis. Mar 15, 2001;183(6):844-9. Epub 2001 Feb 13.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. 1993 Oct;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response modifier R-848. J Immunol. Nov. 15, 2000;165(10):5552-7.
Bitterman-Deutsch et al., [Brown spider bite]. Harefuah. Sep. 1990;119(5-6):137-9. Hebrew.
Booth et al., Dapsone suppresses integrin-mediated neutrophil adherence function. J Invest Dermatol. Feb. 1992;98(2):135-40.
Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Brennan et al., Automated bioassay of interferons in microtest plates. Biotechniques. Jun./Jul. 1983(1):78-82.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chollet et al., Development of a topically active imiquimod formulation. Pharm Dev Technol. Jan. 4, 1999;4(1):35-43.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. 2004 Jan. 22;6(2):221-4.

Davis, Current therapy for chronic hepatitis C. Gastroenterology. Feb. 2000;118(2 Suppl 1):S104-14.

Davis et at., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et at., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3 + 2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Dorwald, "Preface." Side Reactions in Organic Synthesis. A Guide to Successful Synthesis Design. Wiley-VCH. 2005: IX.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al.BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.
Frantz et al., Toll4 (TLR4) expression in cardiac myocytes in normal and failing myocardium. J Clin Invest. Aug. 1999;104(3):271-80.
Fu et al., Regioselective Catalytic Hydrogenation of Polycyclic Aromatic Hydocarbons under Mild conditions. J Org Chem. 1980;45:2979-803.
Fuchsberger et al., Priming Interferon-a 1 or Interferon-a 2 Enhances the Production of Both Subtypes Simultaneously. J Interferon and Cytokine Res. 1995;15:637-39.
Galose, Dapsone (diaminodiphenylsulphone DDS). Clinical Toxicology Review. 1999:21(9). 3 pages.
Gendron, Loxosceles ignali Envenomation. Am J Emerg Med. Jan. 1990;8(1):51-4.
Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.
Giannini et al., Influence of the Mucosal Epithelium Microenvironment on Langerhans Cells: Implications for the Development of Squamous Intraepithelial Lesions of the Cervix. Int J Cancer. 2002;97:654-59.
Gibson et al., Cellular requirements for cytokine production in response to the immunomodulators imiquimod and S-27609. J Interferon Cytokine Res. Jun. 1995;15(6):537-45.
Gibson et al., Plasmacytoid dendritic cells produce cytokines and mature in response to the TLR7 agonists, imiquimod and resiquimod. Cell Immunol. Jul.-Aug. 2002 ;218(1-2):74-86.
Gitelson et al., Chronic lymphocytic leukemia-reactive T cells during disease progression and after autologous tumor cell vaccines. Clin Cancer Res. May 2003;9(5):1656-65.
Gomez et al., Intradermal anti-loxosceles Fab fragments attenuate dermonecrotic arachnidism. Acad Emerg Med. 1999;6:1195-202.
Gorden et al., Synthetic TLR agonists reveal functional differences between human TLR7 and TLR8. J Immunol. Feb. 1, 2005;174(3):1259-68.
Gordon, Pattern recognition receptors: doubling up for the innate immune response. Cell. Dec. 27, 2002;111(7):927-30.
Gunning et al., Chemoprevention by lipoxygenase and leukotriene pathway inhibitors of vinyl carbamate-induced lung tumors in mice. Cancer Res. Aug. 1, 2002;62(15):4199-201.
Gürsel et al., Differential and competitive activation of human immune cells by distinct classes of CpG oligodeoxynucleotide. J Leukoc Biol. May 2002;71(5):813-20.
Hart, Napthyridines Hydroxynaphthyridies, Journal of Chemical Society, 1956;Part III:212-4.
Hartmann et al., Rational design of new CpG oligonucleotides that combine B cell activation with high IFN-alpha induction in plasmacytoid dendritic cells. Eur J Immunol. Jun. 2003;33(6):1633-41.
Hayashi Toll-like receptors stimulate human neutrophil function. Blood. Oct. 1, 2003;102(7):2660-69. Epub Jun. 26, 2003.
Hayes et al., Regulation of Interferon Production by Human Monocytes: Requirements for Priming for Lipopolysaccharide-Induced Production. J Leukocyte Biol. 1991;50:176-81.
Heil et al., Species-specific recognition of single-stranded RNA via toll-like receptor 7 and 8. Science. Mar. 5, 2004;303(5663):1526-9. Epub Feb. 19, 2004.
Heil et al., Synthetic immunostimulatory compounds activate immune cells via TLR7 and TLR8. 33th Annual Meeting of the Deutsche Gessellschaft Mr Immunologie, Marburg 2002. Abstract C.6.
Hemmi et al., Small anti-viral compounds activate immune cells via the TLR7 MyD88-dependent signaling pathway. Nat Immunol. Feb. 2002;3(2):196-200. Epub Jan. 22, 2002.
Hobbs et al., Comparison of hyperbaric oxygen and dapsone therapy for loxosceles envenomation. Acad Emerg Med. Aug. 1996;3(8):758-61.3
Hoffman et al., Conformational requirements for histamine H2-receptor inhibitors: a structure-activity study of phenylene analogues related to cimetidine and tiotidine. J Med Chem. Feb. 1983;26(2):140-4.
Hofmanová of al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.
Horng et al., The adaptor molecule TIRAP provides signaling specificity for Toll-like receptors. Nature. Nov. 21, 2002;420(6913):329-33.
Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.
Houben-Weyl, Quinoline and Isoquinoline. Methoden der Organischen Chemie. 1980:271-79. German.
Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. 5 Apr. 1985;28(4):467-71.
Huppatz, Systemic fungicides. The synthesis of certain pyrazole analogues of carboxin. Aust J Chem. 1983;36:135-47.
Iino et al., Treatment of Chronic Hepatitis C With High-Dose Interferon α-2b. Multicenter Study. Dig Dis Sci. 1993;38(4):612-18.
Ito et al., Interferon-alpha and interleukin-12 are induced differentially by Toll-like receptor 7 ligands in human blood dendritic cell subsets. J Exp Med. Jun. 3, 2002;195(11):1507-12.
Iwashita et al., Syntheses of Isoretronecanol and Lupinine. J Org Chem. 1982;47:230-33.
Izumi et al., 1H-Imidazo[4,5-c]quinoline derivatives as novel potent TNF-alpha suppressors: synthesis and structure-activity relationship of 1-, 2-and 4-substituted 1H-imidazo[4,5-c]quinolines or 1H-imidazo[4,5-c]pyridines. Bioorg Med Chem. Jun. 12, 2003;11(12):2541-50.
Jacobs, Chapter 1. The Synthesis of Acetylenes. In: Organic Reactions. New York: Wiley & Sons, Inc., 1949. vol. 5. 1-78. .
Jahnsen et al., Extensive recruitment of IL-3Rahigh dendritic-cell precursors to allergic nasal mucosa during allergen challenge. Immunology Lett. 1999;69(1):123. Abstract #32.2.
Jain et al., Chemical and pharmacological investigations of some omega-substituted alkylamino-3-aminopyridines. J Med Chem. Jan. 1968;11(1):87-92.
Jurk et al. Human TLR7 and TLR8 independently confer responsiveness to the antiviral compound R-848. Nat Immunol. Jun. 2002;3(6):499.
Juweid, Radioimmunotherapy of B-Cell Non-Hodgkin's Lymphoma: From Clinical Trials to Clinical Practice. J Nuclear Med. 2002;43(11):1507-29.
Katritsky et al., Comprehensive Heterocyclic Chemistry: The Structure, Reactions, Synthesis and Uses of Heterocyclic Compounds. 1984;2:586-587.
Keating et al., Long-term follow-up of patients with chronic lymphocytic leukemia treated with fludarabine as a single agent. Blood. Jun. 1, 1993;81(11):2878-84.
Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.
Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò -nitrokenes. J Am Chem Soc. 1947;69:2271-2275.
Kornman, Host modulation as a therapeutic strategy in the treatment of periodontal disease. Clin Infect Dis. Mar. 1999;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of γδ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 2006.

Leynadier et al., Allergic reactions to North African scorpion venom evaluated by skin test and specific IgE. J Allergy Clin Immunol. Jun. 1997;99(6 Pt 1):851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. 1997 American Association of Pharmaceutical Scientists Annual Meeting. Poster Presentation, Boston, MA, Nov. 2-6. Pharma Res. 1997;14(11):S475. Abstract 3029.

Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of Lactococcus lactis. Immunology Lett. 1999:69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2methyleneaminoxyethoxy)methyl]guanine derivatives as novel Acyclovir analogues. Farmaco. Feb. 2000;55(2):104-8.

Majeski et al., Action of venom from the brown recluse spider (Loxosceles reclusa) on human neutrophils. Toxicon. 1977;15(5):423-7.

Makarenkova et al., Identification of delta- and mu-type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al., Scalable Syntheses of $N^\alpha$-Benzyloxycarbonyl-L-Ornithine and of $N^\alpha$-(9-Fluorenylmethoxy)Carbonyl-L-Ornithine. Org Prep Proced Int. 2002;34:531-37.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

Mclaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stille coupling made easier-the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99m Tc complexes used in structure distribution relationiship (SDR) studies. Tetrahedron 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J Std & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., the repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., the necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., the opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COC-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998t;52(5):238-311.

Prelog et al., Cycloalkeno-pyridine. Hely Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer of al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

Seymour et al., Cellular immunity and hypersensitivity as components of periodontal destruction. Oral Dis. Mar. 1996;2(1):96-101. Review.

Shelburne at., Quantitation of Bacteroids forsythus in subgingival plaque comparison on immunoassay and quantitative polymerase chain reaction. J Microbiol Methods. 2000;39:97107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, *Loxosceles reclusa*. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80/1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et at., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub 2001 Jun. 8.

Stack, Images in clinical medicine. *Latrodectus mactans*. N. Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al', Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. 1997 American Association of Pharmaceutical Scientists Annual Meeting. Poster Presentation, Boston, MA, Nov. 2-6. Pharma Res. 1997;14(11):S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Testerman et al., Cytokine induction by the immunomodulators imiquimod and S-27609. J Leukoc Biol. Sep. 1995;58(3):365-72.

Thesing et al., [Darstellung and Eigenschaften des $\Delta^1$Pyrrolin-$N$-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov . 13, 1980;288(5787):176-8.

Tracy et al, Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al, eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells-the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate Identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Tray Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wozniak et al., The amination of 3-nitro-1, 5-naphthyridines by liquid ammonia/potassium permanganate1,2. A new and convenient animation method. J. Royal Netherlands Chem Soc. Dec. 12, 1983(102):511-3.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22. .

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and *Drosophila* nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J LeukocBiol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

\* cited by examiner

1-SUBSTITUTED PYRAZOLO (3,4-C) RING COMPOUNDS AS MODULATORS OF CYTOKINE BIOSYNTHESIS FOR THE TREATMENT OF VIRAL INFECTIONS AND NEOPLASTIC DISEASES

CROSS REFERENCE TO RELATED APPLICATIONS

This application is a national stage filing under 35 U.S.C. §371 of PCT International application PCT/US2006/12263 designating the United States of America, and filed Mar. 31, 2006. This application claims the benefit under 35 U.S.C. §119(e) of U.S. provisional application Ser. No. 60/667869, filed Apr. 1, 2005, and U.S. provisional application Ser. No. 60/733037, filed Nov. 3, 2005, both of which are incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula I:

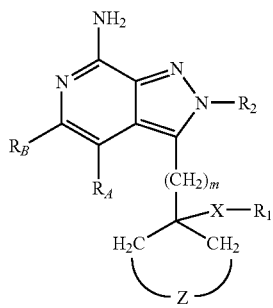

I wherein $R_1$, $R_2$, $R_A$, $R_B$, X, Z, and m are as defined below.

The compounds of Formula I are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I and methods of inducing cytokine biosynthesis in an animal, treating a viral infection or disease and/or treating a neoplastic disease in an animal by administering an effective amount of a compound of Formula I to the animal.

In addition, methods of synthesizing compounds of Formula I and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula I:

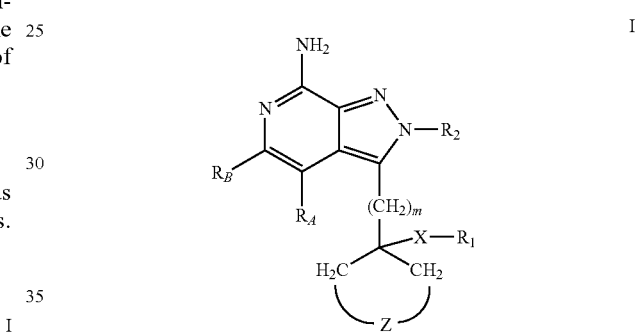

I and more specifically compounds of the following Formulas II, III, IV, V, VI, VII, VIII, XIII, and XIV:

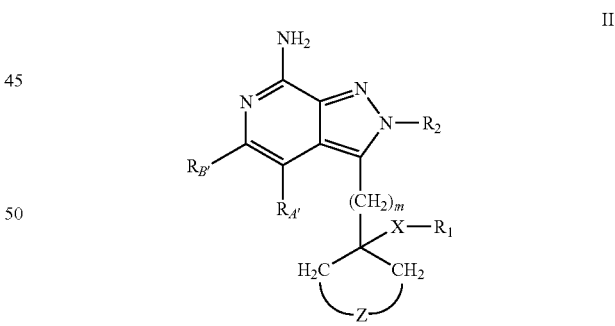

II

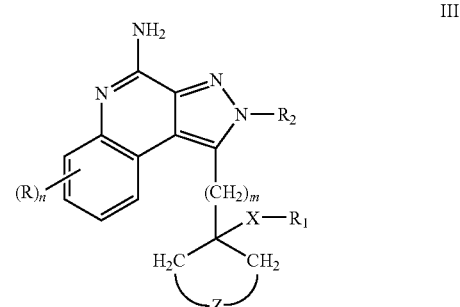

III

-continued
IV
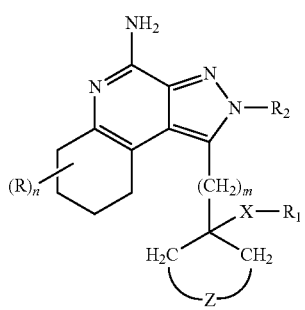
V
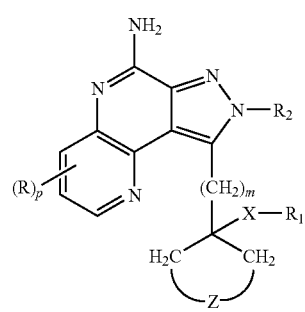
VI
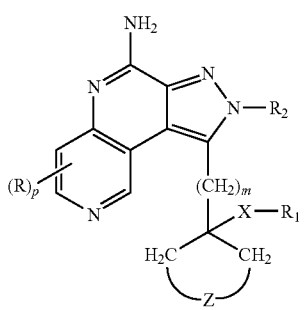
VII
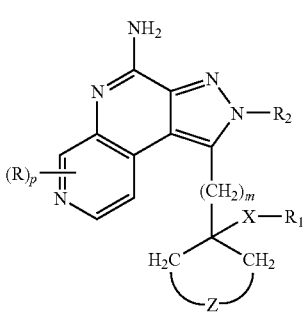
VIII
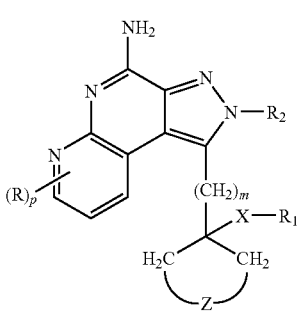
-continued
XIII
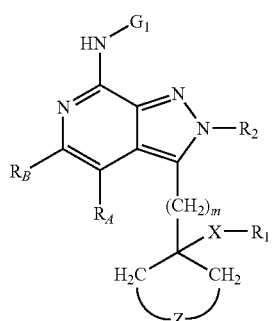
XIV
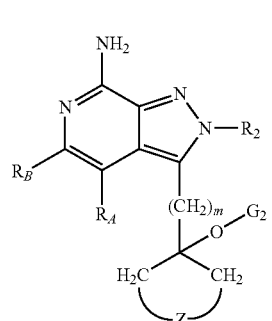
wherein $R_A$, $R_B$, $R_{A'}$, $R_{B'}$, R, $R_1$, $R_2$, m, n, p, X, Z, $G_1$, and $G_2$ are as defined below; and pharmaceutically acceptable salts thereof.
In one embodiment, the present invention provides a compound of the Formula I:
I
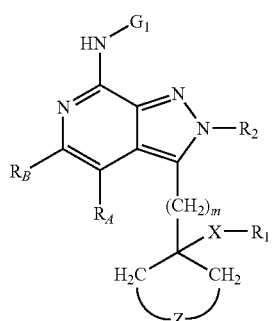
wherein:
Z is selected from the group consisting of:
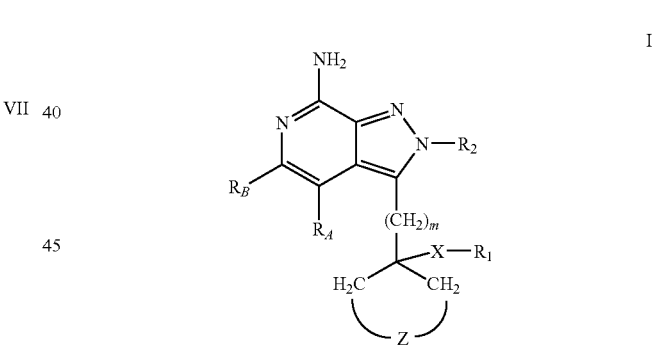
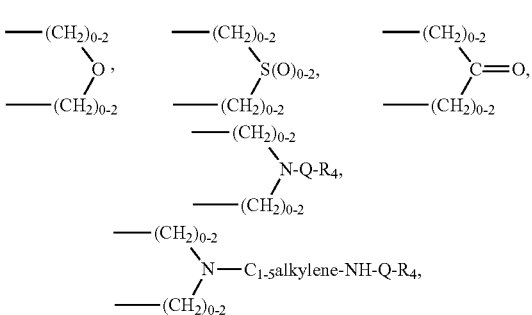

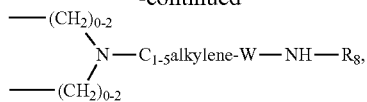

a bond,
C$_{1-5}$ alkylene,

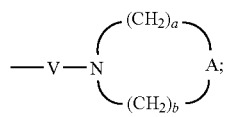

X is selected from the group consisting of a bond, —C$_{2-3}$ alkylene-, and —O—C$_{2-3}$ alkylene-;
R$_1$ is selected from the group consisting of:
hydrogen,
hydroxy,
fluorine,
alkoxy,
—N(R$_9$)$_2$,
—NH-Q-R$_4$,
—S(O)$_{0-2}$-alkyl,
—S(O)$_2$—NH—R$_9$,
—C(R$_6$)—N(R$_8$)—R$_4$,
—O—C(R$_6$)—N(R$_8$)—R$_4$,
—C(R$_6$)—O-alkyl,
—O—C(R$_6$)—R$_4$, and

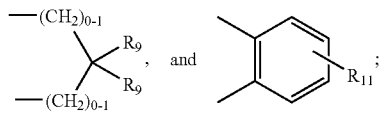

with the proviso that when Z is a bond, C$_{1-5}$ alkylene,

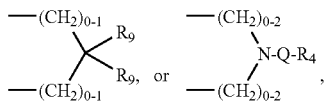

and X is a bond,
then R$_1$ is other than hydrogen;
m is an integer from 1 to 5;
R$_A$ and R$_B$ are each independently selected from the group consisting of:
hydrogen,
halogen,
alkyl,
alkenyl,
alkoxy,
alkylthio, and
—N(R$_9$)$_2$;
or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups;
or when taken together, R$_A$ and R$_B$ form a fused 5 to 7 membered saturated ring, optionally containing one heteroatom selected from the group consisting of N and S, and unsubstituted or substituted by one or more R groups;

R is selected from the group consisting of:
halogen,
hydroxy,
alkyl,
haloalkyl,
alkoxy, and
—N(R$_9$)$_2$;
R$_2$ is selected from the group consisting of:
hydrogen,
alkyl,
alkoxyalkylenyl,
hydroxyalkylenyl,
haloalkylenyl, and
R$_4$—C(R$_6$)—O—C$_{1-4}$ alkylenyl;
R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;
R$_6$ is selected from the group consisting of =O and =S;
R$_8$ is selected from the group consisting of hydrogen, alkyl, alkoxyalkylenyl, and arylalkylenyl;
R$_9$ is selected from the group consisting of hydrogen and alkyl;
R$_{11}$ is selected from the group consisting of hydrogen, alkyl, halogen, and trifluoromethyl;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7; or a pharmaceutically acceptable salt thereof.
In another embodiment, the present invention provides a compound of the Formula II:

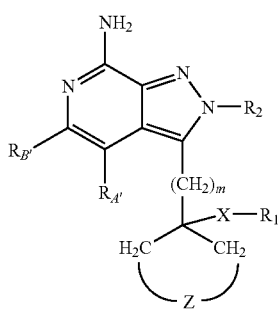

wherein:

Z, X, $R_1$, $R_2$, and m are as defined in Formula I; and $R_{A'}$ and $R_{B'}$ are each independently selected from the group consisting of:

hydrogen, halogen, alkyl, alkenyl, alkoxy, alkylthio, and

—$N(R_9)_2$;

or a pharmaceutically acceptable salt thereof.

In another embodiment, the present invention provides a compound of the Formula III:

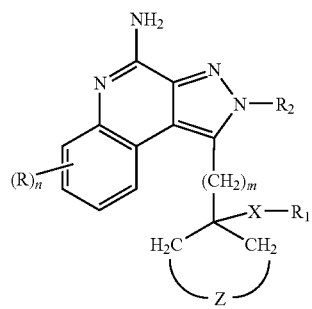

III wherein:

Z, X, $R_1$, $R_2$, R, and m are as defined in Formula I; and n is an integer from 0 to 4;

or a pharmaceutically acceptable salt thereof.

In another embodiment, the present invention provides a compound of the Formula IV:

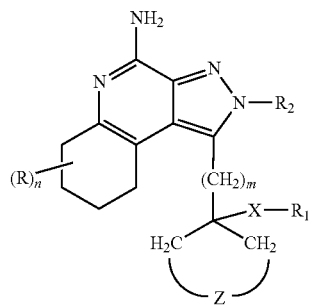

IV wherein:

Z, X, $R_1$, $R_2$, R, and m are as defined in Formula I; and n is an integer from 0 to 4;

or a pharmaceutically acceptable salt thereof.

In another embodiment, the present invention provides a compound selected from the group consisting of the Formulas V, VI, VII, and VIII:

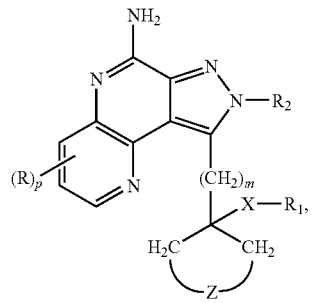

V

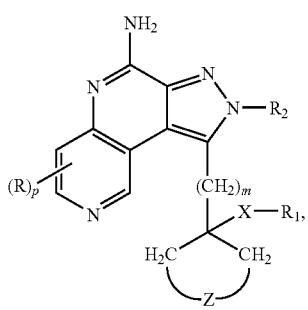

VI

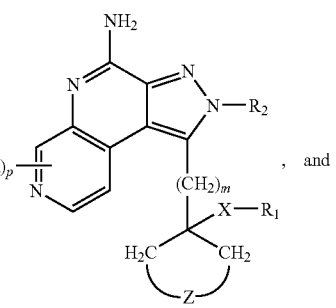

VII

, and

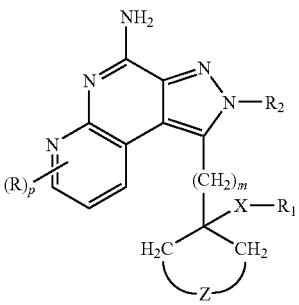

VIII wherein:

Z, X, $R_1$, $R_2$, R, and m are as defined in Formula I; and p is an integer from 0 to 3;

or a pharmaceutically acceptable salt thereof.

In another embodiment, the present invention provides a compound selected from the group consisting of the Formulas IX, X, XI, and XII:

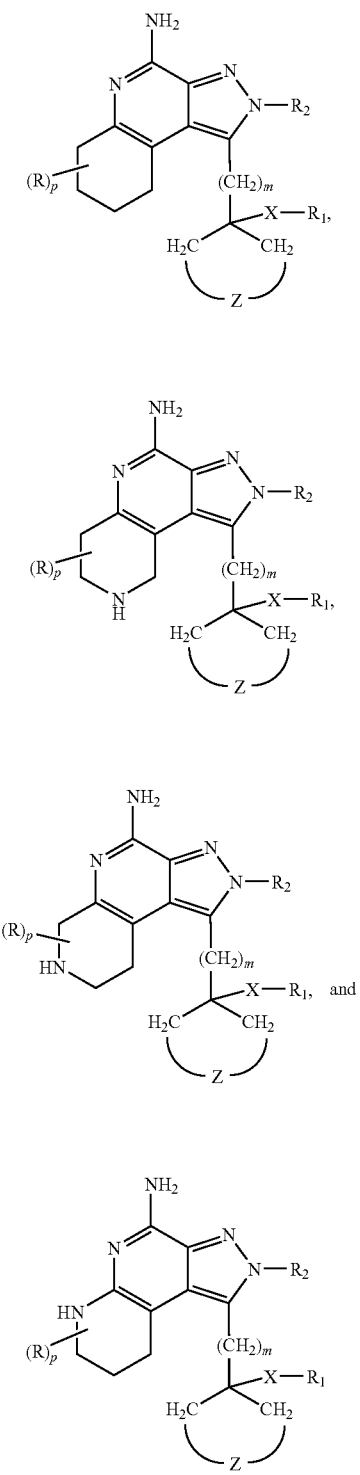

wherein:
Z, X, $R_1$, $R_2$, R, and m are as defined in Formula I; and
p is an integer from 0 to 3;
or a pharmaceutically acceptable salt thereof.

In another embodiment, the present invention provides a compound of the Formula XIII:

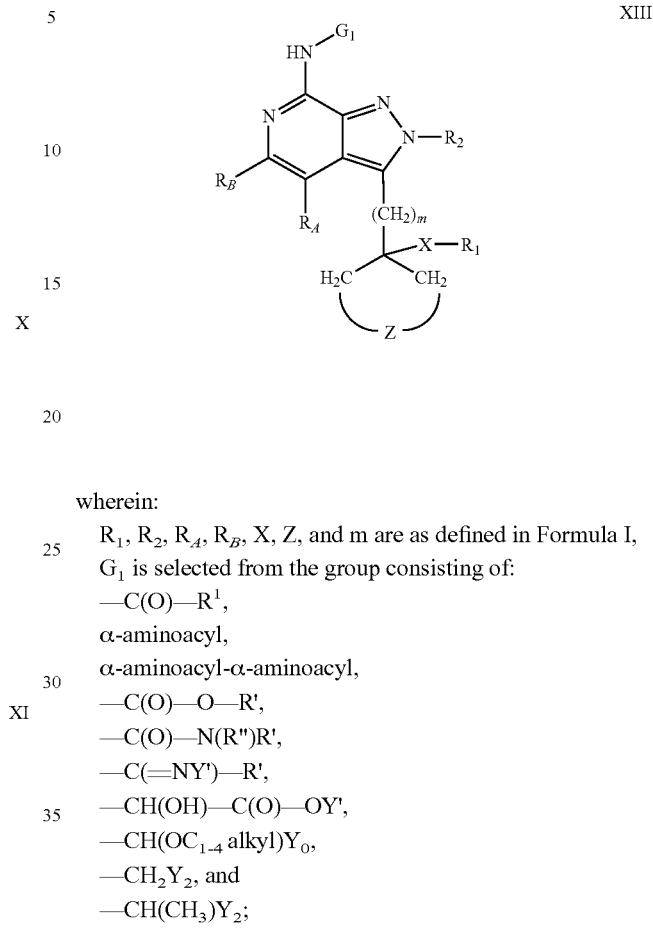

wherein:
$R_1$, $R_2$, $R_A$, $R_B$, X, Z, and m are as defined in Formula I,
$G_1$ is selected from the group consisting of:
—C(O)—R¹,
α-aminoacyl,
α-aminoacyl-α-aminoacyl,
—C(O)—O—R',
—C(O)—N(R")R',
—C(=NY')—R',
—CH(OH)—C(O)—OY',
—CH(O$C_{1-4}$ alkyl)$Y_0$,
—$CH_2Y_2$, and
—CH($CH_3$)$Y_2$;

R' and R" are independently selected from the group consisting of $C_{1-10}$ alkyl, $C_{3-7}$ cycloalkyl, phenyl, and benzyl, each of which may be unsubstituted or substituted by one or more substituents selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen;

α-aminoacyl is an α-aminoacyl group derived from an amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_4$ alkylamino-$C_{1-4}$ alkylenyl; and $Y_2$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;

or a pharmaceutically acceptable salt thereof.

In another embodiment, the present invention provides a compound of the Formula XIV:

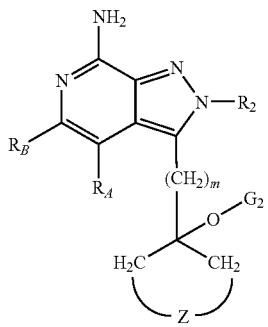

XIV wherein:
$R_A$, $R_B$, $R_2$, Z, and m are as defined in Formula I,
$G_2$ is selected from the group consisting of:
—$X_2$—C(O)—R',
α-aminoacyl,
α-aminoacyl-α-aminoacyl,
—$X_2$—C(O)—O—R',
—C(O)—N(R")R', and
—S(O)$_2$—R';

$X_2$ is selected from the group consisting of a bond; —CH$_2$—O—; —CH(CH$_3$)—O—; —C(CH$_3$)$_2$—O—; and, in the case of —$X_2$—C(O)—O—R', —CH$_2$—NH—;

R' and R" are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and α-aminoacyl is an α-aminoacyl group derived from an amino acid selected from the group consisting of racemic, D-, and L-amino acids;
or a pharmaceutically acceptable salt thereof.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "fused heteroaryl ring" includes the fused forms of 5 or 6 membered aromatic rings that contain one heteroatom selected from S and N.

The term "fused 5 to 7 membered saturated ring" includes rings which are fully saturated except for the bond where the ring is fused.

When a group (or substituent or variable) is present more than once in any formula described herein, each group (or substituent or variable) is independently selected, whether explicitly stated or not. For example, for the formula —N(R$_9$)— each R$_9$ group is independently selected. In another example, when an R$_1$ and a Z group both contain an R$_4$ group, each R$_4$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Compounds (including intermediates) of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (prototropic tautomers) include interconversions via migration of a proton, such as keto-enol and imine-enamine isomerizations. When compounds of the present invention have a hydrogen atom at the 2 position, proton migration between the 2 and 3 positions may occur.

The compounds of the present invention may exist in unsolvated as well as solvated forms with pharmaceutically acceptable solvents such as water, ethanol, and the like. The present invention embraces both solvated and unsolvated forms.

For any of the compounds presented herein, each one of the following variables (e.g., R$_A$, R$_B$, R$_A$', R$_B$', R, R$_1$, R$_2$, m, n, p, A, Q, X, Z, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In certain embodiments (e.g., of Formula I), R$_A$ and R$_B$ are each independently selected from the group consisting of hydrogen, halogen, alkyl, alkenyl, alkoxy, alkylthio, and —N(R$_9$)$_2$;
or when taken together, R$_A$ and R$_B$ form a fused aryl ring or heteroaryl ring containing one heteroatom selected from the group consisting of N and S wherein the aryl or heteroaryl ring is unsubstituted or substituted by one or more R groups;
or when taken together, R$_A$ and R$_B$ form a fused 5 to 7 membered saturated ring, optionally containing one heteroatom selected from the group consisting of N and S, and unsubstituted or substituted by one or more R groups.

In certain embodiments (e.g., of Formula I), R$_A$ and R$_B$ are each independently selected from the group consisting of hydrogen, halogen, alkyl, alkenyl, alkoxy, alkylthio, and —N(R$_9$)$_2$.

In certain embodiments (e.g., of Formula I), R$_A$ and R$_B$ form a fused aryl or heteroaryl ring.

In certain embodiments (e.g., of Formula I), R$_A$ and R$_B$ form a fused aryl ring. In certain embodiments, the fused aryl ring is benzo.

In certain embodiments (e.g., of Formula I), R$_A$ and R$_B$ form a fused heteroaryl ring. In certain embodiments, the fused heteroaryl ring is pyrido or thieno. In certain embodiments, the fused heteroaryl ring is pyrido. In certain of these embodiments, the pyrido ring is

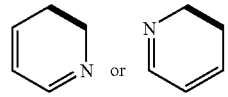

wherein the highlighted bond indicates the position where the ring is fused.

In certain embodiments (e.g., of Formula I), R$_A$ and R$_B$ form a fused 5 to 7 membered saturated ring. In certain embodiments, the ring is a cyclohexene ring.

In certain embodiments (e.g., of Formula I), R$_A$ and R$_B$ form a fused 5 to 7 membered saturated ring containing one heteroatom selected from the group consisting of N and S. In certain embodiments, the ring is tetrahydropyrido or dihydrothieno. In certain embodiments the heteroatom is N. In certain embodiments, the ring is tetrahydropyrido.

In certain of these embodiments, the ring is

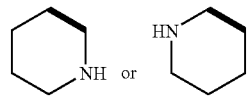

wherein the highlighted bond indicates the position where the ring is fused.

In certain embodiments (e.g., of Formula II), R$_A$' and R$_B$' are each independently selected from the group consisting of hydrogen, halogen, alkyl, alkenyl, alkoxy, alkylthio, and —N(R$_9$)$_2$.

In certain embodiments (e.g., of Formula II), R$_A$' and R$_B$' are independently hydrogen or alkyl.

In certain embodiments (e.g., of Formula II), R$_A$' and R$_B$' are both methyl.

In certain embodiments (e.g., of any one of Formulas IX through XII), R is selected from the group consisting of alkyl and haloalkyl.

In certain embodiments (e.g., of any one of the above embodiments of Formulas I, III through VIII, XIII, and XIV where R is present), R is selected from the group consisting of alkyl, alkoxy, halogen, and hydroxy.

In certain embodiments (e.g., of any one of the above embodiments of Formulas I, III through VIII, XIII, and XIV where R is present), R is hydroxy.

In certain embodiments (e.g., of Formulas III or IV), n is 0.

In certain embodiments (e.g., of any one of Formulas V through XII), p is 0.

In certain embodiments, the compound or salt selected from the group consisting of Formulas V, VI, VII, and VIII is the compound of Formula V or Formula VIII:

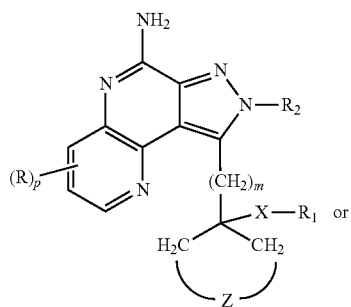

V

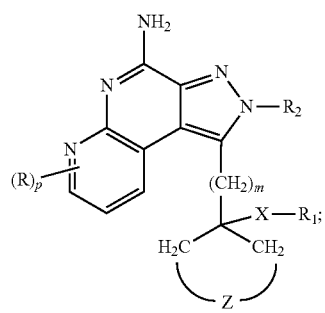

VIII or a pharmaceutically acceptable salt thereof.

In certain embodiments (e.g., of any one of Formulas I through XIV), m is an integer from 1 to 5.

In certain embodiments, including any one of the above embodiments, m is an integer from 1 to 3. In certain embodiments, m is 1.

In certain embodiments (e.g., of any one of Formulas I through XIII), X is selected from the group consisting of a bond, —$C_{2-3}$ alkylene-, and —O—$C_{2-3}$ alkylene-.

In certain embodiments, including any one of the above embodiments, X is a bond.

In certain embodiments (e.g., of any one of Formulas I through XIII), $R_1$ is selected from the group consisting of hydrogen, hydroxy, fluorine, alkoxy, —N($R_9$)$_2$, —NH-Q-$R_4$, —S(O)$_{0-2}$-alkyl, —S(O)$_2$—NH—$R_9$, —C($R_6$)—N($R_8$)—$R_4$, —O—C($R_6$)—N($R_8$)—$R_4$, —C($R_6$)—O-alkyl, —O—C($R_6$)—$R_4$, and

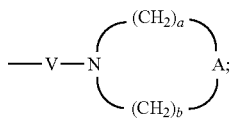

with the proviso that when Z is a bond, $C_{1-5}$ alkylene,

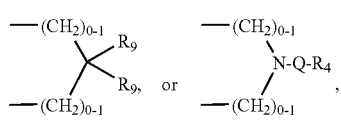

and X is a bond, then $R_1$ is other than hydrogen.

In certain embodiments, including any one of the above embodiments wherein $R_1$ is present, $R_1$ is selected from the group consisting of hydroxy and methoxy.

In certain embodiments, including any one of the above embodiments wherein $R_1$ is present, $R_1$ is fluoro, except where $R_1$ is otherwise defined.

In certain embodiments, including any one of the above embodiments wherein $R_1$ is present, $R_1$ is selected from the group consisting of —NH$_2$, —NH-Q-$R_4$, —C(O)—NH$_2$, and —C(O)—N($R_8$)—$R_4$, wherein Q is selected from the group consisting of —C(O)—, —S(O)$_2$—, —C(O)—O—, and —C(O)—NH—, $R_8$ is selected from the group consisting of hydrogen and alkyl, and $R_4$ is selected from the group consisting of alkyl and alkoxyalkylenyl, except where $R_1$ is otherwise defined.

In certain embodiments (e.g., of any one of Formulas I through XIV), Z is selected from the group consisting of:

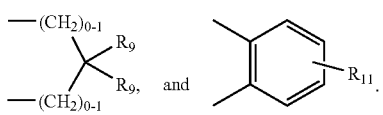

a bond, $C_{1-5}$ alkylene,

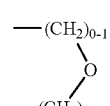

In certain embodiments, including any one of the above embodiments, Z is selected from the group consisting of a bond and $C_{1-3}$ alkylene.

In certain embodiments, including any one of the above embodiments, Z is selected from the group consisting of:

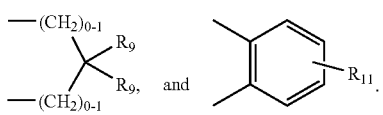

except where Z is otherwise defined. In certain of these embodiments, Z is

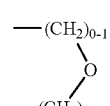

In certain embodiments, including any one of the above embodiments wherein X is a bond and Z is

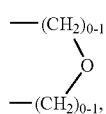

$R_1$ is hydrogen.

In certain embodiments, including embodiments of Formula III wherein n is 0, and embodiments of Formulas V, VI, VII, or VIII wherein p is 0, and embodiments of Formulas IX, X, XI, or XI wherein p is 0, Z is

X is a bond, and $R_1$ is hydrogen.

In certain embodiments, including any one of the above embodiments, Z is

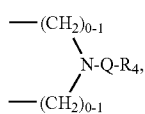

except where Z is otherwise defined.

In certain embodiments, including any one of the above embodiments wherein Q is present, Q is selected from the group consisting of —C(O)—, —C(O)—O—, —S(O)$_2$—, and —C($R_6$)—N($R_8$)—.

In certain embodiments, including any one of the above embodiments wherein $R_4$ is present, $R_4$ is selected from the group consisting of alkyl, aryl, arylalkylene, heteroaryl, and heterocyclyl, wherein the aryl group can be unsubstituted or substituted by one or more substituents independently selected from the group consisting of acetylamino, alkyl, alkoxy, cyano, and halogen.

In certain embodiments (e.g., of any one of Formulas I through XIV), $R_2$ is selected from the group consisting of hydrogen, alkyl, alkoxyalkylenyl, hydroxyalkylenyl, haloalkylenyl, and $R_4$—C($R_6$)—O—C$_{1-4}$ alkylenyl.

In certain embodiments, including any one of the above embodiments, $R_2$ is selected from the group consisting of C$_{1-4}$ alkyl, C$_{1-4}$ alkyl-O—C$_{2-4}$ alkylenyl, and hydroxyC$_{2-4}$ alkylenyl.

In certain embodiments, including any one of the above embodiments, $R_2$ is selected from the group consisting of methyl, ethyl, n-propyl, n-butyl, 2-methoxyethyl, and 2-hydroxyethyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of allyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo.

For certain embodiments, $R_4$ is selected from the group consisting of alkyl and alkoxyalkylenyl.

For certain embodiments, $R_4$ is selected from the group consisting of alkyl, aryl, arylalkylene, heteroaryl, and heterocyclyl, wherein the aryl group can be unsubstituted or substituted by one or more substituents independently selected from the group consisting of acetylamino, alkyl, alkoxy, cyano, and halogen.

For certain embodiments, $R_6$ is selected from the group consisting of =O and =S. In certain embodiments, $R_6$ is =O. In certain embodiments, $R_6$ is =S.

For certain embodiments, $R_8$ is selected from the group consisting of hydrogen, alkyl, alkoxyalkylenyl, and arylalkylenyl. In certain embodiments, $R_8$ is selected from the group consisting of hydrogen and alkyl. In certain embodiments, $R_8$ is hydrogen. In certain embodiments, $R_8$ is alkyl.

For certain embodiments, $R_9$ is selected from the group consisting of hydrogen and alkyl. In certain embodiments, $R_9$ is alkyl. In certain embodiments, $R_9$ is hydrogen.

For certain embodiments, $R_{11}$ is selected from the group consisting of hydrogen, alkyl, halogen, and trifluoromethyl.

For certain embodiments, A is selected from the group consisting of —O—, —C(O)—, —S(O)$_{0-2}$—, —CH$_2$—, and —N($R_4$)—. For certain embodiments, A is —O—.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—. For certain embodiments, Q is selected from the group consisting of —C(O)—, —S(O)$_2$—, —C(O)—O—, and —C(O)—NH—. For certain embodiments, Q is selected from the group consisting of —C(O)—, —C(O)—O—, —S(O)$_2$—, and —C($R_6$)—N($R_8$)—. For certain embodiments, Q is a bond.

For certain embodiments, V is selected from the group consisting of —C($R_6$)—, —O—C($R_6$)—, —N($R_8$)—C($R_6$)—, and —S(O)$_2$—. In certain embodiments, V is —C($R_6$)—. In certain embodiments, V is —N($R_8$)—C($R_6$)—.

For certain embodiments, W is selected from the group consisting of a bond, —C(O)—, and —S(O)$_2$—. In certain embodiments, W is selected from the group consisting of a bond and —C(O)—. In certain embodiments, W is a bond.

For certain embodiments, a and b are independently integers from 1 to 6 with the proviso that a+b is ≦7. For certain embodiments, a and b are each the integer 2.

For certain embodiments, $G_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_2$, and —CH(CH$_3$)Y$_2$.

For certain embodiments, $G_2$ is selected from the group consisting of —X$_2$—C(O)—R', α-aminoacyl, α-aminoacyl-α-aminoacyl, —X$_2$—C(O)—O—R', —C(O)—N(R")R', and —S(O)$_2$—R'.

For certain embodiments, R' is selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$.

For certain embodiments, R" is selected from the group consisting of hydrogen, $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$.

For certain embodiments, $X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—.

For certain embodiments, α-aminoacyl is an α-aminoacyl group derived from an amino acid selected from the group consisting of racemic, D-, and L-amino acids. For certain of these embodiments, the amino acid is a naturally occurring amino acid.

For certain embodiments, Y' is selected from the group consisting of hydrogen, $C_{1-6}$ alkyl, and benzyl.

For certain embodiments, $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl.

For certain embodiments, $Y_2$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula XIII, $G_1$ is selected from the group consisting of —C(O)—R', α-aminoacyl, and —C(O)—O—R'. For certain of these embodiments, R' contains one to ten carbon atoms. For certain of these embodiments, α-aminoacyl is an α-$C_{2-11}$ aminoacyl group derived from an α-amino acid selected from the group consisting of racemic, D-, and L-amino acids containing a total of at least 2 carbon atoms and a total of up to 11 carbon atoms, and may also include one or more heteroatoms selected from the group consisting of O, S, and N.

For certain embodiments, including any one of the above embodiments of Formula XIV, $G_2$ is selected from the group consisting of —C(O)—R' and α-aminoacyl, wherein R' is $C_{1-6}$ alkyl or phenyl which is unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$.

For certain embodiments, including any one of the above embodiments of Formula XIV, $G_2$ is selected from the group consisting of α-amino-$C_{2-5}$ alkanoyl, $C_{2-6}$ alkanoyl, $C_{1-6}$ alkoxycarbonyl, and $C_{1-6}$ alkylcarbamoyl.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the amino acid is selected from the group consisting of racemic, D-, and L-amino acids.

In some embodiments, the present invention provides a pharmaceutical composition comprising a therapeutically effective amount of a compound or salt of any one of Formulas I, II, III, IV, V, VI, VII, VIII, IX, X, XI, XII, XIII, XIV, or any one of the above embodiments in combination with a pharmaceutically acceptable carrier.

In some embodiments, the present invention provides a method of inducing cytokine biosynthesis in an animal comprising administering an effective amount of a compound or salt of any one of Formulas I, II, III, IV, V, VI, VII, VIII, IX, X, XI, XII, XIII, XIV, or any one of the above embodiments or administering any one of the above pharmaceutical compositions to the animal. For certain of these embodiments, the cytokine is selected from the group consisting of IFN-α, TNF-α, IL-6, IL-10, and IL-12. For certain of these embodiments, the cytokine is IFN-α or TNF-α.

In some embodiments, the present invention provides a method of treating a viral disease in an animal comprising administering a therapeutically effective amount of a compound or salt of any one of Formulas I, II, III, IV, V, VI, VII, VIII, IX, X, XI, XII, XIII, XIV, or any one of the above embodiments or administering any one of the above pharmaceutical compositions to the animal.

In some embodiments, the present invention provides a method of treating a neoplastic disease in an animal comprising administering a therapeutically effective amount of a compound or salt of any one of Formulas I, II, III, IV, V, VI, VII, VIII, IX, X, XI, XII, XIII, XIV, or any one of the above embodiments or administering any one of the above pharmaceutical compositions to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g. prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Belsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography, recrystallization, and differential (i.e., liquid-liquid) extraction techniques.

For some embodiments, compounds of the invention can be prepared according to Reaction Scheme I, where R, $R_2$, Z, n and m are as defined above and Boc is tert-butoxycarbonyl.

In step (1) of Reaction Scheme I, an indole of Formula XX is acylated to provide an oxalated indole of Formula XXI. The reaction can be carried out by adding ethyl chlorooxoacetate to a solution of an indole of Formula XX in a suitable solvent such as diethyl ether in the presence of pyridine. The reaction can be carried out at a sub-ambient temperature such as 0° C. Many indoles of Formula XX are known. Some are commercially available and others can be readily prepared using known synthetic methods.

In step (2) of Reaction Scheme I, an oxalated indole of Formula XXI is rearranged to a pyrazolo[3,4-c]quinolin-4-one of Formula XXII. The reaction can be carried out by adding a hydrazine of Formula $R_2NHNH_2$ to a solution of an oxalated indole of Formula XXI in a solvent or solvent mix such as ethanol/acetic acid in the presence of hydrochloric acid. The reaction can be carried out at an elevated temperature such as at reflux.

If step (2) is carried out using hydrazine, the resulting pyrazolo[3,4-c]quinolin-4-one of Formula XXII where $R_2$ is hydrogen can be further elaborated using known synthetic methods. For example, a pyrazolo[3,4-c]quinolin-4-one of Formula XXII where $R_2$ is hydrogen can alkylated. The alkylation is conveniently carried out by treating a solution of a pyrazolo[3,4-c]quinolin-4-one of Formula XXII, where $R_2$ is hydrogen, with a base such as sodium ethoxide followed by the addition of an alkyl halide. The reaction can be run in a suitable solvent such as ethanol and can be carried out at an elevated temperature, for example, the reflux temperature of the solvent, or at ambient temperature. Alternatively, a pyrazolo[3,4-c]quinolin-4-one of Formula XXII where $R_2$ is hydrogen can undergo a Buchwald amination with an aryl halide or heteroaryl halide. Numerous alkyl halides, aryl halides, and heteroaryl halides are commercially available; others can be prepared using known synthetic methods.

In step (3) of Reaction Scheme I, a pyrazolo[3,4-c]quinolin-4-one of Formula XXII is chlorinated to provide a 4-chloropyrazolo[3,4-c]quinoline of Formula XXIII. The reaction can be carried out by combining a pyrazolo[3,4-c]quinolin-4-one of Formula XXII with phosphorous oxychloride and heating.

In step (4) of Reaction Scheme I, the chloro group of a 4-chloropyrazolo[3,4-c]quinoline of Formula XXIII is displaced to provide a pyrazolo[3,4-c]quinolin-4-amine of Formula XXIV. The reaction can be carried out by combining a compound of Formula XXIII with a solution of ammonia in methanol and heating the mixture in a sealed reactor.

In step (5) of Reaction Scheme I, the amino group of a pyrazolo[3,4-c]quinolin-4-amine of Formula XXIV is protected with two Boc groups using conventional methods.

In step (6) of Reaction Scheme I, a compound of Formula XXV undergoes a lithiation-substitution reaction to provide a compound of Formula XXVI, which is a subgenus of Formula XIII. The reaction can be carried out by treating a compound of Formula XXV with tert-butyllithium and subsequently adding a cyclic ketone. Other organolithium reagents may be used. The reaction can be carried out below room temperature in a suitable solvent such as diethyl ether, THF, or tert-butyl methyl ether. Conveniently, the reaction can be carried out at −78° C. Numerous cyclic ketones useful in this transformation are commercially available, such as cyclohexanone, cyclopentanone, tetrahydro-4H-pyran-4-one, and 1-Boc-4-piperidone. Others can be made by known methods.

In step (7) of Reaction Scheme I, a Boc protected pyrazolo[3,4-c]quinolin-4-amine of Formula XXVI undergoes acid mediated cleavage to remove the Boc group to provide a compound of Formula XXVII which is a subgenus of Formulas I and III.

Reaction Scheme I

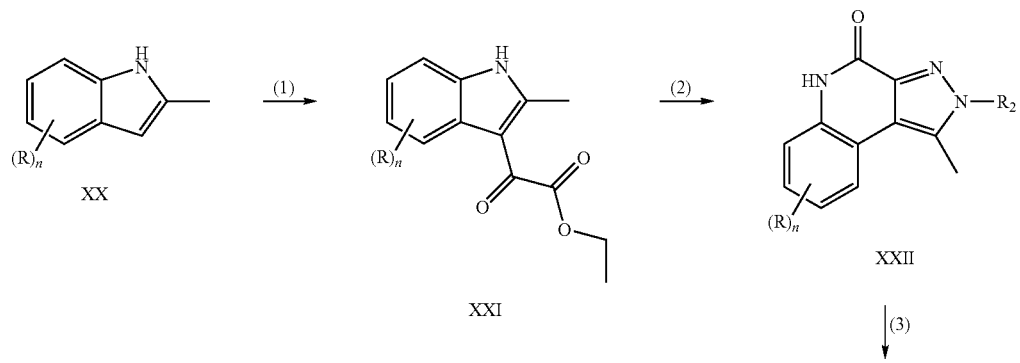

-continued

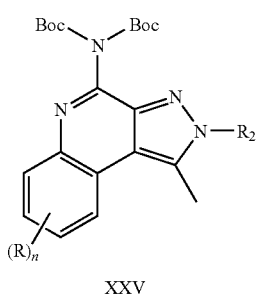 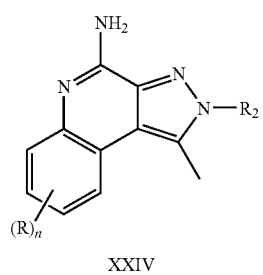 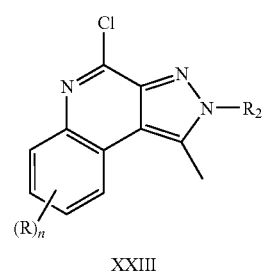

XXV  XXIV  XXIII

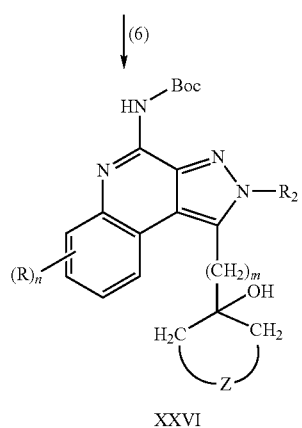

XXVI  XXVII

For some embodiments, compounds of the invention can be prepared according to Reaction Scheme II, where R, $R_2$, Z, n and m are as defined above.

In Reaction Scheme II, compounds of Formula XXIX are prepared from 7-azaindoles of Formula XXVIII using the methods of steps (1) through (7) of Reaction Scheme I.

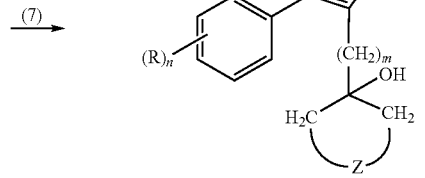

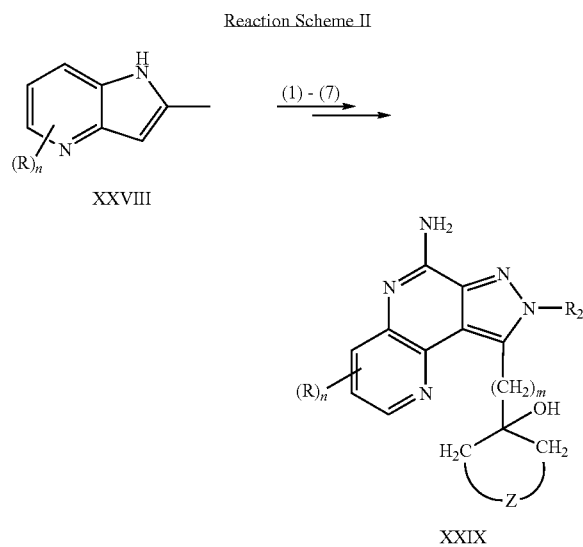

XXIX

For some embodiments, compounds of the invention can also be prepared according to Reaction Scheme III, where $R_1$, $R_2$, X, Z, and m are as defined above, and $R_{A2}$ and $R_{B2}$ taken together form a fused benzene ring or fused pyridine ring wherein the benzene ring or pyridine ring is unsubstituted or substituted by one or more R groups.

In step (1) of Reaction Scheme III, a ketone of Formula XXX is condensed with diethyl oxalate under Claisen condensation conditions to provide a ketoester of Formula XXXI. The reaction can be carried out by adding sodium tert-butoxide to a solution of diethyl oxalate and the ketone of Formula XXX in ethanol at ambient temperature.

In step (2) of Reaction Scheme III, a ketoester of Formula XXXI reacts with a hydrazine of Formula $R_2NHNH_2$ to provide a pyrazole carboxylate of Formula XXXI. The reaction is conveniently carried out by slowly adding the hydrazine to a solution of a compound of Formula XXXI in a suitable solvent such as acetic acid. The reaction can be carried out at ambient temperature.

In step (3) of Reaction Scheme III, the ester group of a pyrazole carboxylate of Formula XXXII is converted to an amide. The amination can be carried out by adding ammonium hydroxide to the pyrazole carboxylate of Formula XXXII in a suitable solvent such as methanol and heating at an elevated temperature such as 100° C. The reaction can be carried out in a pressure vessel.

Alternatively, step (3) can be carried out by first hydrolyzing a pyrazole carboxylate of Formula XXXII to a carboxylic acid and then converting the carboxylic acid to an amide. The ester hydrolysis can be carried out under basic conditions by combining a pyrazole carboxylate of Formula XXXII with lithium hydroxide or sodium hydroxide in water and in a suitable solvent such as methanol or ethanol. The reaction can be carried out at ambient temperature, and the carboxylic acid product can be isolated using conventional methods. The conversion of the carboxylic acid to a pyrazole carboxamide of Formula XXXIII can be carried out by first treating the carboxylic acid with oxalyl chloride at ambient temperature in a suitable solvent such as dichloromethane to generate an acid chloride, which can then be treated with ammonium hydroxide at a sub-ambient temperature such as 0° C. Alternatively, the conversion of the carboxylic acid to a pyrazole carboxamide of Formula XXXIII can be carried out under coupling conditions by adding 1-hydroxybenzotriazole and 1-(3-dimethylaminopropyl)-3-ethylcarbodiimide hydrochloride to a solution of the carboxylic acid in a suitable solvent such as N,N-dimethylformamide (DMF) at ambient temperature and then adding concentrated ammonium hydroxide.

In step (4) of Reaction Scheme III, a pyrazole carboxamide of Formula XXXIII is dehydrated to a pyrazole carbonitrile of Formula XXXIV. Suitable dehydrating agents include thionyl chloride, trifluoroacetic anhydride, and phosphorous oxychloride. The reaction is conveniently carried out by treating the pyrazole carboxamide of Formula XXXIII with phosphorous oxychloride and heating the reaction at an elevated temperature such as 90° C. The reaction can also be carried out by combining the pyrazole carboxamide of Formula XXXIII with trifluoroacetic anhydride in the presence of a base such as triethylamine and in a suitable solvent such as dichloromethane. The reaction can be carried out at ambient temperature or at a sub-ambient temperature such as 0° C.

In step (5) of Reaction Scheme III, a pyrazole carbonitrile of Formula XXXIV is brominated to provide a bromo-substituted pyrazole carbonitrile of Formula XXXV. The bromination is conveniently carried out by adding bromine to a solution of the pyrazole carbonitrile of Formula XXXIV and potassium acetate in acetic acid. The reaction can be carried out at ambient temperature.

In step (6) of Reaction Scheme III, a bromo-substituted pyrazole of Formula XXXV undergoes a transition-metal catalyzed cross coupling reaction with a reagent of Formula XXXVI. Reagents of Formula XXXVI, where M is, for example, —B(OH)$_2$, —B(O-alkyl)$_2$, —Sn(alkyl)$_3$, and —Zn-Halide, are known to undergo coupling reactions. Several reagents of Formula VI or their protected analogs are commercially available, for example, including 2-aminophenylboronic acid, 2-aminophenylboronic acid hydrochloride, and (2,2-dimethyl-N-[3-(4,4,5,5-tetramethyl-1,3,2-dioxaborolan-2-yl)pyridin-4-yl]propanamide; others can be prepared using known synthetic methods. For example, tert-butoxycarbonyl (Boc)-protected anilines undergo directed ortho metalation in the presence of butyllithium reagents. The resulting organolithium intermediate reacts with electrophiles such as B(O-alkyl)$_3$ and ClSn(alkyl)$_3$ to provide compounds of Formula XXXVI, where M is —B(O-alkyl)$_2$ or —B(OH)$_2$ and —Sn(alkyl)$_3$, respectively, after removal of the Boc protecting group.

In step (6), a Suzuki coupling reaction is conveniently carried out by heating a mixture of the bromo-substituted pyrazole of Formula XXX, dichlorobis(triphenylphosphine) palladium(II) and a boron reagent of Formula XXXVI, where M is —B(OH)$_2$ or —B(O-alkyl)$_2$, in the presence of a base such as potassium carbonate. The reaction is carried out in a suitable solvent such as 1,2-dimethoxyethane and can be heated at an elevated temperature such as 75-95° C.

In step (7) of Reaction Scheme III, the amine and nitrile functionalities of a pyrazole of Formula XXXVII react under acidic conditions to form a pyrazolo[3,4-c]quinoline or pyrazolo[3,4-c]naphthyridine of Formula XXXVIII. The intramolecular addition is conveniently carried out by stirring acetyl chloride in ethanol and adding the resulting acidic solution to the pyrazole of Formula XXXVIII. The reaction is then heated at reflux to provide the pyrazolo[3,4-c]quinoline or pyrazolo[3,4-c]naphthyridine of Formula XXXVIII.

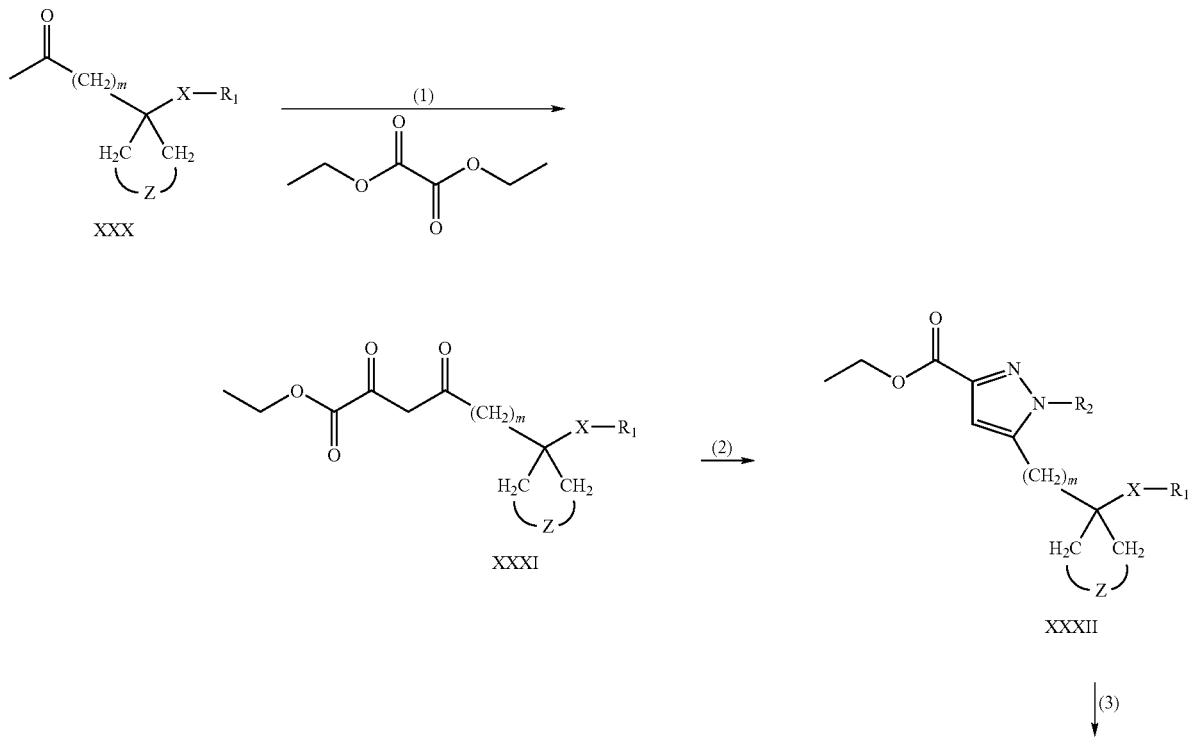

Reaction Scheme III

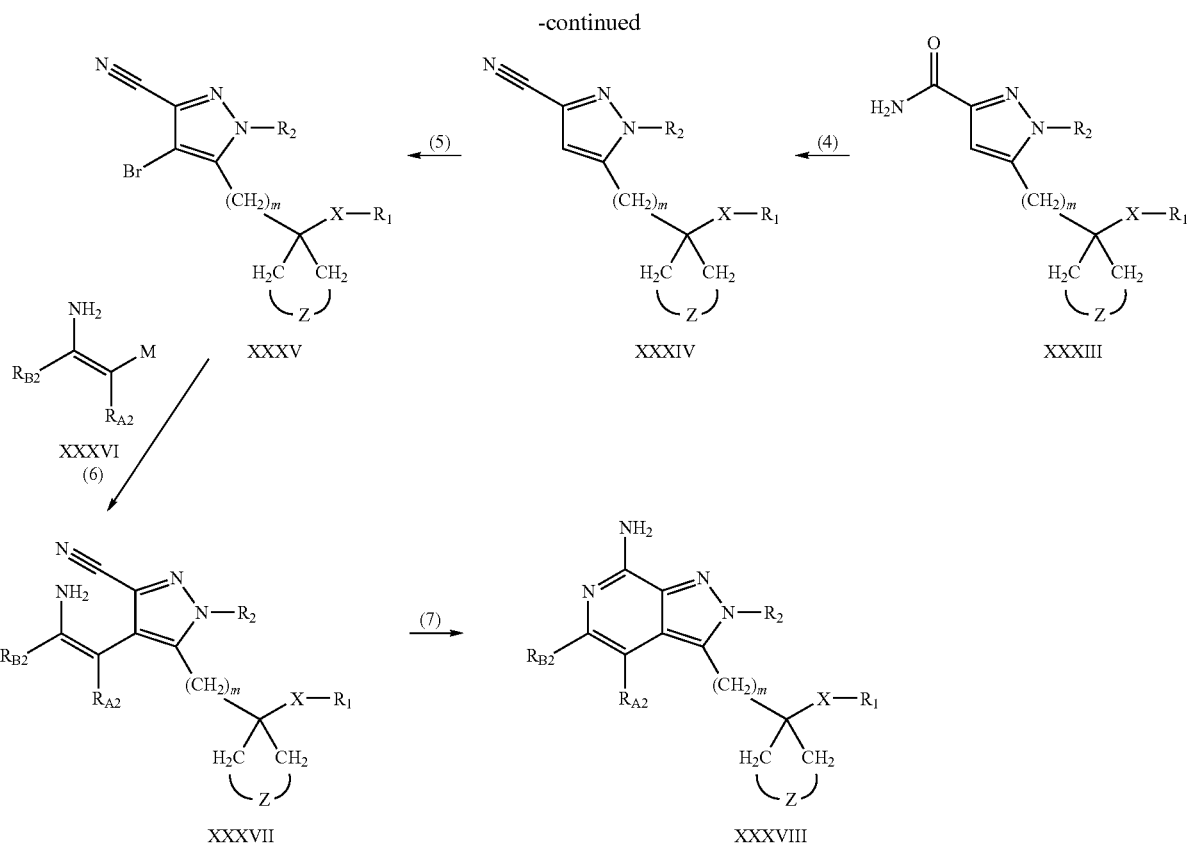

In some embodiments, compounds of the invention can be prepared according to Reaction Scheme IV where $R_1$, $R_2$, X, Z, and m are as defined above and $R_{A1}$ and $R_{B1}$ are as defined below.

In step (1) of Reaction Scheme IV, a bromo-substituted pyrazole carbonitrile of Formula XXXV undergoes a Sonogashira coupling reaction with (trimethylsilyl)acetylene to provide a pyrazole carbonitrile of Formula XXXIX. The reaction can be carried out according to the literature procedure, Sonogashira, K.; Tohda, Y.; Hagihara, N., *Tetrahedron Lett.,* 4467 (1975).

Alternatively, the iodo analog may be used as a starting material for Reaction Scheme IV. The iodo analog can be prepared from a pyrazole carbonitrile of Formula XXIV, shown in Reaction Scheme III. The iodination can be carried out by treating a pyrazole carbonitrile of Formula XXXIV with iodine monochloride in a suitable solvent such as dichloromethane in the presence of a base such as potassium carbonate. The reaction can be carried out at ambient temperature.

In step (2) of Reaction Scheme IV, the trimethylsilyl group of the pyrazole of Formula XXXIX is removed to provide the pyrazole of Formula XL. Potassium carbonate in methanol or tetrabutylammonium fluoride in tetrahydrofuran can be used to carry out the transformation.

In step (3) of Reaction Scheme IV, the acetylene of the pyrazole of Formula XL is alkylated using conventional synthetic methods, Jacobs, T. L. in *Organic Reactions,* 5, 1, (1949), to provide a pyrazole of Formula XLI. The reaction can be carried out by deprotonation of the compound of Formula XL with a base and reaction of the resulting carbanion with an electrophile of Formula $R_{B1}$-Halide, for example, iodomethane. Step (3) can be omitted when $R_{B1}$ is hydrogen.

For some embodiments, steps (1) through (3) of Reaction Scheme IV may be replaced with one step from the iodo analog using a Sonogashira coupling reaction. The coupling can be carried out by combining an alkyne of Formula $R_{B1}$—C≡C—H, copper(I) iodide, dichlorobis(triphenylphosphine)palladium(II), and triethyl amine in a suitable solvent such as acetonitrile and then heating at an elevated temperature, such as the reflux temperature of the solvent.

In step (4) of Reaction Scheme IV, a pyrazole of Formula XLI reacts with ammonia to provide a pyrazolo[3,4-c]pyridin-4-amine of Formula XLII. The reaction can be carried out by adding a solution of ammonia in methanol to the pyrazole of Formula XLI and heating at an elevated temperature, such as 150° C. The reaction may be carried out in a pressure vessel.

Steps (5) and (6) may be carried out to provide a compound of Formula XLIV in which $R_{A1}$ is other than hydrogen. In step (5) of Reaction Scheme IV, a pyrazolo[3,4-c]pyridin-4-amine of Formula XLII is brominated under conventional bromination conditions to provide a bromo-substituted pyrazolo[3,4-c]pyridine-4-amine of Formula XLIII. The reaction can be carried out as described in step (5) of Reaction Scheme III.

In step (6) of Reaction Scheme IV, a bromo-substituted pyrazolo[3,4-c]pyridin-4-amine of Formula XLIII undergoes a transition metal catalyzed coupling reaction with a reagent of Formula $R_{A1}$-M, where $R_{A1}$ is alkenyl, alkoxy, and —N(R_9)_2 to provide a pyrazolo[3,4-c]pyridine-4-amine of Formula XLIV. Reagents of Formula $R_{A1}$-M, where M is, for example, —B(OH)_2, —B(O-alkyl)_2, —Sn(alkyl)_3, and —Zn-Halide, are known to undergo coupling reactions. The transformation can be carried out by first protecting the amino group of the compound of Formula XLIII, treating the protected compound with a reagent of Formula $R_{A1}$-M in the presence of a transition metal catalyst using conditions described in step (6) of Reaction Scheme III, and deprotecting the amine to provide the pyrazolo[3,4-c]pyridin-4-amine of Formula XLIV, which is a subgenus of Formula II. Alternatively, step (6) can be carried out by coupling a compound of Formula XLIII with an alkyne under Sonogashira conditions as described in step (1) of this reaction scheme. The resulting alkyne can be reduced under conventional hydrogenation conditions to provide a compound of Formula XLIV, where $R_{A1}$ is alkenyl or alkyl. Step (6) may also be carried out by (i) protecting the amino group of the compound of Formula XLIII, for example, with a Boc group; (ii) performing a lithium-halogen exchange; (iii) treating with an electrophile of the Formula $R_{A1}$-Halide, for example iodomethane; and (iv) deprotecting the amine to provide a compound of Formula XLIV.

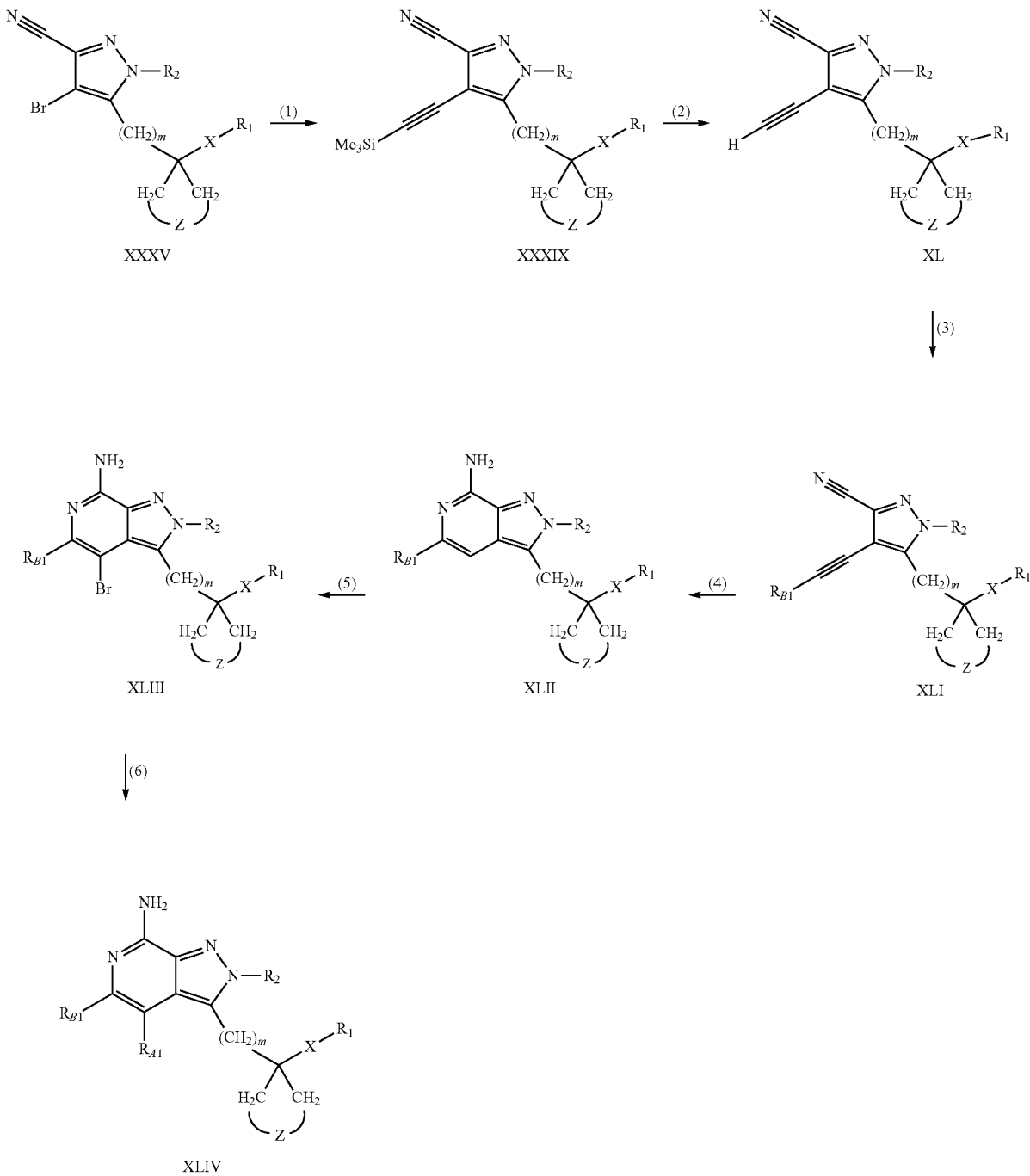

For some embodiments, compounds of the invention can be prepared according to Reaction Scheme V, where $R_{1b}$ and $R_{2b}$, are subsets of $R_1$ and $R_2$ as defined above that do not include those substituents which would be susceptible to reduction under the acidic hydrogenation conditions of the reaction and R, X, Z, and n are as defined above.

In Reaction Scheme V, a pyrazolo[3,4-c]quinoline of Formula XLV is reduced to provide a 6,7,8,9-tetrahydro-2H-pyrazolo[3,4-c]quinoline of Formula XLVI, which is a subgenus of Formula IV. The reaction may be carried out under heterogeneous hydrogenation conditions by adding platinum (IV) oxide to a solution or suspension of a pyrazolo[3,4-c]quinoline of Formula XLV in a suitable solvent such as trifluoroacetic acid and placing the reaction under hydrogen pressure.

Alternatively, the reduction may be carried out at an earlier stage in the synthetic pathway.

Reaction Scheme V

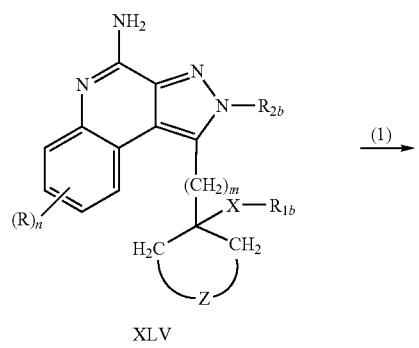

XLV

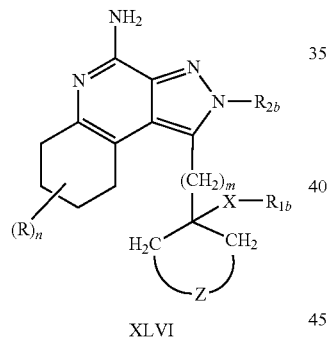

XLVI

Pyrazolo[3,4-c]naphthyridines of the invention can be prepared by using an azaindole as the starting material in Reaction Scheme I. Azaindoles are known compounds. Some are commercially available and others can be prepared using known synthetic methods. Alternatively, pyrazolo[3,4-c]naphthyridines of the invention can be prepared by using an aminopyridine boronic acid in Reaction Scheme III. Aminopyridine boronic acids can be prepared using known methods, for example, by directed ortho metalation of Boc-protected aminopyridines and subsequent electrophilic substitution. Alternatively, for some isomers, halogen-lithium exchange and subsequent electrophilic substitution can be used. For example, halogen-lithium exchange can be carried out on a 2-bromopyridine that has a protected amino group in the 3-position; subsequent electrophilic substitution with tributyltin chloride and deprotection of the amino group provides 3-amino-2-tri-n-butylstannylpyridine.

6,7,8,9-Tetrahydro-2H-pyrazolo[3,4-c]naphthyridines can be prepared by reducing pyrazolo[3,4-c]naphthyridines using the method of Reaction Scheme V.

For some embodiments, compounds can be further elaborated using conventional synthetic methods. For example, as shown in Scheme VI, a compound of Formula XLVII, can undergo acid mediated cleavage of the Boc group in step (1) to give a secondary amine that can be functionalized in step (2) with an acid chloride of Formula $R_4C(O)Cl$, an acid anhydride of Formula $(R_4C(O))_2O$, an alkyl chloroformate of Formula $R_4OC(O)Cl$, a sulfonyl chloride of Formula $R_4S(O)_2Cl$, a sulfonic anhydride of Formula $(R_4S(O)_2)_2O$, an isocyanate of formula $R_4NCO$, or an isothiocyanate of formula $R_4NCS$ to provide a compound of Formula XLIX where $R_4$ is defined as above and Q is —C(O)—, —C(O)O—, —S(O)$_2$—, —C(O)NH—, or —C(S)NH—. Numerous acid chlorides, alkyl chloroformates, sulfonyl chlorides, sulfonic anhydrides, isocyanates, and isothiocyanates are commercially available; others can be prepared readily using known synthetic methods. The reaction can be conveniently carried out by adding the acid chloride, alkyl chloroformate, sulfonyl chloride, sulfonic anhydride, isocyanate, or isothiocyanate to a solution or suspension of an amine of Formula XLVIII, in a suitable solvent such as chloroform. The reaction can be carried out at ambient temperature.

In addition, a compound of Formula XLVIII in Reaction Scheme VI can undergo alkylation of the secondary amine. In step (3) the compound of Formula XLVIII may be reacted with aldehydes, alkyl halides or triflates to provide a compound Formula L in which $R_8$ is defined as above. For example, treatment of a compound of Formula XLVIII with aqueous formaldehyde and a reducing agent such as sodium cyanoborohydride in an appropriate solvent such as methanol yields a compound of Formula L, where $R_8$ is a methyl group.

Reaction Scheme VI

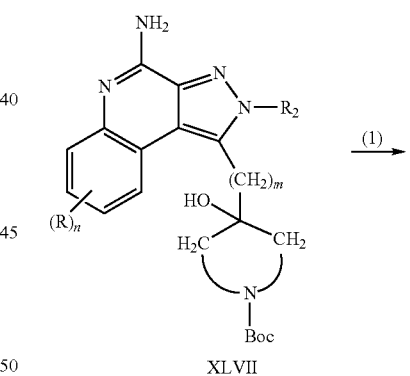

XLVII

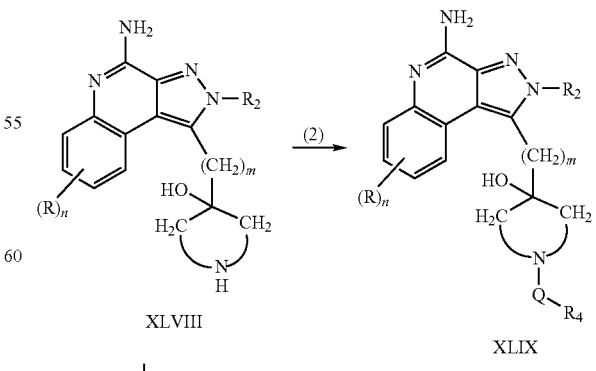

XLVIII

XLIX

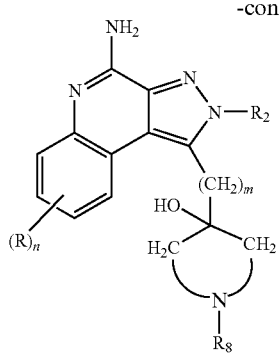

L

Intermediates of Formula LIII can be prepared according to Reaction Scheme VII, where $R_1$, X, and Z are as defined above.

In step (1) of Reaction Scheme VII, a ketone of the Formula LI is reacted with diethyl (2-oxopropyl)phosphonate to provide an olefin of Formula LII. The reaction can be carried out by adding a ketone of Formula LI and diethyl (2-oxopropyl) phosphonate to a solution of a base, such as potassium hydroxide, in a suitable solvent or solvent mix such as ethanol and water. The reaction can be carried out at a sub-ambient temperature such as 0° C.

In step (2) of Reaction Scheme VII, an olefin of Formula LII is derivatized using conventional methods. A compound of Formula LII where X is a bond and $R_1$ is hydrogen can be prepared by reducing the olefin using conventional heterogeneous hydrogenation conditions. Also, a compound of Formula LII can be treated with pivalonitrile in the presence of titanium tetrachloride; the resulting nitrile-substituted compound can be converted by convention methods to a compound of Formula LIII where X is a bond and $R_1$ is —C(O)—$NH_2$. A compound of Formula LII can also be treated with ammonium hydroxide followed by di-tert-butyl dicarbonate to provide a compound of Formula LIII where X is a bond and $R_1$ is —NHBoc, which can be deprotected and treated according to the methods of Reaction Scheme VI to provide a variety of other compounds.

Reaction Scheme VII

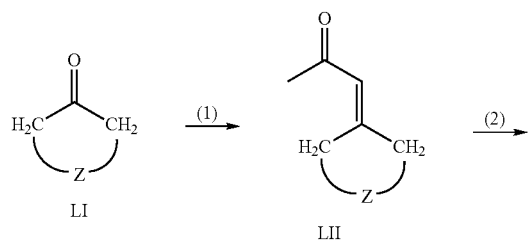

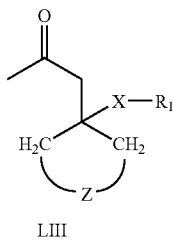

LIII

For some embodiments, compounds of the invention can be prepared according to Reaction Scheme VIII, where $R_{A2}$, $R_{B2}$, $R_2$, and Z are as defined above.

In step (1) of Reaction Scheme VIII, an olefin of Formula LII is condensed with diethyl oxalate to provide a ketoester of Formula LIV. The reaction can be carried out as described in step (1) of Reaction Scheme III.

In step (2) of Reaction Scheme VIII, a ketoester of Formula LIV reacts with a hydrazine of Formula $R_2NHNH_2$ to provide a pyrazole carboxylate of Formula LV. The reaction can be carried out as described in step (2) of Reaction Scheme III.

In step (3) of Reaction Scheme VIII, a pyrazole carboxylate of Formula LV is converted to a pyrazole carboxamide of Formula LVI. The reaction can be carried out as described in step (3) of Reaction Scheme III.

In step (4) of Reaction Scheme VIII, the olefinic bond in a compound of Formula LVI is oxidized to provide an epoxide of Formula LVII. The reaction can be carried out by treating a suspension of a compound of Formula LVI in a suitable solvent such as chloroform with 3-chloroperoxybenzoic acid. The reaction can be carried out at ambient temperature.

In step (5) of Reaction Scheme VIII, the epoxide ring in a compound of Formula LVII is cleaved to provide a hydroxy substituted pyrazole carboxamide of Formula LVIII. The reaction can be carried out by treating a solution of a compound of Formula LVII in a suitable solvent such as ethanol with palladium on carbon and ammonium formate. The reaction can be carried out at ambient temperature.

In step (6) of Reaction Scheme VIII, a pyrazole carboxamide of Formula LVIII is dehydrated to a pyrazole carbonitrile of Formula LIX. The reaction can be carried out as described in step (4) of Reaction Scheme III.

In steps (7) through (9) of Reaction Scheme VIII, a pyrazole carbonitrile of Formula LIX is converted to a pyrazolo[3,4-c]quinoline or pyrazolo[3,4-c]naphthyridine of Formula LX. The conversion can be carried out using the methods described in steps (5) through (7) of Reaction Scheme III.

Reaction Scheme VIII

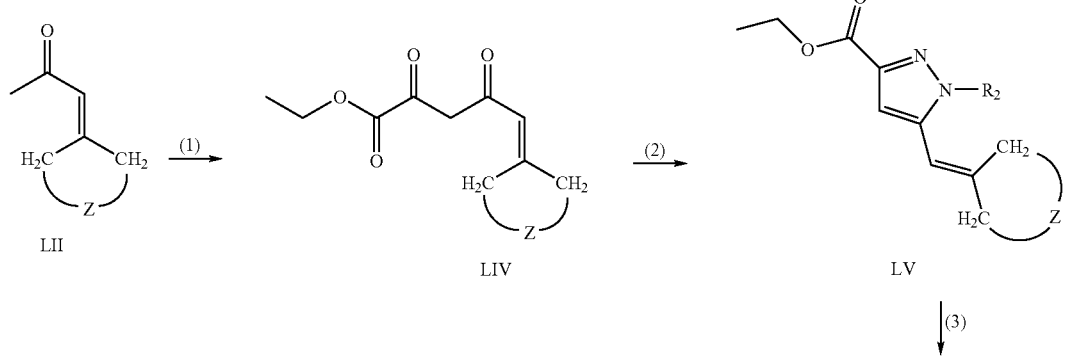

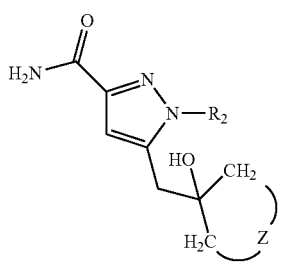 LVIII

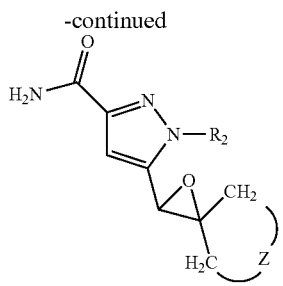 LVII

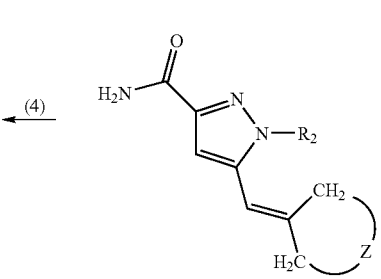 LVI

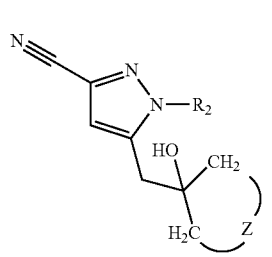 LIX

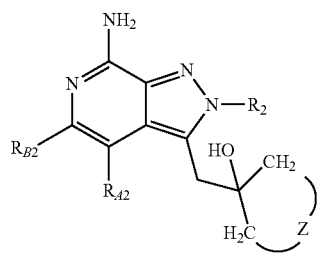 LX

For some embodiments, compounds of the invention can be prepared according to Reaction Scheme IX, where $R_{A2}$, $R_{B2}$, $R_2$, and Z are as defined above.

In step (1) of Reaction Scheme IX, the hydroxy group in a pyrazolo carbonitrile of Formula LIX is replaced with a fluoro group to provide a pyrazolo carbonitrile of Formula LXI. The reaction can be carried out by treating a solution of a compound of Formula LIX in a suitable solvent such as dichloromethane with [bis(2-methoxyethyl)amino]sulfur trifluoride. The trifluoride is added in a controlled fashion at a sub-ambient temperature such as 0° C.

In steps (2) through (4) of Reaction Scheme IX, a pyrazole carbonitrile of Formula LXI is converted to a pyrazolo[3,4-c]quinoline or pyrazolo[3,4-c]naphthyridine of Formula LXII. The conversion can be carried out using the methods described in steps (5) through (7) of Reaction Scheme III.

Reaction Scheme IX

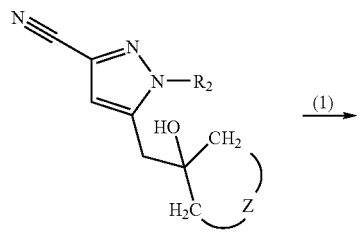 LIX

-continued

LXI

LXII

Compounds of the invention can also be prepared using variations of the routes shown in Reaction Schemes I through IX that would be apparent to one of skill in the art. For example, a compound of Formula LII wherein Z is —N(Boc)- can be readily prepared from 1-Boc-4-piperidinone according to the method of step (1) of Reaction Scheme VII. Steps (1) through (6) of Reaction Scheme VIII can then be used to prepare a compound of Formula LIX wherein Z is —N(Boc)-. The Boc group can then be cleaved and the resulting amine can be treated with an acid chloride, alkyl chloroformate, sulfonyl chloride, sulfonic anhydride, isocyanate, or isothio cyanate according to the methods described in steps (1) and (2) of Reaction Scheme VI. These Boc removal and amine functionalization steps can conveniently be carried out after the bromination in step (7) of Reaction Scheme VIII or after steps (1) and (2) of Reaction Scheme IX. Finally, the coupling and ring-closing methods of steps (8) and (9) of Reaction Scheme VIII or steps (3) and (4) of Reaction Scheme IX can be used to provide compounds of Formulas LX and LXII, respectively, wherein Z is —N(Q-$R_4$)—.

For some embodiments, compounds of the invention can be prepared according to Reaction Scheme X, where $R_1$, $R_2$, $R_A$, $R_B$, $G_1$, Z, and m are as defined above. The amino group of a pyrazolo compound of Formula I can be converted by conventional methods to a functional group such as an amide, carbamate, urea, amidine, or another hydrolyzable group. A compound of this type can be made by the replacement of a hydrogen atom in the amino group with a group such as —C(O)—R', α-aminoacyl, α-aminoacyl-α-aminoacyl, —C(O)—O—R', —C(O)—N(R")—R', —C(=NY')—R', —CH(OH)—C(O)—OY', —CH(O$C_{1-4}$ alkyl)$Y_0$, —$CH_2Y_1$, or —CH($CH_3$)$Y_1$; wherein R' and R" are each independently $C_{1-10}$ alkyl, $C_{3-7}$ cycloalkyl, phenyl, or benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$; with the proviso that R" may also be hydrogen; each α-aminoacyl group is independently selected from racemic, D, or L-amino acids; Y' is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N—$C_{1-6}$ alkylamino$C_{1-4}$ alkylenyl, or di-N,N—$C_{1-6}$ alkylamino$C_{1-4}$ alkylenyl; and $Y_1$ is mono-N—$C_{1-6}$ alkylamino, di-N,N—$C_{1-6}$ alkylamino, morpholin-4-yl, piperidin-1-yl, pyrrolidin-1-yl, or 4-$C_{1-4}$ alkylpiperazin-1-yl. Particularly useful compounds of Formula XIII are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at room temperature.

Reaction Scheme X

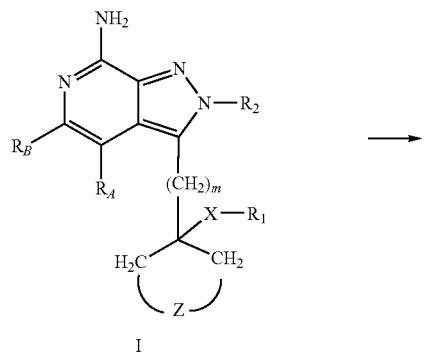

I

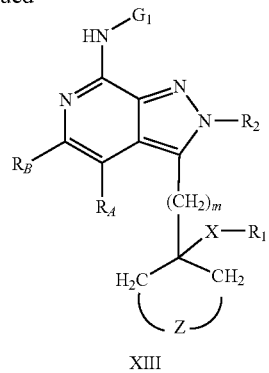

XIII

For some embodiments, compounds of the invention can be prepared according to Reaction Scheme XI, where $R_2$, $R_A$, $R_B$, $G_2$, Z, and m are as defined above. The hydrogen atom of the alcohol group of Formula LXIII can be replaced using conventional methods with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D, and L-amino acids. Particularly useful compounds of Formula XIV are esters made from carboxylic acids containing one to six carbon atoms, unsubstituted or substituted benzoic acid esters, or esters made from naturally occurring amino acids.

Reaction Scheme XI

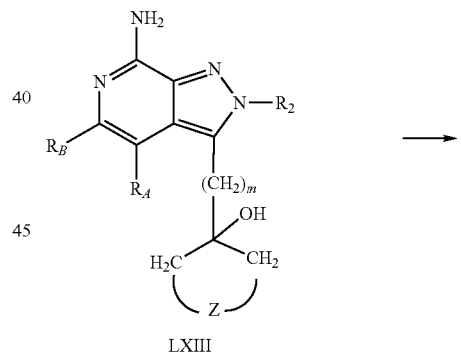

LXIII

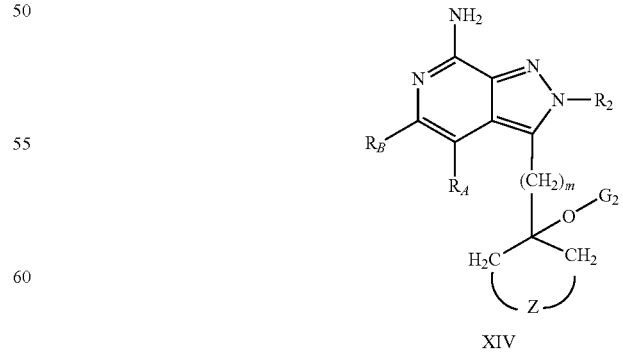

XIV

For some embodiments, compounds of the invention can be prepared using the synthetic routes described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α(TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type I ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below automated flash chromatography on silica gel was carried out using a HORIZON HPFC system (an automated high-performance flash purification product available from Biotage, Inc, Charlottesville, Va., USA) or an INTELLIFLASH Flash Chromatography System (an automated flash purification system available from AnaLogix, Inc, Burlington, Wis., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

1-[(4-Amino-2-propyl-2H-pyrazolo[3,4-c]quinolin-1-yl)methyl]cyclobutanol

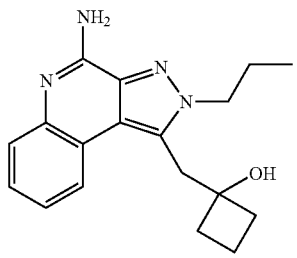

Part A

A solution of ethyl chlorooxoacetate (22.53 g, 0.165 mol) in diethyl ether (100 mL) was added over a period of 15 minutes to a cooled (0° C.) solution of 2-methylindole (19.7 g, 0.15 mol) and pyridine (14.2 g, 0.18 mol) in diethyl ether (200 mL). The reaction was stirred for two hours at 0° C. under a nitrogen atmosphere. Most of the diethyl ether had evaporated by the end of the two-hour reaction time, and a solid was present. Water (100 mL) was added, and the solid was isolated by filtration and washed with 1:1 diethyl ether/hexane. The solid (27.9 g) was then dissolved in boiling toluene (250 mL) and recrystallized upon cooling to 6° C. The crystals were isolated by filtration, washed with toluene, dried for two hours on the vacuum filter funnel, triturated with water at 75° C. for five minutes, isolated by filtration, and dried for three hours on the filter funnel to provide 17.8 g ethyl (2-methyl-1H-indol-3-yl)(oxo)acetate of as a rust-colored powder.

Part B

Ethyl (2-methyl-1H-indol-3-yl)(oxo)acetate (6.94 g, 30.0 mmol) and propylhydrazine oxalate (10.8 g, 66.0 mmol) were added to a solution of acetyl chloride (5.18 g, 66.0 mmol) in acetic acid (5 mL) and ethanol (150 mL), and the reaction was heated at reflux under nitrogen for 42.5 hours. The ethanol was removed under reduced pressure, and 2 M aqueous sodium carbonate was added. The mixture was stirred, and the resulting solid was isolated by filtration, washed with water, and dried for 90 minutes on the vacuum filter funnel to provide a dark semi-solid. The crude product was stirred with tert-butyl methyl ether (50 mL) and isolated by filtration, washed with tert-butyl methyl ether, and dried on the vacuum filter funnel to provide 6.10 g of an orange solid, which was stirred with boiling acetonitrile (50 mL), isolated by filtration, and purified by automated flash chromatography to provide 5.11 g of 1-methyl-2-propyl-2H-pyrazolo[3,4-c]quinolin-4-ol as a white solid.

Part C

A solution of 1-methyl-2-propyl-2H-pyrazolo[3,4-c]quinolin-4-ol (5.11 g, 21.2 mmol) in phosphorus oxychloride (50 mL) was heated at reflux for 30 minutes, allowed to cool to room temperature, and stirred for two days. The reaction mixture was poured into ice water (500 mL) with stirring, and concentrated ammonium hydroxide (169 mL) and ice were added. A solid was present and was isolated by filtration, washed with water, and purified by automated flash chromatography (eluting with 5% to 25% CMA in chloroform). The resulting orange solid (5.5 g) was recrystallized from acetonitrile (25 mL). The crystals were washed with acetonitrile and dried for five hours to provide 3.85 g of 4-chloro-1-methyl-2-propyl-2H-pyrazolo[3,4-c]quinoline as a white solid, mp 145-147° C.

Anal. Calcd for $C_{14}H_{14}N_3Cl$: C, 64.74; H, 5.43; N, 16.18. Found: C, 64.50; H, 5.64; N, 16.20.

This product was combined with material from another run.

Part D

A Parr vessel was charged with 4-chloro-1-methyl-2-propyl-2H-pyrazolo[3,4-c]quinoline (4.31 g) and a solution of ammonia in methanol (50 mL of 7 N). The reaction was heated at 150° C. for 24 hours and allowed to cool to room temperature. Most of the methanol was removed under reduced pressure, and water was added. A precipitate formed and was isolated by filtration, washed with water, and dried on the vacuum filter funnel to provide 3.8 g of 1-methyl-2-propyl-2H-pyrazolo[3,4-c]quinolin-4-amine as a white solid.

Part E

A solution of 1-methyl-2-propyl-2H-pyrazolo[3,4-c]quinolin-4-amine (3.78 g, 15.7 mmol), di-tert-butyl dicarbonate (8.6 g, 39.3 mmol), and 4-dimethylaminopyridine (DMAP) (96 mg, 0.79 mmol) in tetrahydrofuran (THF) (100 mL) was heated at reflux for 14 hours and allowed to cool to room temperature. The THF was removed under reduced pressure, and the residue was purified by chromatography using a HORIZON HPFC system (eluting with 50% ethyl acetate in hexane) followed by recrystallization from tert-butyl methyl ether/hexane. The crystals were washed with hexane and dried on the vacuum filter funnel for two hours to provide 6.46 g of di(tert-butyl) 1-methyl-2-propyl-2H-pyrazolo[3,4-c]quinolin-4-ylimidodicarbonate as an off-white solid.

Part F

A solution of di(tert-butyl) 1-methyl-2-propyl-2H-pyrazolo[3,4-c]quinolin-4-ylimidodicarbonate (1.32 g, 3.00 mmol) in anhydrous tetrahydrofuran (THF) (30 mL) was cooled to −78° C. under an argon atmosphere. tert-Butyllithium (7.06 mL of a 1.7 M solution in pentane) was added over a period of eight minutes, and the resulting dark-colored solution was stirred at −78° C. for 40 minutes. Cyclobutanone (1.05 g, 15 mmol) was added over a period of two minutes, and the −78° C. bath was replaced with a 0° C. bath. The reaction mixture was stirred for 10 minutes, and then saturated aqueous ammonium chloride (30 mL) was added. The aqueous layer was separated and extracted three times with tert-butyl methyl ether, and the combined organic fractions were dried over magnesium sulfate, filtered, and concentrated under reduced pressure. The residue (1.3 g) was purified by automated flash chromatography and then boiled in 2 M hydrochloric acid for 30 minutes. The solution was allowed to cool to room temperature overnight and then made basic with the addition of 2 M aqueous sodium carbonate. The resulting solution was extracted four times with chloroform, and the combined extracts were dried over magnesium sulfate, filtered, and concentrated under reduced pressure. The residue (1.2 g) was purified twice by automated flash chromatography and recrystallized from acetonitrile to provide 297 mg of 1-[(4-amino-2-propyl-2H-pyrazolo[3,4-c]quinolin-1-yl)methyl]cyclobutanol as a white solid, mp 191-193° C.

MS (APCI) m/z 311 (M+H)$^+$;

Anal. Calcd for $C_{18}H_{22}N_4O$: C, 69.65; H, 7.14; N, 18.05. Found: C, 69.35; H, 7.14; N, 18.11.

Example 2

4-[(4-Amino-2-propyl-2H-pyrazolo[3,4-c]quinolin-1-yl)methyl]tetrahydro-2H-pyran-4-ol

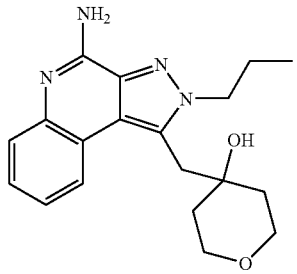

A solution of di(tert-butyl) 1-methyl-2-propyl-2H-pyrazolo[3,4-c]quinolin-4-ylimidodicarbonate (1.32 g, 3.00 mmol) in anhydrous tetrahydrofuran (THF) (30 mL) was cooled to −78° C. under an argon atmosphere. tert-Butyllithium (4.4 mL of a 1.7 M solution in pentane) was added over a period of five minutes, and the resulting dark-colored solution was stirred at −78° C. for 30 minutes. Tetrahydro-4H-pyran-4-one (901 mg, 9.0 mmol) was added, and reaction mixture was stirred for 10 minutes. The −78° C. bath was replaced with a 0° C. bath, and then saturated aqueous ammonium chloride (30 mL) was added. The aqueous layer was separated and extracted three times with tert-butyl methyl ether, and the combined organic fractions were dried over magnesium sulfate, filtered, and concentrated under reduced pressure. The residue (1.3 g) was purified by automated flash chromatography (eluting with ethyl acetate) and heated in refluxing 1 M hydrogen chloride in ethanol (50 mL) for one hour. The solution was allowed to cool to room temperature and then made basic with the addition of 2 M aqueous sodium carbonate. The resulting solution was extracted four times with chloroform, and the combined extracts were dried over magnesium sulfate, filtered, and concentrated under reduced pressure. The residue (1.2 g) was purified by automated flash chromatography and recrystallized from acetonitrile to provide 430 mg of 4-[(4-amino-2-propyl-2H-pyrazolo[3,4-c]quinolin-1-yl)methyl]tetrahydro-2H-pyran-4-ol as a white solid, mp 209-211° C.

MS (APCI) m/z 341 (M+H)$^+$;
Anal. Calcd for $C_{19}H_{24}N_4O_2$: C, 67.04; H, 7.11; N, 16.46. Found: C, 66.98; H, 7.17; N, 16.39.

Example 3

2-Propyl-1-(tetrahydro-2H-pyran-4-ylmethyl)-2H-pyrazolo[3,4-c]quinolin-4-amine

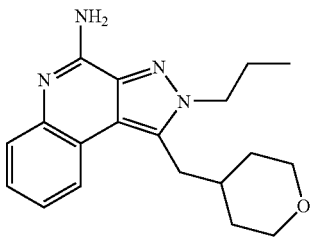

Part A

A solution of potassium hydroxide (4.66 g, 83.1 mmol) in ethanol (181 mL) and water (45 mL) was cooled to approximately 0° C. Tetrahydro-4H-pyran-4-one (7.56 g, 75.5 mmol) and diethyl (2-oxopropyl)phosphonate (16.1 g, 83.1 mmol) were sequentially added. The reaction was allowed to warm to room temperature and stirred for five hours. The reaction mixture was washed with brine and the organic layer was separated. The aqueous layer was extracted three times with tert-butyl methyl ether. The combined organic fractions were dried over magnesium sulfate, filtered, and concentrated under reduced pressure. The residue was dissolved in a mixture of 20% ethyl acetate in hexane and chloroform, dried again over magnesium sulfate, filtered, concentrated under reduced pressure, and purified by automated flash chromatography (eluting with 35% to 45% ethyl acetate in hexane). The resulting colorless oil was dried under a stream of nitrogen to provide 8.03 g of 1-tetrahydro-4H-pyran-4-ylideneacetone.

Part B

A solution of 1-tetrahydro-4H-pyran-4-ylideneacetone (4.0 g, 28.5 mmol) in ethyl acetate was added to a Parr vessel. The vessel was purged with nitrogen, and 10% palladium on carbon (400 mg) was added. The vessel was shaken under hydrogen pressure (50 psi, $3.4 \times 10^5$ Pa) for approximately ten minutes, and the reaction mixture was filtered through a layer of CELITE filter agent. The filter cake was washed with ethyl acetate. The filtrate was concentrated under reduced pressure, and the residue was dried under a stream of nitrogen to provide 3.80 g of 1-tetrahydro-2H-pyran-4-ylacetone as a colorless oil.

Part C

A neat mixture of 1-tetrahydro-2H-pyran-4-ylacetone (3.80 g, 26.7 mmol) and diethyl oxalate (4.30 g, 29.4 mmol) was added in one portion, followed by an ethanol rinse (10 mL), to a stirred solution of sodium tert-butoxide (2.83 g, 29.4 mmol) in ethanol (20 mL). The mixture was stirred for one hour, cooled to approximately 0° C., and treated with acetic acid (30.0 mL). After the mixture was stirred for five minutes, propylhydrazine oxalate (4.38 g, 26.7 mmol) was added in one portion. The reaction was allowed to warm to room temperature slowly and stirred overnight. Most of the volatiles were removed under reduced pressure, and 2 M aqueous sodium carbonate was added. The mixture was extracted four times with tert-butyl methyl ether. The organic layers were combined, dried over magnesium sulfate, filtered, and concentrated to yield 8.5 g of a yellow oil. The oil was purified twice by automated flash chromatography (eluting with ethyl acetate in hexane), and the resulting pale yellow oil was dried under a stream of nitrogen to provide 6.43 g of ethyl 1-propyl-5-(tetrahydro-2H-pyran-4-ylmethyl)-1H-pyrazole-3-carboxylate.

Part D

Lithium hydroxide monohydrate (3.8 g, 92 mmol) was added to a solution of ethyl 1-propyl-5-(tetrahydro-2H-pyran-4-ylmethyl)-1H-pyrazole-3-carboxylate (6.43 g, 22.9 mmol) in methanol (30 mL) and water (10 mL). The mixture was stirred for 20 hours. Most of the volatiles were removed under reduced pressure, and water (100 mL) and acetic acid (52 mL, 910 mmol) were sequentially added. The solution was cooled to approximately 0° C. After five minutes, a white solid formed, and more water (100 mL) was added. The mixture was stirred for 30 minutes, and the solid was isolated by filtration, washed with water, and dried on the vacuum filter funnel to provide 4.88 g of 1-propyl-5-(tetrahydro-2H-pyran-4-ylmethyl)-1H-pyrazole-3-carboxylic acid as a white solid.

Part E 1-(3-Dimethylaminopropyl)-3-ethylcarbodiimide hydrochloride (4.06 g, 21.2 mmol) was added to a solution of 1-propyl-5-(tetrahydro-2H-pyran-4-ylmethyl)-1H-pyrazole-3-carboxylic acid (4.88 g, 19.3 mmol) and 1-hydroxybenzotriazole (2.87 g, 21.2 mmol) in N,N-dimethylformamide (DMF) (24.4 mL) at room temperature. The mixture was stirred for two hours, cooled in an ice bath, and treated with concentrated ammonium hydroxide (3.9 mL). A precipitate formed, and the mixture was stirred 30 minutes at 0° C. Water (100 mL) was added, and the mixture was stirred for an additional ten minutes. The precipitate was isolated by filtration, washed with water, and dried on the vacuum filter funnel to provide 4.05 g of 1-propyl-5-(tetrahydro-2H-pyran-4-ylmethyl)-1H-pyrazole-3-carboxamide as white crystals.

Part F

A solution of trifluoroacetic anhydride (2.50 mL, 17.7 mmol) in dichloromethane (32 mL) was added over a period of ten minutes to a 0° C. solution of 1-propyl-5-(tetrahydro-2H-pyran-4-ylmethyl)-1H-pyrazole-3-carboxamide (4.05 g, 16.1 mmol) and triethylamine (4.89 g, 48.3 mmol) in dichloromethane (32 mL). After the addition was complete, the cooling bath was removed and the solution was stirred for three hours. The solution was washed with 2 M aqueous sodium carbonate. The aqueous layer was extracted three times with tert-butyl methyl ether. The organic layers were combined, dried over magnesium sulfate, filtered, and concentrated under reduced pressure. The crude product was purified by automated flash chromatography (eluting with 40% to 70% ethyl acetate in hexane) to provide 3.98 g of 1-propyl-5-(tetrahydro-2H-pyran-4-ylmethyl)-1H-pyrazole-3-carbonitrile as a pale yellow oil.

Part G

Potassium acetate (3.93 g, 40.0 mmol) and bromine (3.58 g, 22.4 mmol) were sequentially added to a solution of 1-propyl-5-(tetrahydro-2H-pyran-4-ylmethyl)-1H-pyrazole-3-carbonitrile (3.98 g, 16 mmol) in acetic acid (32 mL). The reaction was stirred for 40 hours at room temperature. Saturated aqueous sodium hydrogensulfite was added until the reaction became colorless. Most of the acetic acid was removed under reduced pressure, and 2M aqueous sodium carbonate was added. A precipitate formed, was isolated by filtration, washed with water, and dried on the vacuum filter funnel to provide 4.91 g of 4-bromo-1-propyl-5-(tetrahydro-2H-pyran-4-ylmethyl)-1H-pyrazole-3-carbonitrile as a white solid.

Part H

2-Aminophenylboronic acid hydrochloride (1.39 g, 8.0 mmol) and dichlorobis(triphenylphosphine)palladium(II) (140 mg, 0.20 mmol) were sequentially added to a mixture of 4-bromo-1-propyl-5-(tetrahydro-2H-pyran-4-ylmethyl)-1H-pyrazole-3-carbonitrile (1.25 g, 4.00 mmol), potassium carbonate (1.82 g, 13.2 mmol), 1,2-dimethoxyethane (DME) (15 mL), and water (7.5 mL). The flask was placed under vacuum and back-filled with nitrogen four times. The reaction was heated under a nitrogen atmosphere at 95° C. for one hour. The reaction was allowed to cool to room temperature, and water and tert-butyl methyl ether were added. The aqueous layer was separated and extracted with tert-butyl methyl ether three times. The organic fractions were combined, dried over magnesium sulfate, filtered, and concentrated to yield a brown solid (1.75 g). The crude product was purified by automated flash chromatography (eluting with ethyl acetate in hexane) to provide 1.10 g of 4-(2-aminophenyl)-1-propyl-5-(tetrahydro-2H-pyran-4-ylmethyl)-1H-pyrazole-3-carbonitrile as a pale orange solid.

Part I

Acetyl chloride (50 mmol) was stirred with anhydrous ethanol (50 ml), and the resulting solution was added to the material from Part H. The resulting solution was heated at reflux for 16 hours. Aqueous sodium carbonate (30 mL of 2 M) was added, and then most of the ethanol was removed under reduced pressure. Water was added; a solid was present and was isolated by filtration and washed with water. The crude product was purified by automated flash chromatography (eluting with 5% to 25% CMA in chloroform) followed by recyclization from ethyl acetate. The crystals were dried on the vacuum filter funnel for 2.5 hours to provide 853 mg of 2-propyl-1-(tetrahydro-2H-pyran-4-ylmethyl)-2H-pyrazolo[3,4-c]quinolin-4-amine as a white solid, mp 218-220° C.

MS (APCI) m/z 325 (M+H)$^+$;

Anal. Calcd for $C_{19}H_{24}N_4O$: C, 70.34; H, 7.46; N, 17.27. Found: C, 70.11; H, 7.72; N, 17.28.

Example 4

2-Propyl-1-(tetrahydro-2H-pyran-4-ylmethyl)-2H-pyrazolo[3,4-c][1,8]naphthyridin-4-amine

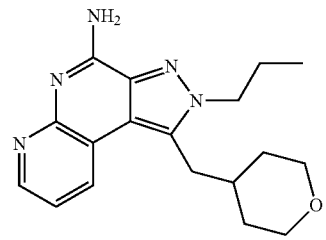

Part A tert-Butyl N-(2-pyridyl)carbamate is available from the literature procedure (Moraczewski, A. L. et al, *J. Org. Chem.*, 1998, 63, 7258) or can be prepared by the following method. Under a nitrogen atmosphere, sodium bis(trimethylsilyl)amide (225 mL of a 1.0 M solution in tetrahydrofuran) was added over a period of 20 minutes to a solution of 2-aminopyridine (10.61 g, 108.0 mmol) in dry THF (150 mL). The solution was stirred for 15 minutes and then cooled to 0° C. A solution of di-tert-butyl dicarbonate (24.60 g, 112.7 mmol) in THF (50 mL) was added slowly, and the reaction was allowed to warm to ambient temperature slowly and stirred overnight. The THF was removed under reduced pressure, and the residue was partitioned between ethyl acetate (500 mL) and 0.1 M hydrochloric acid (250 mL). The organic layer was separated; washed sequentially with 0.1 M hydrochloric acid (250 mL), water (250 mL), and brine (250 mL); dried over magnesium sulfate; filtered; and concentrated under reduced pressure. The crude product was purified by automated flash chromatography (eluting with 80:20 hexanes/ethyl acetate) to provide 17.43 g of tert-butyl N-(2-pyridyl)carbamate as a white solid.

Part B

Under a nitrogen atmosphere, a solution of tert-butyl N-(2-pyridyl)carbamate (15.71 g, 80.9 mmol) and N,N, N',N'-tetramethylethylenediamine (TMEDA) (25.3 g, 218 mmol) in THF (400 mL) was cooled to −78° C. n-Butyllithium (81 mL of a 2.5 M solution in hexanes) was added dropwise over a period of 20 minutes. The solution was stirred for ten minutes, and then the addition funnel was rinsed with additional THF (20 mL). The solution was warmed to −6° C., stirred for two hours, and cooled again to −78° C. Triisopropyl borate (57.7 g, 307 mmol) was added over a period of ten minutes. The resulting solution was warmed to 0° C. and then poured into saturated aqueous ammonium chloride (500 mL). A yellow solid formed and was stirred with diethyl ether (300 mL), isolated by filtration, washed with diethyl ether and water, and air-dried overnight to provide 2-tert-butoxycarbonylamino-3-pyridylboronic acid as a yellow solid.

Part C

Hydrochloric acid (10 mL of 1M) was added to a solution of 2-tert-butoxycarbonylamino-3-pyridylboronic acid (2.59 g, 10.9 mmol), and the resulting mixture was heated at 80° C. for 45 minutes and allowed to cool to room temperature. Potassium carbonate (3.87 g, 27.95 mmol) was added with stirring, and then DME (20 mL), 4-bromo-1-propyl-5-(tetrahydro-2H-pyran-4-ylmethyl)-1H-pyrazole-3-carbonitrile (1.70 g, 5.44 mmol), and dichlorobis(triphenylphosphine)palladium(II) (190 mg, 0.27 mmol) were added. The flask was placed under vacuum and back-filled with nitrogen three times. The reaction was heated under a nitrogen atmosphere at 95° C. overnight. The reaction was allowed to cool to room temperature, and the volatiles were removed under reduced pressure. The residue was dissolved in chloroform (100 mL), and the resulting solution was washed with water (100 mL), dried over magnesium sulfate, filtered, and concentrated to yield a light yellow solid. The crude product was purified by automated flash chromatography (eluting with 0% to 30% CMA in chloroform) followed by recrystallization from acetonitrile (30 mL). The crystals were washed with cold acetonitrile and dried overnight in a vacuum oven at 60° C. to provide 0.43 g of 2-propyl-1-(tetrahydro-2H-pyran-4-ylmethyl)-2H-pyrazolo[3,4-c][1,8]naphthyridin-4-amine as white needles, mp 252-255° C.

Anal. calcd for $C_{18}H_{23}N_5O$: C, 66.44; H, 7.12; N, 21.52. Found: C, 66.21; H, 7.35; N, 21.54.

Example 5

2-(2-Methoxyethyl)-1-(tetrahydro-2H-pyran-4-ylmethyl)-2H-pyrazolo[3,4-c]quinolin-4-amine

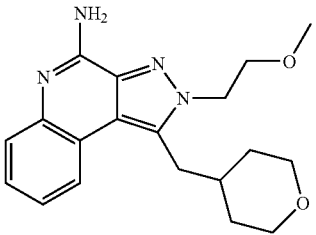

Part A

The method described in Part B of Example 3 was repeated with 1-tetrahydro-4H-pyran-4-ylideneacetone (4.0 g, 28.5 mmol), and the resulting 1-tetrahydro-2H-pyran-4-ylacetone was mixed with diethyl oxalate (4.66 g, 31.9 mmol) and added to a solution of sodium tert-butoxide (3.07 g, 31.9 mmol) in ethanol (22 mL). The reaction was carried out according to the method described in Part C of Example 3 with the following modifications. Hydroxyethylhydrazine (2.43 g, 31.9 mmol) was used instead of ethylhydrazine oxalate. Extractions were carried out seven times with chloroform, and the crude product was not purified. Ethyl 1-(2-hydroxyethyl)-5-(tetrahydro-2H-pyran-4-ylmethyl)-1H-pyrazole-3-carboxylate (8.2 g) was obtained as a viscous yellow oil.

Part B

A solution of the material from Part A in THF (50 mL) was cooled to approximately 0° C. under nitrogen, and iodomethane (4.12 g, 29 mmol) was added. Sodium hydride (1.16 g of 60% in mineral oil, 29 mmol) was added over a period of two minutes. The mixture was stirred at 0° C. for 20 minutes, allowed to warm to room temperature, and stirred overnight. Saturated aqueous ammonium chloride was added, and the mixture was extracted four times with tert-butyl methyl ether. The combined extracts were dried over magnesium sulfate, filtered, and concentrated under reduced pressure to provide 10 g of a yellow oil. The oil was purified by automated flash chromatography (eluting with ethyl acetate) to provide 5.20 g of ethyl 1-(2-methoxyethyl)-5-(tetrahydro-2H-pyran-4-ylmethyl)-1H-pyrazole-3-carboxylate as a pale yellow oil.

Part C

Lithium hydroxide monohydrate (2.94 g, 70.2 mmol) was added to a solution of ethyl 1-(2-methoxyethyl)-5-tetrahydro-2H-pyran-4-ylmethyl)-1H-pyrazole-3-carboxylate (5.2 g, 17.5 mmol) in methanol (60 mL) and water (20 mL). The mixture was stirred for overnight. Most of the volatiles were removed under reduced pressure, and acetic acid (40 mL) and water were added. The solution was cooled to approximately 0° C. and stirred for one hour. The volatiles were removed under reduced pressure, and the residue was partitioned between water and chloroform. The aqueous layer was separated and extracted four times with chloroform and then adjusted to pH 4 with the addition of 1 M hydrochloric acid. The aqueous fraction was extracted again four times with chloroform. The combined organic fractions were dried over magnesium sulfate and sodium sulfate, filtered, and concentrated under reduced pressure. The residue was twice dissolved in heptane and concentrated and twice dissolved in toluene and concentrated to provide 5.42 g of 1-(2-methoxyethyl)-5-(tetrahydro-2H-pyran-4-ylmethyl)-1H-pyrazole-3-carboxylic acid containing some toluene and 3 mol % acetic acid.

Part D 1-(3-Dimethylaminopropyl)-3-ethylcarbodiimide hydrochloride (3.69 g, 19.3 mmol) was added to a solution of the material from Part C and 1-hydroxybenzotriazole (2.61 g, 19.3 mmol) in DMF (27.1 mL) at room temperature. The mixture was stirred for one hour, cooled in an ice bath, and treated with concentrated ammonium hydroxide (3.5 mL). A precipitate formed, and the mixture was stirred 15 minutes at 0° C. Water (150 mL) was added, and the mixture was stirred. The precipitate was isolated by filtration, washed with water, and dried on the vacuum filter funnel to provide 1.44 g of 1-(2-methoxyethyl)-5-(tetrahydro-2H-pyran-4-ylmethyl)-1H-pyrazole-3-carboxamide as a white solid. The filtrate was extracted six times with chloroform, and the combined extracts were dried over sodium sulfate, filtered, and concentrated under reduced pressure. The residue was twice dissolved in xylenes and concentrated under reduced pressure and then recrystallized from a mixture of 50% ethyl acetate in hexane (50 mL) and ethyl acetate (150 mL). The crystals were dried overnight on the vacuum filter funnel to provide an additional 2.027 g of 1-(2-methoxyethyl)-5-(tetrahydro-2H-pyran-4-ylmethyl)-1H-pyrazole-3-carboxamide as white plates.

Anal. Calcd for $C_{13}H_{19}N_3O_3$: C, 58.41; H, 7.92; N, 15.72. Found: C, 58.52; H, 7.89; N, 15.86.

Part E

The method described in Part F of Example 3 was used to treat 1-(2-methoxyethyl)-5-(tetrahydro-2H-pyran-4-ylmethyl)-1H-pyrazole-3-carboxamide (3.41 g, 12.7 mmol) with trifluoroacetic anhydride (1.98 mL, 14.0 mmol) in the presence of triethylamine (3.86 g, 38.1 mmol) with the following modifications. Extractions were carried out four times with chloroform, and the automated flash chromatography column was eluted with ethyl acetate. 1-(2-Methoxyethyl)-5-(tetrahydro-2H-pyran-4-ylmethyl)-1H-pyrazole-3-carbonitrile (3.16 g) was obtained as a colorless oil.

Part F

Potassium acetate (3.12 g, 31.7 mmol) and bromine (2.84 g, 17.7 mmol) were sequentially added to a solution of 1-(2-methoxyethyl)-5-(tetrahydro-2H-pyran-4-ylmethyl)-1H-pyrazole-3-carbonitrile (3.16 g, 12.7 mmol) in acetic acid (25 mL). The reaction was stirred for 16 hours at room temperature. Saturated aqueous sodium hydrogensulfite was added until the reaction became colorless. Water was added, and a precipitate formed, was isolated by filtration, washed with water, and dried on the vacuum filter funnel to provide 3.78 g of 4-bromo-1-(2-methoxyethyl)-5-(tetrahydro-2H-pyran-4-ylmethyl)-1H-pyrazole-3-carbonitrile as a white solid containing about 2 mol % acetic acid.

Part G

Potassium carbonate (1.82 g, 13.2 mmol), 1,2-dimethoxyethane (DME) (15 mL), water (7.5 mL), and dichlorobis(triphenylphosphine)palladium(II) (140 mg, 0.20 mmol) were added to a mixture of 2-aminophenylboronic acid hydrochloride (1.39 g, 8.0 mmol) and 4-bromo-1-(2-methoxyethyl)-5-(tetrahydro-2H-pyran-4-ylmethyl)-1H-pyrazole-3-carbonitrile (1.31 g, 4.00 mmol). The flask was placed under vacuum and back-filled with nitrogen four times. The reaction was heated under a nitrogen atmosphere at 95° C. for 90 minutes. The aqueous layer was separated and extracted twice with tert-butyl methyl ether. The organic fractions were combined, dried over magnesium sulfate, filtered, and concentrated to yield a black oil (2.2 g). The crude product was purified by automated flash chromatography (eluting with ethyl acetate) to provide 1.14 g of 4-(2-aminophenyl)-1-(2-methoxyethyl)-5-(tetrahydro-2H-pyran-4-ylmethyl)-1H-pyrazole-3-carbonitrile as a yellow, waxy solid.

Part H

The method described in Part I of Example 3 was followed. Following recrystallization from ethyl acetate (40 mL), the crystals were dried on the vacuum filter funnel for 19 hours to provide 736 mg of 2-(2-methoxyethyl)-1-(tetrahydro-2H-pyran-4-ylmethyl)-2H-pyrazolo[3,4-c]quinolin-4-amine as white crystals, mp 189-190° C.

MS (APCI) m/z 341 (M+H)⁺;

Anal. Calcd for $C_{19}H_{24}N_4O_2$: C, 67.04; H, 7.11; N, 16.46. Found: C, 67.03; H, 7.22; N, 16.55.

Example 6

2-(2-Methoxyethyl)-1-(tetrahydro-2H-pyran-4-ylmethyl)-2H-pyrazolo[3,4-c][1,8]naphthyridin-4-amine

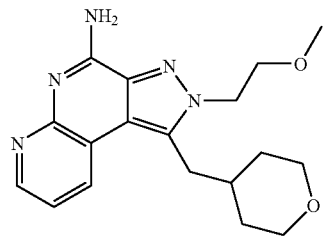

Hydrochloric acid (10 mL of 1M) was added to a solution of 2-tert-butoxycarbonylamino-3-pyridylboronic acid (2.59 g, 10.9 mmol), and the resulting mixture was heated at 80° C. for 45 minutes and allowed to cool to room temperature. Potassium carbonate (3.60 g, 26.0 mmol) was added with stirring, and then DME (20 mL), 4-bromo-1-(2-methoxyethyl)-5-(tetrahydro-2H-pyran-4-ylmethyl)-1H-pyrazole-3-carbonitrile (1.75 g, 5.33 mmol), and dichlorobis(triphenylphosphine)palladium(II) (190 mg, 0.27 mmol) were added. The reaction was carried out as described in Part C of Example 4. The crude product was purified by automated flash chromatography (eluting with 0% to 35% CMA in chloroform) followed by recrystallization from acetonitrile (30 mL) after hot filtration. The crystals were washed with cold acetonitrile and dried overnight in a vacuum oven at 60° C. to provide 0.13 g of 2-(2-methoxyethyl)-1-(tetrahydro-2H-pyran-4-ylmethyl)-2H-pyrazolo[3,4-c][1,8]naphthyridin-4-amine as light yellow needles, mp 230-233° C.

Anal. calcd for $C_{18}H_{23}N_5O_2$: C, 63.32; H, 6.79; N, 20.51. Found: C, 63.37; H, 6.84; N, 20.59.

Example 7

1-[(4-Fluorotetrahydro-2H-pyran-4-yl)methyl]-2-methyl-2H-pyrazolo[3,4-c]quinolin-4-amine

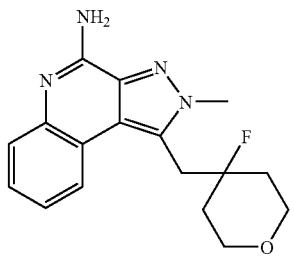

Part A

Diethyl 2-oxopropylphosphonate (12.8 mL, 1.1 eq) was added to a stirred solution of tetrahydropyran-4-one (6.06 g, 1.0 eq) in ethanol (148 mL) and then the mixture was cooled to 0° C. with an ice bath. A solution of potassium hydroxide (3.74 g, 1.1 eq) in water (38 mL) was added over a period of about 2 minutes. The ice bath was removed and the reaction mixture was stirred for 3 hours. The bulk of the ethanol was removed under reduced pressure while maintaining the temperature at ≦20° C. to provide about 32 g of a yellow liquid. The liquid was diluted with water (150 mL) and then extracted with dichloromethane (2×150 mL). The combined organics were dried over magnesium sulfate and then concentrated under reduced pressure while maintaining the temperature at ≦20° C. to provide 12.05 g of a pale yellow liquid. This material was purified by automated flash chromatography (eluting with 20% ethyl acetate in hexanes for 2 column volumes, with a gradient of 2040% ethyl acetate in hexanes over 5 column volumes, and with 40% ethyl acetate in hexanes for 2 column volumes) to provide 7.02 g of 1-tetrahydro-4H-pyran-4-ylideneacetone. Analysis by ¹H NMR indicated clean product with residual ethyl acetate (14%).

Part B

A solution of sodium tert-butoxide (5.29 g, 1.1 eq) in ethanol (51 mL) was added to a mixture of the material from Part A (1.0 eq) and diethyl oxalate (7.45 mL, 1.1 eq). The vessel containing the material from part A and diethyl oxalate was rinsed with additional ethanol (27 mL) and the rinse was added to the reaction mixture. The reaction mixture was stirred for 2 hours and then cooled to 0° C. Acetic acid (57 mL) was added and the reaction mixture was stirred for 5 minutes. Methylhydrazine (2.64 mL, 1.0 eq) was added dropwise. After 15 minutes the ice bath was removed and the reaction mixture was stirred overnight. The reaction mixture was concentrated under reduced pressure and the residue was partitioned between 50% aqueous sodium carbonate (450 mL) and dichloromethane (250 mL). The aqueous layer was back extracted with dichloromethane (100 mL). The combined organics were dried over magnesium sulfate and then concentrated under reduced pressure at ambient temperature to provide 11.76 g of a yellow oil. This material was purified by automated flash chromatography (eluting with 30% ethyl acetate in hexanes for 1 column volume, with a gradient of 30-70% ethyl acetate in hexanes over 6 column volumes, and with 70% ethyl acetate in hexanes for 1 column volume) to provide 4.99 g of ethyl 1-methyl-5-(tetrahydro-4H-pyran-4-ylidenemethyl)-1H-pyrazole-3-carboxylate as a yellow oil. Analysis by HPLC, LCMS, TLC, and $^1$H NMR indicated clean product with residual ethyl acetate (14%).

Part C

A solution of sodium hydroxide (1.99 g, 2.5 eq) in water (5 mL) was added to a stirred solution of the material from Part B (1.0 eq) in ethanol (50 mL). The reaction mixture was stirred for 30 minutes and then the bulk of the ethanol was removed under reduced pressure. The residue was diluted with dichloromethane (250 mL) and water (50 mL). The aqueous layer was acidified (pH about 1-2) with hydrochloric acid (50 mL of 1 M). The layers were separated and the aqueous layer was back extracted with dichloromethane (4×125 mL). The combined organics were dried over magnesium sulfate and then concentrated under reduced pressure to provide 4.82 g of 1-methyl-5-(tetrahydro-4H-pyran-4-ylidenemethyl)-1H-pyrazole-3-carboxylic acid.

Part D

1-Hydroxybenzotriazole hydrate (3.23 g, 1.2 eq) and 1-(3-dimethylaminopropyl)-3-ethylcarbodiimide hydrochloride (EDC, 4.58 g, 1.2 eq) were added sequentially to a solution of the material from Part C (1.0 eq) in DMF (25 mL). After 25 minutes the EDC was dissolved. After 1 hour the reaction mixture was cooled to 0° C. and concentrated ammonium hydroxide (5.3 mL, 4.0 eq) was added. Solids formed several minutes later. The reaction mixture was stirred for 30 minutes, diluted with water (100 mL), and then stirred for 20 minutes. The solids were isolated by filtration, rinsed with water (2×25 mL), and then dried to provide 3.69 g of 1-methyl-5-(tetrahydro-4H-pyran-4-ylidenemethyl)-1H-pyrazole-3-carboxamide as a white powder.

Part E

3-Chloroperoxybenzoic acid (4.51 g, 1.1 eq based on 70% titer) was added to a stirred suspension of the material from Part D (1.0 eq) in chloroform (83 ml). After several minutes a solution was obtained. The solution was stirred overnight, diluted with additional chloroform (275 mL), and then washed with a solution of saturated sodium bicarbonate:5% sodium hydroxide (20:1, 1×150 mL, then 1×100 mL). The organic layer was dried over magnesium sulfate and then concentrated under reduced pressure to provide a voluminous white foam. This material was concentrated from ethanol to provide 3.94 g of 5-(1,6-dioxaspiro[2.5]oct-2-yl)-1-methyl-1H-pyrazole-3-carboxamide as a white solid.

Part F

A suspension of the material from Part E (1.0 eq) in ethanol (170 mL) was warmed until most of the solid was dissolved and then cooled to 35° C. 10% Palladium on carbon (400 mg) and ammonium formate (5.24 g, 5.0 eq) were added sequentially. The reaction mixture was allowed to cool to ambient temperature and stirred for 4 hours. The reaction mixture was filtered through a layer of CELITE filter agent. The filter cake was rinsed sequentially with ethanol (3×25 mL), methanol (4×25 mL), and 1:1 methanol:chloroform (total of about 500 mL). The filtrate was concentrated under reduced pressure to provide 5.74 g of a white solid. This material was triturated with ethanol (45 mL), isolated by filtration, rinsed with ethanol (3×8 mL), and then dried to provide 3.13 g of 5-[(4-hydroxytetrahydro-2H-pyran-4-yl)methyl]-1-methyl-1H-pyrazole-3-carboxamide as a white crystalline solid.

Part G

Triethylamine (5.13 mL, 3.0 eq) was added to a stirred suspension of a portion of the material from Part F (2.91 g, 1.0 eq). The mixture was cooled to 0° C. and trifluoroacetic anhydride (5.14 mL, 3.0 eq) was added dropwise over a period of 5 minutes. The reaction mixture was stirred for 2 hours, quenched with saturated sodium carbonate (50 mL), and then allowed to warm to ambient temperature. Water (50 mL) and dichloromethane (200 mL) were added sequentially. The organic layer was separated, dried over magnesium sulfate, and then concentrated under reduced pressure to provide a yellow oil. The oil was dissolved in methanol (80 mL). Solid potassium carbonate (420 mg, 0.25 eq) was added and the mixture was stirred for 30 minutes. Aqueous hydrochloric acid (1.7 mL of 7 M, 1.0 eq) was added, the solution was stirred for 10 minutes, and then the bulk of the methanol was removed under reduced pressure. The residue was partitioned between dichloromethane (200 mL) and water (50 mL). The pH of the aqueous layer was adjusted to 7-8 with saturated sodium bicarbonate. The layers were separated and the aqueous layer was back extracted with dichloromethane (2×75 mL). The combined organics were dried over magnesium sulfate and then concentrated under reduced pressure to provide 2.37 g of a light yellow semisolid. This material was triturated with 5:95 methanol:chloroform (10 mL). A solid was isolated by filtration and rinsed with 5:95 methanol:chloroform (1×6 mL, then 1×2 mL) to provide 536 mg of 5-[(4-hydroxytetrahydro-2H-pyran-4-yl)methyl]-1-methyl-1H-pyrazole-3-carbonitrile as a white solid (lot 1). The filtrate was concentrated to provide a viscous yellow oil which was crystallized from warm ethanol (about 15 mL). A solid was isolated by filtration, rinsed with ethanol (2×5 mL), and then dried to provide 380 mg of 5-[(4-hydroxytetrahydro-2H-pyran-4-yl)methyl]-1-methyl-1H-pyrazole-3-carbonitrile as prisms (lot 2). The filtrate was concentrated to a semisolid. This material was purified by automated flash chromatography (eluting with 5:95 methanol:chloroform for 8 column volumes) to provide 0.47 g of 5-[(4-hydroxytetrahydro-2H-pyran-4-yl)methyl]-1-methyl-1H-pyrazole-3-carbonitrile (lot 3) as a white solid.

Part H

A solution of material from Part G (lots 1 and 2, 1.0 eq) in dichloromethane (41 mL) was cooled to 0° C. [Bis(2-methoxyethyl)amino]sulfur trifluoride (1.14 mL, 1.5 eq) was added dropwise. The reaction mixture was stirred for 45 minutes, quenched with saturated sodium bicarbonate (20 mL), and allowed to warm to ambient temperature. Saturated sodium bicarbonate (50 mL) and dichloromethane (50 mL) were added sequentially. The layers were separated and the aqueous layer was back extracted with dichloromethane (30 mL). The combined organics were dried over magnesium sulfate and then concentrated under reduced pressure at ambient temperature to provide 1.19 g of a light orange oil. This material was purified by automated flash chromatography (eluting with 10% ethyl acetate in 2:1 hexanes:dichloromethane for 2 column volumes, a gradient of 10-30% ethyl acetate in 2:1 hexanes:dichloromethane over 8 column volumes, and 30% ethyl acetate in 2:1 hexanes:dichloromethane for 4 column volumes) to provide 401 mg of 5-[(4-fluorotetrahydro-2H-pyran-4-yl)methyl]-1-methyl-1H-pyrazole-3-carbonitrile as a clear colorless oil which crystallized on standing.

Part I

Potassium acetate (437 mg, 2.5 eq) was added to a stirred solution of the material from Part H (1.0 eq) in acetic acid (4 mL). After the potassium acetate had dissolved, bromine (0.13 mL, 1.4 eq) was added dropwise. The resulting red solution was stirred for 18 hours. Additional potassium acetate (2 eq), acetic acid (0.5 mL), and bromine (1.4 eq) were added sequentially. The reaction mixture was stirred for 2.5 hours and then quenched with saturated sodium thiosulfate until colorless (about 4 mL). The reaction mixture was concentrated under reduced pressure and then diluted with water (10 mL) and saturated sodium carbonate (10 mL added dropwise). The resulting foamy suspension was combined with dichloromethane (50 mL). The aqueous layer was adjusted to about pH 8 with 5% sodium hydroxide. The layers were separated and the aqueous layer was back extracted with dichloromethane (50 mL). The combined organics were dried over magnesium sulfate and then concentrated under reduced pressure to provide 0.59 g of a light yellow solid. The bulk of the material was dissolved in 10:90 methanol:dichloromethane (40 mL), loaded onto silica gel, and then purified by automated flash chromatography (eluting with dichloromethane for 3 column volumes, a gradient of 0-10% ethyl acetate in dichloromethane over 5 column volumes, and then 10% ethyl acetate in dichloromethane for 10 column volumes) to provide 474 mg of 4-bromo-5-[(4-fluorotetrahydro-2H-pyran-4-yl)methyl]-1-methyl-1H-pyrazole-3-carbonitrile as a white solid.

Part J

Water (2.5 mL) was added dropwise to a stirred solution of the material from Part I (1.0 eq) in 1,2-dimethoxyethane (7.5 mL). 2-Aminophenylboronic acid hydrochloride (460 mg, 1.7 eq) and potassium carbonate (712 mg, 3.3 eq) were added sequentially. The reaction mixture was purged with nitrogen and then dichlorobis(triphenylphosphine)palladium(II) (22 mg, 0.02 eq) was added. The reaction mixture was heated at 75° C. for 9 hours and then allowed to cool to ambient temperature over the weekend. The reaction mixture was concentrated under reduced pressure and the residue was partitioned between dichloromethane (50 mL) and water (30 mL). The organic layer was separated, dried over magnesium sulfate, and then concentrated under reduced pressure to provide 2 g of a brown oil. This material was dissolved in ethanol (10 mL) and a precipitate formed immediately. Hydrochloric acid (0.90 mL of 7 M, 4.0 eq) was added and the resulting solution was heated at 75° C. for 4 hours. The reaction mixture was cooled to ambient temperature and then concentrated under reduced pressure. The residue was partitioned between dichloromethane (75 mL) and an aqueous mixture of saturated sodium bicarbonate (25 mL) and water (25 mL). The aqueous layer was separated and then extracted with dichloromethane (2×40 mL). The combined organics were dried over magnesium sulfate and then concentrated under reduced pressure to provide 0.66 g of a brown foam. This material was purified by automated flash chromatography (eluting with a gradient of 0-20% CMA in chloroform over 10 column volumes and 20% CMA in chloroform for 3 column volumes) to provide 200 mg of a tan solid. This material was triturated with hot ethanol (about 8 mL), isolated by filtration, rinsed with ethanol (3×5 mL), and then dried (0.15 torr (20 Pa), 130° C., 2 hours) to provide 143 mg of 1-[(4-fluorotetrahydro-2H-pyran-4-yl)methyl]-2-methyl-2H-pyrazolo[3,4-c]quinolin-4-amine as a tan powder, mp 252-254° C. $^1$H NMR (500 MHz, DMSO-$d_6$): δ 8.16 (d, J=7.8 Hz, 1H), 7.47 (dd, J=1.2, 8.1 Hz, 1H), 7.32 (m, 1H), 7.17 (m, 1H), 6.65 (br s, 2H), 4.12 (s, 3H), 3.73 (m, 4H), 3.45 (m, 2H), 2.08 (m, 1H), 2.00 (m, 1H), 1.65 (m, 2H); MS (ESI) 315 m/z (M+H)$^+$; Anal. calcd for $C_{17}H_{19}FN_4O$·0.04 EtOH·0.25$H_2O$: C, 63.97; H, 6.20; N, 17.47. Found: C, 63.97; H, 6.10; N, 17.49.

Example 8

4-[(4-Amino-2-methyl-2H-pyrazolo[3,4-c]quinolin-1-yl)methyl]tetrahydro-2H-pyran-4-ol

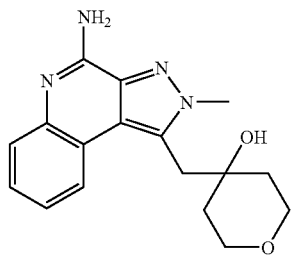

Part A

Potassium acetate (0.52 g, 2.5 eq) was added to a stirred solution of 5-[(4-hydroxytetrahydro-2H-pyran-4-yl)methyl]-1-methyl-1H-pyrazole-3-carbonitrile (Example 7, Part G, lot 3, 0.47 g, 1.0 eq) in acetic acid (7 mL). The reaction mixture was stirred until all of the potassium acetate was dissolved. Bromine (0.15 mL, 1.4 eq) was added dropwise and the reaction was stirred for 16 hours. The reaction mixture was quenched with saturated sodium thiosulfate (4 mL) and then the bulk of the acetic acid was removed under reduced pressure. The residue was diluted with water (15 mL) and saturated sodium carbonate (about 10-12 mL) and then extracted with dichloromethane (3×25 mL). The combined organics were dried over magnesium sulfate and then concentrated under reduced pressure to provide 0.72 g of a yellow solid. This material was purified by automated flash chromatography (eluting with 30% CMA in chloroform for 7 column volumes) to provide 528 mg of 4-bromo-5-[(4-hydroxytetrahydro-2H-pyran-4-yl)methyl]-1-methyl-1H-pyrazole-3-carbonitrile as a colorless sticky semisolid.

Part B

The material from Part A (1.0 eq) was coupled with 2-aminophenylboronic acid hydrochloride (1.8 eq) and then cyclized using the general method of Example 7 Part J. The crude product was purified by automated flash chromatography (eluting with 20% CMA in chloroform for 3 column volumes, a gradient of 20-40% CMA in chloroform over 10 column volumes, and 40% CMA in chloroform for 3 column volumes) to provide a tan solid. This material was triturated with hot ethyl acetate (about 8 mL), isolated by filtration, rinsed with ethyl acetate (3×5 mL), and dried under high vacuum to provide 106 mg of 4-[(4-amino-2-methyl-2H-pyrazolo[3,4-c]quinolin-1-yl)methyl]tetrahydro-2H-pyran-4-ol as a tan powder, mp 260-262 (dec)° C. $^1$H NMR (500 MHz, DMSO-$d_6$): δ8.19 (dd, J=1.0, 8.0 Hz, 1H), 7.46 (dd, J=1.2, 8.1 Hz, 1H), 7.30 (m, 1H), 7.17 (m, 1H), 6.61 (s, 2H), 4.77 (s, 1H), 4.16 (s, 3H), 3.55 (m, 4H), 3.41 (s, 2H), 1.84 (m, 2H), 1.44 (br s, 1H), 1.39 (br s, 1H); MS (APCI) 313 m/z (M+H)+; Anal. calcd for $C_{17}H_{20}N_4O_2 \cdot 0.25H_2O$: C, 64.44; H, 6.52; N, 17.68. Found: C, 64.11; H, 6.32; N, 17.60

Example 9

2-Ethyl-1-[(4-fluorotetrahydro-2H-pyran-4-yl)methyl]-2H-pyrazolo[3,4-c]quinolin-4-amine

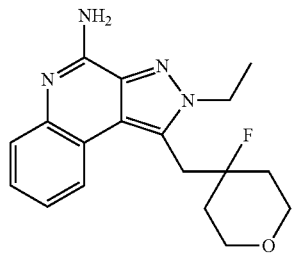

2-Ethyl-1-[(4-fluorotetrahydro-2H-pyran-4-yl)methyl]-2H-pyrazolo[3,4-c]quinolin-4-amine was prepared according to the general method of Example 7 Parts A through J using 1.3 eq of ethylhydrazine oxalate in lieu of methylhydrazine in part B. The crude product was purified by automated flash chromatography (eluting with a gradient of 0-20% CMA in chloroform over 5 column volumes and 20% CMA in chloroform for 5 column volumes) to provide 170 mg of a tan solid. This material was triturated with methanol (about 12 mL), isolated by filtration, rinsed with methanol (3×5 mL), and dried under high vacuum to provide 112 mg of 2-ethyl-1-[(4-fluorotetrahydro-2H-pyran-4-yl)methyl]-2H-pyrazolo[3,4-c]quinolin-4-amine as a tan powder, mp 275-277° C. $^1$H NMR (500 MHz, DMSO-$d_6$): δ 8.15 (d, J=7.6 Hz, 1H), 7.48 (dd, J=1.2, 8.1 Hz, 1H), 7.20 (m, 1H), 7.17 (m, 1H), 6.64 (br s, 2H), 4.44 (q, J=7.2 Hz, 2H), 3.73 (m, 4H), 3.44 (t, J=11.3 Hz, 2H), 2.10 (ddd, J=5.4, 13.5, 13.5 Hz, 1H), 1.97 (ddd, J=5.6, 13.6, 13.6 Hz, 1H), 1.64 (m, 2H), 1.48 (t, J=7.1 Hz, 3H); MS (ESI) 329 m/z (M+H)+; Anal. calcd for $C_{18}H_{21}FN_4O$: C, 65.84; H, 6.45; N, 17.06. Found: C, 65.56; H, 6.24; N, 16.93.

Example 10

4-[(4-Amino-2-ethyl-2H-pyrazolo[3,4-c]quinolin-1-yl)methyl]tetrahydro-2H-pyran-4-ol

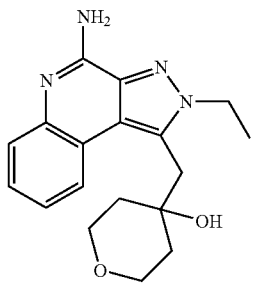

Part A

Di(tert-butyl)2-ethyl-1-methyl-2H-pyrazolo[3,4-c]quinolin-4-ylimidodicarbonate was prepared according to the method of Example 1 Part E using 2-ethyl-1-methyl-2H-pyrazolo[3,4-c]quinolin-4-amine (International Publication Number WO 2005/079195, Example 35) in lieu of 1-methyl-2-propyl-2H-pyrazolo[3,4-c]quinolin-4-amine. The crude product was triturated with hexanes to provide 13.34 g di(tert-butyl)2-ethyl-1-methyl-2H-pyrazolo[3,4-c]quinolin-4-ylimidodicarbonate as a white granular solid.

Part B

Di(tert-butyl)2-ethyl-1-methyl-2H-pyrazolo[3,4-c]quinolin-4-ylimidodicarbonate was reacted with tetrahydro-4H-pyran-4-one according to the method of Example 2 using di(tert-butyl)2-ethyl-1-methyl-2H-pyrazolo[3,4-c]quinolin-4-ylimidodicarbonate in lieu of di(tert-butyl)1-methyl-2-propyl-2H-pyrazolo[3,4-c]quinolin-4-ylimidodicarbonate. The crude product was recrystallized acetonitrile provide 0.349 g 4-[(4-amino-2-ethyl-2H-pyrazolo[3,4-c]quinolin-1-yl)methyl]tetrahydro-2H-pyran-4-ol as off-white crystals, mp 253-255° C.

MS (ESI) m/z 327.28 (M+H)+

Anal. Calcd for $C_{18}H_{22}N_4O_2$: C, 66.24; H, 6.79; N, 17.16. Found: C, 66.45; H, 7.05; N, 17.24.

Example 11

1-[(4-Amino-2-ethyl-2H-pyrazolo[3,4-c]quinolin-1-yl)methyl]cyclohexanol

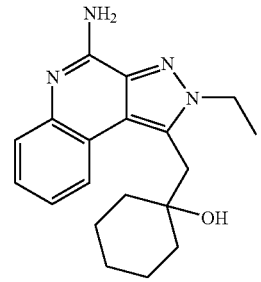

1-[(4-Amino-2-ethyl-2H-pyrazolo[3,4-c]quinolin-1-yl)methyl]cyclohexanol was prepared according to the method of Example 1 Part F using di(tert-butyl)2-ethyl-1-methyl-2H-pyrazolo[3,4-c]quinolin-4-ylimidodicarbonate in lieu of di(tert-butyl)1-methyl-2-propyl-2H-pyrazolo[3,4-c]quinolin-4-ylimidodicabonate and cyclohexanone in lieu of cyclobutanone. The crude product was recrystallized from acetonitrile to provide 0.560 g of 1-[(4-amino-2-ethyl-2H-pyrazolo[3,4-c]quinolin-1-yl)methyl]cyclohexanol as a white powder, mp 211.5-213° C.

MS (ESI) m/z 325.23 (M+H)+

Anal. Calcd for $C_{19}H_{24}N_4O$: C, 70.34; H, 7.46; N, 17.27. Found: C, 70.19; H, 7.57; N, 17.35.

Example 12

1-[(4-Amino-2-ethyl-2H-pyrazolo[3,4-c]quinolin-1-yl)methyl]cyclopentanol

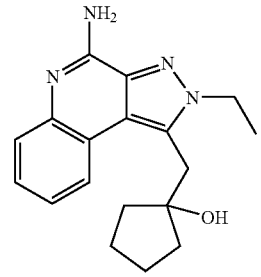

1-[(4-Amino-2-ethyl-2H-pyrazolo[3,4-c]quinolin-1-yl)methyl]cyclopentanol was prepared according to the method of Example 1 Part F using di(tert-butyl)2-ethyl-1-methyl-2H-pyrazolo[3,4-c]quinolin-4-ylimidodicarbonate in lieu of di(tert-butyl)1-methyl-2-propyl-2H-pyrazolo[3,4-c]quinolin-4-ylimidodicarbonate and cycpentanone in lieu of cyclobutanone. The crude product was triturated with acetonitrile and isolated by filtration to provide 0.414 g of 1-[(4-amino-2-ethyl-2H-pyrazolo[3,4-c]quinolin-1-yl)methyl]cyclopentanol as a white powder, mp 256-259° C.

MS (ESI) m/z 311.32 (M+H)$^+$

Anal. Calcd for $C_{18}H_{22}N_4O \cdot 0.02CHCl_3$: C, 69.20; H, 7.10; N, 17.91. Found: C, 68.95; H, 6.79; N, 17.83.

Example 13

1-[(4-Amino-2-ethyl-2H-pyrazolo[3,4-c]quinolin-1-yl)methyl]cyclobutanol

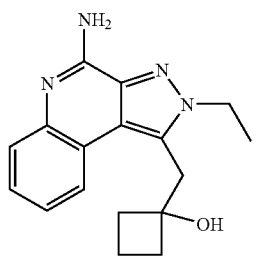

1-[(4-Amino-2-ethyl-2H-pyrazolo[3,4-c]quinolin-1-yl)methyl]cyclobutanol was prepared according to the method of Example 1 Part F using di(tert-butyl)2-ethyl-1-methyl-2H-pyrazolo[3,4-c]quinolin-4-ylimidodicarbonate in lieu of di(tert-butyl)1-methyl-2-propyl-2H-pyrazolo[3,4-c]quinolin-4-ylimidodicarbonate. The crude product was triturated with acetonitrile and isolated by filtration to provide 0.396 g of 1-[(4-amino-2-ethyl-2H-pyrazolo[3,4-c]quinolin-1-yl)methyl]cyclobutanol as a white solid, mp 245-247° C.

MS (ESI) m/z 297.26 (M+H)$^+$

Anal. Calcd for $C_{17}H_{20}N_4O$: C, 68.90; H, 6.80; N, 18.90. Found: C, 68.66; H, 6.72; N, 18.83.

Example 14

4-[(4-Amino-2-ethyl-2H-pyrazolo[3,4-c]quinolin-1-yl)methyl]tetrahydro-2H-thiopyran-4-ol

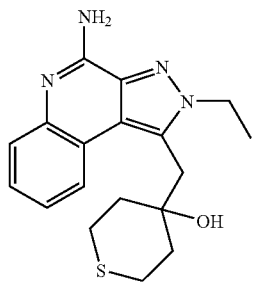

4-[(4-Amino-2-ethyl-2H-pyrazolo[3,4-c]quinolin-1-yl)methyl]tetrahydro-2H-thiopyran-4-ol was prepared according to the method of Example 1 Part F using di(tert-butyl)2-ethyl-1-methyl-2H-pyrazolo[3,4-c]quinolin-4-ylimidodicarbonate in lieu of di(tert-butyl)1-methyl-2-propyl-2H-pyrazolo[3,4-c]quinolin-4-ylimidodicarbonate and 4-oxothiane in lieu of cyclobutanone. The crude product was recrystallized from acetonitrile to provide 0.475 g of 4-[(4-amino-2-ethyl-2H-pyrazolo[3,4-c]quinolin-1-yl)methyl]tetrahydro-2H-thiopyran-4-ol as a white powder, mp 251.5-255° C.

MS (ESI) m/z 343.29 (M+H)$^+$

Anal. Calcd for $C_{18}H_{22}N_4OS$: C, 63.13; H, 6.48; N, 16.36; S, 9.36. Found: C, 63.02; H, 6.67; N, 16.37; S, 9.36.

Example 15

1-Acetyl-4-[(4-amino-2-ethyl-2H-pyrazolo[3,4-c]quinolin-1-yl)methyl]piperidin-4-ol

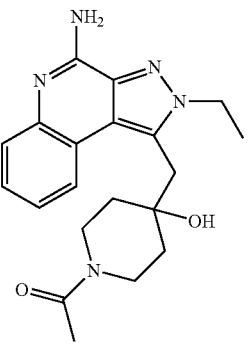

Part A

4-[(4-Amino-2-ethyl-2H-pyrazolo[3,4-c]quinolin-1-yl)methyl]piperidin-4-ol was prepared according to the method of Example 1 Part F using di(tert-butyl)2-ethyl-1-methyl-2H-pyrazolo[3,4-c]quinolin-4-ylimidodicarbonate in lieu of di(tert-butyl)1-methyl-2-propyl-2H-pyrazolo[3,4-c]quinolin-4-ylimidodicarbonate and tert-butyl 4-oxopiperidine-1-carboxylate in lieu of cyclobutanone. The crude product was recrystallized from acetonitrile to provide 1.09 g of 1-[(4-amino-2-ethyl-2H-pyrazolo[3,4-c]quinolin-1-yl)methyl]piperidin-4-ol as an off-white solid.

Part B

Acetic anhydride (88 µL, 0.922 mmol) was added to a slurry of 4-[(4-amino-2-ethyl-2H-pyrazolo[3,4-c]quinolin-1-yl)methyl]piperidin-4-ol (0.300 g, 0.922 mmol) in chloroform (10 mL). After 16 hours, the solution was purified via automated flash chromatography eluting with a linear gradient of 2-25% CMA in chloroform. The residue was triturated in acetonitrile and isolated by filtration to provide 0.209 g of 1-acetyl-4-[(4-amino-2-ethyl-2H-pyrazolo[3,4-c]quinolin-1-yl)methyl]piperidin-4-ol as a white solid, mp 231-232.5° C.

MS (ESI) m/z 368.20 (M+H)$^+$

Anal. Calcd for $C_{20}H_{25}N_5O_2$: C, 65.37; H, 6.86; N, 19.06. Found: C, 65.14; H, 7.03; N, 19.25.

Example 16

4-[(4-Amino-2-ethyl-2H-pyrazolo[3,4-c]quinolin-1-yl)methyl]-1-(methylsulfonyl)piperidin-4-ol

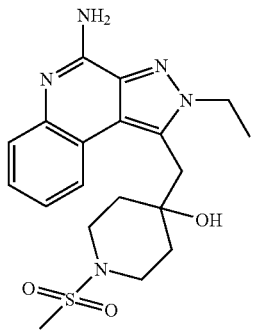

Methanesulfonic anhydride (0.160 g, 0.922 mmol) was added to a slurry of 4-[(4-amino-2-ethyl-2H-pyrazolo[3,4-c]quinolin-1-yl)methyl]piperidin-4-ol (0.300 g, 0.922 mmol) in chloroform (10 mL). After 16 hours, 2M aqueous sodium carbonate was added and the biphasic mixture was stirred for 30 minutes resulting in a white precipitate. The mixture was extracted with 10% methanol in dichloromethane. The solution was concentrated. The residue was purified via automated flash chromatography and recrystallized from acetonitrile to provide 0.165 g of 4-[(4-amino-2-ethyl-2H-pyrazolo[3,4-c]quinolin-1-yl)methyl]-1-(methylsulfonyl)piperidin-4-ol as a white solid, mp 268-270° C.

MS (ESI) m/z 404.30 (M+H)$^+$

Anal. Calcd for $C_{19}H_{25}N_5O_3S \cdot 0.3H_2O \cdot 0.15\ CH_3CN$: C, 55.97; H, 6.32; N, 17.43; S, 7.74. Found: C, 56.33; H, 6.23; N, 17.56; S, 7.73.

Example 17

4-[(4-Amino-2-ethyl-2H-pyrazolo[3,4-c]quinolin-1-yl)methyl]-4-hydroxy-N-propylpiperidine-1-carboxamide

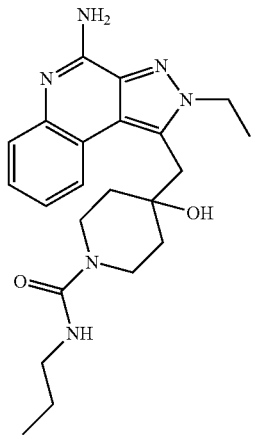

n-Propyl isocyanate (86 μL, 0.922 mmol) was added to a slurry of 4-[(4-amino-2-ethyl-2H-pyrazolo[3,4-c]quinolin-1-yl)methyl]piperidin-4-ol (0.300 g, 0.922 mmol) in chloroform (10 mL). After 16 hours, the solution was purified via automated flash chromatography eluting with a linear gradient of 2-25% CMA in chloroform. The residue was triturated in acetonitrile and isolated by filtration to provide 0.277 g of 4-[(4-amino-2-ethyl-2H-pyrazolo[3,4-c]quinolin-1-yl)methyl]-4-hydroxy-N-propylpiperidine-1-carboxamide as a flocculent white solid, mp 208.5-210° C.

MS (ESI) m/z 411.28 (M+H)$^+$

Anal. Calcd for $C_{22}H_{30}N_6O_2 \cdot 0.3H_2O$: C, 63.53; H, 7.42; N, 20.21. Found: C, 63.49; H, 7.16; N, 20.09.

Example 18

2-Ethyl-1-(tetrahydro-2H-pyran-4-ylmethyl)-2H-pyrazolo[3,4-c]quinolin-4-amine

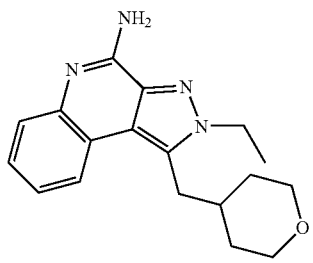

2-Ethyl-1-(tetrahydro-2H-pyran-4-ylmethyl)-2H-pyrazolo[3,4-c]quinolin-4-amine was prepared according to the methods of Example 3 parts A-I. Ethylhydrazine oxalate was used in lieu of propylhydrazine oxalate in part C. The crude product was recrystallized from acetonitrile to provide 0.371 g of 2-ethyl-1-(tetrahydro-2H-pyran-4-ylmethyl)-2H-pyrazolo[3,4-c]quinolin-4-amine as tan crystals, m.p. 226.0-228.0° C.

MS (ESI) m/z 311.29 (M+H)$^+$

Anal. Calcd for $C_{18}H_{22}N_4O$: C, 69.65; H, 7.14; N, 18.05. Found: C, 69.81; H, 7.26; N, 18.29.

Example 19

1-[(4-Amino-2-ethyl-6,7,8,9-tetrahydro-2H-pyrazolo[3,4-c]quinolin-1-yl)methyl]cyclohexanol

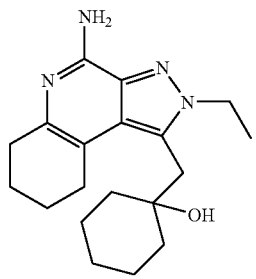

1-[(4-Amino-2-ethyl-2H-pyrazolo[3,4-c]quinolin-1-yl)methyl]cyclohexanol (0.226 g, 0.70 mmol) and platinum(IV) oxide (0.107 g, 0.47 mmol) were slurried in trifluoroacetic acid (10 mL). The flask was degassed three times and charged to 50 psi hydrogen (3.45×10$^5$ Pa). After 16 hours, the catalyst was removed via filtration through a bed of CELITE filter agent, rinsing with methanol. The filtrate was concentrated. The oily residue was dissolved in 6N hydrochloric acid (3 mL). The acidic mixture was brought to pH 14 using 50% aqueous sodium hydroxide. The mixture was extracted with 10% methanol in dichloromethane, dried over anhydrous sodium sulfate, and concentrated. The material was purified via automated flash chromatography eluting with a linear gradient of 2-20% CMA in chloroform. The resulting white solid was triturated in acetonitrile and then isolated by filtration to provide 0.085 g of 1-[(4-amino-2-ethyl-6,7,8,9-tetrahydro-2H-pyrazolo[3,4-c]quinolin-1-yl)methyl]cyclohexanol as a white solid, m.p. 232-234° C.

MS (ESI) m/z 329.44 (M+H)$^+$

Anal. Calcd for $C_{19}H_{28}N_4O$: C, 69.48; H, 8.59; N, 17.06. Found: C, 69.28; H, 8.51; N, 17.06.

Example 20

1-{[4-Fluoro-1-(methylsulfonyl)piperidin-4-yl]methyl}-2-methyl-2H-pyrazolo[3,4-c]quinolin-4-amine

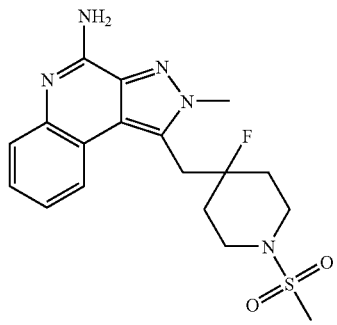

Part A

The method described in Part A of Example 3 was followed using 1-Boc-4-piperidinone (46.6 g, 0.234 mol) instead of tetrahydro-4H-pyran-4-one. The crude product was purified by column chromatography on silica gel (eluting with 5% ethyl acetate in hexanes) and then concentrated from ethyl acetate/hexanes to provide 23.7 g of tert-butyl 4-(2-oxopropylidene)piperidine-1-carboxylate as a white solid.

Part B

A solution of tert-butyl 4-(2-oxopropylidene)piperidine-1-carboxylate (20.0 g, 83.6 mmol) and diethyl oxalate (24.9 mL, 2.2 equivalents (eq.)) in ethanol (15 mL) was added to a solution of potassium ethoxide (15.47 g, 2.2 eq.) in ethanol (170 mL) at room temperature. The addition vessel was rinsed with ethanol (2×5 mL), and the rinses were added to the reaction. The reaction was stirred for 1 hour and then cooled in an ice bath to 4° C. Acetic acid (100 mL) was added, and the reaction was stirred for several minutes to allow internal temp to return to 4° C. Methyl hydrazine (19.4 mL, 4.4 eq) was added dropwise over a period of five minutes. After 15 minutes the ice bath was removed, and the reaction mixture was stirred for 1 hour. The reaction mixture was concentrated under reduced pressure and the residue was partitioned between water (300 mL) and dichloromethane (400 mL). Saturated aqueous sodium carbonate (100 mL) was added portionwise followed by 50% aqueous sodium hydroxide (40 mL) and 5% aqueous sodium hydroxide (100 mL) to adjust the mixture to pH 8. The aqueous layer was separated and extracted with dichloromethane (2×300 mL). The combined organics were dried over magnesium sulfate and then concentrated under reduced pressure to provide 38 g of brown oil. This material was purified by automated flash chromatography (eluting with tert-butyl methyl ether) to provide 6.2 g of tert-butyl 4-[(5-ethoxycarbonyl-2-methyl-2H-pyrazol-3-yl)methylene]piperidine-1-carboxylate as a yellow oil.

Part C

The material from Part B (6.03 g, 17.2 mmol) was treated according to the method of Part C of Example 7 with the modification that at the end of the reaction, the reaction mixture was cooled to 0° C., and hydrochloric acid (40 mL of 1 M) was added dropwise. Approximately half the solvent was removed under reduced pressure, and a precipitate formed and was collected by filtration, washed with cold water (2×25 mL), and dried under high vacuum to provide 3.71 g of tert-butyl 4-[(5-carboxy-2-methyl-2H-pyrazol-3-yl)methylene]piperidine-1-carboxylate as a white solid.

Part D

The material from Part C was treated according to the methods of Parts D, E, and F of Example 7. The crude solid obtained from Part F was partitioned between dichloromethane (200 mL) and water (100 mL). The aqueous solution was separated and extracted with chloroform (3×100 mL). The organic fractions were combined, dried over magnesium sulfate, and filtered. The filter cake was washed with chloroform (5×60 mL). The combined filtrates were concentrated under reduced pressure to provide 6.33 g of white foam, which was suspended in chloroform (125 mL), isolated by filtration, washed with chloroform (2×110 mL), and dried to provide 3.8 g of tert-butyl 4-[(5-carbamoyl-2-methyl-2H-pyrazol-3-yl)methyl]-4-hydroxypiperidine-1-carboxylate as a white solid. The filtrate was concentrated and dried to give an additional 3.0 g of product. Both solids contained chloroform and a trace impurity.

Part E

The material from Part D was treated with triethylamine and trifluoroacetic anhydride according to the method of Part G of Example 7. The crude yellow oil that was obtained was purified by automated flash chromatography (eluting with a gradient of 30% hexanes in tert-butyl methyl ether to 100% tert-butyl methyl ether over 4 column volumes and then 100% tert-butyl methyl ether for 3 column volumes) and dried under high vacuum to provide 3.62 of the trifluoroacetate ester of tert-butyl 4-[(5-cyano-2-methyl-2H-pyrazol-3-yl)methyl]-4-hydroxypiperidine-1-carboxylate as a colorless oil. A portion of the oil (3.43 g) was dissolved in methanol (80 mL), and concentrated ammonium hydroxide (1.6 mL) was added. The reaction was stirred for 1 hour and concentrated under reduced pressure. The residue was concentrated from chloroform (2×100 mL) and purified by automated flash chromatography (eluting with 20% CMA in chloroform) to provide 2.50 g of tert-butyl 4-[(5-cyano-2-methyl-2H-pyrazol-3-yl)methyl]-4 hydroxypiperidine-1-carboxylate as a sticky white solid, which was converted to tert-butyl 4-[(4-bromo-5-cyano-2-methyl-2H-pyrazol-3-yl)methyl]-4-fluoropiperidine-1-carboxylate according to the methods of Parts H and I of Example 7.

Part F

Hydrochloric acid (0.55 mL of 6 M) was added to a suspension of tert-butyl 4-[(4-bromo-5-cyano-2-methyl-2H-pyrazol-3-yl)methyl]-4-fluoropiperidine-1-carboxylate (446 mg, 1.11 mmol) in ethanol (10 mL), and the reaction was heated at 70° C. for 1.5 hours, allowed to cool to room temperature, and concentrated under reduced pressure to provide 4-bromo-5-[(4-fluoropiperidin-4-yl)methyl]-1-methyl-1H-pyrazole-3-carbonitrile hydrochloride as a white solid.

Part G

Triethylamine (0.62 mL, 4.0 eq.) was added to a stirred suspension of the material from Part F in dichloromethane (11 mL), and the mixture was cooled to 0° C. Methanesulfonyl chloride (0.095 mL, 1.1 eq.) was added, and the resulting solution was stirred for 1.5 hours. Saturated aqueous sodium bicarbonate (20 mL) was added, and the mixture was allowed to warm to room temperature and diluted with dichloromethane (75 mL). The organic layer was separated, dried over magnesium sulfate, filtered, and concentrated under reduced pressure to provide 0.43 g of a white solid. The solid was triturated with hot ethanol (15 mL), allowed to cool to room temperature, isolated by filtration, washed with ethanol (2×5 mL), and dried under high vacuum to provide 351 mg of 4-bromo-5-{[4-fluoro-1-(methylsulfonyl)piperidin-4-yl]methyl}-1-methyl-1H-pyrazole-3-carbonitrile as a white solid.

Part H

The reaction conditions and purification methods described in Part J of Example 7 were used to treat the material from Part G. 1-{[4-Fluoro-1-(methylsulfonyl)piperidin-4-yl]methyl}-2-methyl-2H-pyrazolo[3,4-c]quinolin-4-amine (71 mg) was obtained as a tan powder, mp 283-285° C. $^1$H NMR (300 MHz, DMSO-d$_6$): δ 8.17 (d, J=7.8 Hz, 1H), 7.47 (dd, J=1.2, 8.1 Hz, 1H), 7.32 (m, 1H), 7.17 (m, 1H), 6.67 (br s, 2H), 4.11 (s, 3H), 3.76 (dd, J=22.8 Hz, 2H), 3.46 (m, 2H), 2.86 (s, 3H), 2.80 (m, 2H), 1.98-2.28 (m, 2H), 1.86 (m, 2H); MS (APCI) 392 m/z (M+H)$^+$; Anal. calcd for $C_{18}H_{22}FN_5O_2S$: C, 55.23; H, 5.66; N, 17.89. Found: C, 54.99; H, 5.55; N, 17.70.

Example 21

1-[(1-Acetyl-4-fluoropiperidin-4-yl)methyl]-2-methyl-2H-pyrazolo[3,4-c]quinolin-4-amine

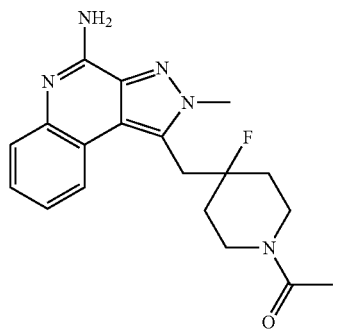

Part A

Triethylamine (3.4 mL, 3.0 eq.) was added to a stirred suspension of 4-bromo-5-[(4-fluoropiperidin-4-yl)methyl]-1-methyl-1H-pyrazole-3-carbonitrile hydrochloride (2.7 g, 8.0 mmol) in dichloromethane (80 mL), and the mixture was cooled to 0° C. Acetyl chloride (0.74 mL, 1.3 eq.) was added, and the resulting solution was stirred for 1.5 hours and concentrated under reduced pressure. The residue was dissolved in dichloromethane (300 mL), and the resulting solution was washed with water (100 mL), dried over magnesium sulfate, filtered, and concentrated under reduced pressure to provide 2.58 g of a white foam. The foam was purified by automated flash chromatography (eluting with a gradient of 0-20% CMA in chloroform over 8 column volumes) to provide 0.94 g of 5-[(1-acetyl-4-fluoropiperidin-4-yl)methyl]-4-bromo-1-methyl-1H-pyrazole-3-carbonitrile, which was concentrated from 1,2-dimethoxyethane (75 mL) prior to the next step.

Part B

The reaction conditions and purification methods described in Part J of Example 7 were used to treat the material from Part A. 1-[(1-Acetyl-4-fluoropiperidin-4-yl)methyl]-2-methyl-2H-pyrazolo[3,4-c]quinolin-4-amine (176 mg) was obtained as a white powder, mp 241-243° C. $^1$H NMR (300 MHz, DMSO-d$_6$): δ 8.14 (d, J=7.9 Hz, 1H), 7.47 (dd, J=1.1, 8.1 Hz, 1H), 7.32 (m, 1H), 7.16 (m, 1H), 6.66 (br s, 2H), 4.30 (br d, J=12.7 Hz, 1H), 4.11 (s, 3H), 3.71 (d, J=22.4 Hz, 2H), 3.70 (m, 1H), 3.12 (m, 1H), 2.61 (m, 1H), 2.00 (s, 3H), 1.74-2.14 (m, 4H); MS (ESI) 356 m/z (M+H)$^+$; Anal. calcd for $C_{19}H_{22}FN_5O$: C, 64.21; H, 6.24; N, 19.70. Found: C, 64.21; H, 6.04; N, 19.73.

Example 22

4-[(4-Amino-2-methyl-2H-pyrazolo[3,4-c]quinolin-1-yl)methyl]-4-fluoro-N-isopropylpiperidine-1-carboxamide

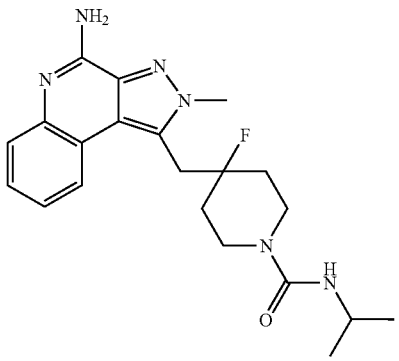

Part A

Triethylamine (1.5 mL, 1.5 eq.) was added to a stirred suspension of 4-bromo-5-[(4-fluoropiperidin-4-yl)methyl]-1-methyl-1H-pyrazole-3-carbonitrile hydrochloride (2.28 g, 6.75 mmol) in dichloromethane (67 mL), and isopropyl isocyanate (1.34 mL, 2.0 eq.) was added to the resulting solution. The reaction was stirred for 1.5 hours and concentrated under reduced pressure. The residue was dissolved in dichloromethane (300 mL), and the resulting solution was washed with water (100 mL), dried over magnesium sulfate, filtered, and concentrated under reduced pressure to provide 2.45 g of a white foam. The foam was purified by automated flash chromatography (eluting with a gradient of 0-10% CMA in chloroform over 8 column volumes) to provide 1.39 g of 4-[(4-bromo-5-cyano-2-methyl-2H-pyrazol-3-yl)methyl]-4-fluoro-N-isopropylpiperidine-1-carboxamide.

Part B

The reaction conditions and purification methods described in Part J of Example 7 were used to treat the material from Part A. 4-[(4-Amino-2-methyl-2H-pyrazolo[3,4-c]quinolin-1-yl)methyl]-4-fluoro-N-isopropylpiperidine-1-carboxamide (0.14 g) was obtained as a white powder, mp 241-244° C. $^1$H NMR (300 MHz, DMSO-d$_6$): δ 8.14 (d, J=7.4 Hz, 1H), 7.47 (dd, J=1.2, 8.1 Hz, 1H), 7.32 (m, 1H), 7.16 (m, 1H), 6.65 (br s, 2H), 6.17 (d, J=7.6 Hz, 1H), 4.11 (s, 3H), 3.67-3.89 (m, 5H), 2.73 (m, 2H), 1.64-2.00 (m, 4H), 1.03 (d, J=6.6 Hz, 6H); MS (ESI) m/z 399 (M+H)$^+$; Anal. calcd for $C_{21}H_{27}FN_6O\cdot0.02CHCl_3$: C, 62.98; H, 6.79; N, 20.96. Found: C, 62.59; H, 6.60; N, 20.69.

Example 23

2-Ethyl-1-{[4-fluoro-1-(methylsulfonyl)piperidin-4-yl]methyl}-2H-pyrazolo[3,4-c]quinolin-4-amine

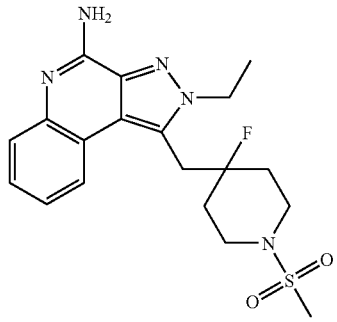

Part A

Starting with tert-butyl 4-(2-oxopropylidene)piperidine-1-carboxylate (25.0 g, 105 mmol) in lieu of 1-tetrahydro-4H-pyran-4-ylideneacetone and ethyl hydrazine oxalate (69.0 g, 460 mmol) in lieu of methyl hydrazine, the general methods of Parts B through F of Example 7 were followed to provide tert-butyl 4-[(5-carbamoyl-2-ethyl-2H-pyrazol-3-yl)methyl]-4-hydroxypiperidine-1-carboxylate (3.25 g, 9.22 mmol), which was treated with triethylamine and trifluoroacetic anhydride according to the method of Part G of Example 7. The crude yellow oil that was obtained was dissolved in methanol (50 ml), and concentrated ammonium hydroxide (1.84 mL) was added. The reaction was stirred for 1 hour and concentrated under reduced pressure. The residue was partitioned between water (100 mL) and chloroform (100 mL). The aqueous layer was separated and extracted with chloroform (2×100 mL). The combined organic fractions were dried over magnesium sulfate, filtered, and concentrated under reduced pressure. The residue was purified by automated flash chromatography (eluting with chloroform for 4 column volumes and then a gradient of 0-20% CMA in chloroform over 6 column volumes) and dried under high vacuum to provide 2.56 g of tert-butyl 4-[(5-cyano-2-ethyl-2H-pyrazol-3-yl)methyl]-4-hydroxypiperidine-1-carboxylate as a yellow oil, which was converted to tert-butyl 4-[(4-bromo-5-cyano-2-ethyl-2H-pyrazol-3-yl)methyl]-4-fluoropiperidine-1-carboxylate according to the methods of Parts H and I of Example 7.

Part B

Hydrochloric acid (2.64 mL of 6 M) was added to a suspension of tert-butyl 4-[(4-bromo-5-cyano-2-ethyl-2H-pyrazol-3-yl)methyl]-4-fluoropiperidine-1-carboxylate (3.3 g, 7.95 mmol) in ethanol (80 mL), and the reaction was heated at 80° C. for 2 hours, allowed to cool to room temperature, and concentrated under reduced pressure to provide 4-bromo-1-ethyl-5-[(4-fluoropiperidin-4-yl)methyl-1H-pyrazole-3-carbonitrile hydrochloride as a white solid.

Part C

Triethylamine (11.1 mL, 79.5 mmol) and methanesulfonyl chloride (1.24 mL, 15.9 mmol) were sequentially added to a mixture of the material from Part B in dichloromethane (80 mL), and the reaction was stirred for 5 minutes. Brine (40 mL) was added, and the aqueous layer was separated and extracted with dichloromethane (2×100 mL). The combined organic fractions were dried over magnesium sulfate, filtered, and concentrated under reduced pressure to provide a brown foam. The foam was purified by automated flash chromatography (eluting with a gradient of 0-10% CMA in chloroform over 8 column volumes) to provide 1.9 g of 4-bromo-1-ethyl-5-{[4-fluoro-1-(methylsulfonyl)piperidin-4-yl]methyl}-1H-pyrazole-3-carbonitrile as a tan foam.

Part D

The general reaction conditions and purification methods described in Part J of Example 7 were used to treat the material from Part C (1.0 g). 2-Ethyl-1-{[4-fluoro-1-(methylsulfonyl)piperidin-4-yl]methyl}-2H-pyrazolo[3,4-c]quinolin-4-amine (150 mg) was obtained as a light tan solid, mp 269-271° C. $^1$H NMR (300 MHz, DMSO-$d_6$): 8.16 (d, J=7.7 Hz, 1H), 7.48 (dd, J=8.0, 1.1 Hz, 1H), 7.32 (td, J=7.5, 1.0 Hz, 1H), 7.18 (td, J=7.5, 1.2 Hz, 1H), 6.64 (s, 2H), 4.44 (q, J=7.2 Hz, 2H), 3.76 (d, J=22.9 Hz, 2H), 3.46 (d, J=11.2 Hz, 2H), 2.86 (s, 3H), 2.80 (t, J=12.3 Hz, 2H), 2.03 (m, 4H), 1.49 (t, J=7.1 Hz, 3H), 1.03 (d, J=6.6 Hz, 6H); MS (EI) m/z 406 (M+H)$^+$; Anal. calcd for $C_{19}H_{24}FN_5O_2S$: C, 56.28; H, 5.97; N, 17.27. Found: C, 55.99; H, 5.71; N, 17.05.

Example 24

1-[(1-Acetyl-4-fluoropiperidin-4-yl)methyl]-2-ethyl-2H-pyrazolo[3,4-c]quinolin-4-amine

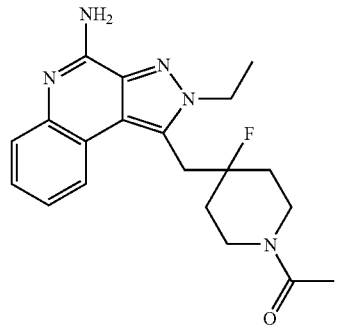

Part A

Triethylamine (3.35 mL, 24.0 mmol) was added to a stirred suspension of 4-bromo-1-ethyl-5-[(4-fluoropiperidin-4-yl)methyl-1H-pyrazole-3-carbonitrile hydrochloride (2.52 g, 8.0 mmol) in dichloromethane (80 mL), and the resulting solution was cooled to 0° C. Acetyl chloride (0.74 mL, 10.4 mmol) was added dropwise, and the resulting solution was stirred for 1 hour. Water (50 mL) was added, and then the aqueous layer was separated and extracted with dichloromethane (2×100 mL). The combined organic fractions were dried over magnesium sulfate, filtered, and concentrated under reduced pressure to provide a brown foam. The foam was purified by automated flash chromatography (eluting with a gradient of 0-10% CMA in chloroform over 8 column volumes) and dried under high vacuum to provide 1.6 g of 5-[(1-acetyl-4-fluoropiperidin-4-yl)methyl]-4-bromo-1-ethyl-1H-pyrazole-3-carbonitrile.

Part B

The reaction conditions described in Part J of Example 7 were used to treat the material from Part A. Following chromatographic purification (eluting with chloroform for 4 column volumes, followed by a gradient of 0-40% CMA in chloroform over 6 column volumes, followed by 40% CMA in chloroform) the resulting oil was recrystallized from acetonitrile. The solid was isolated by filtration, washed with acetonitrile, and dried under high vacuum to provide 121 mg of 1-[(1-acetyl-4-fluoropiperidin-4-yl)methyl]-2-ethyl-2H-pyrazolo[3,4-c]quinolin-4-amine as a light tan solid, mp 228-230° C. $^1$H NMR (300 MHz, DMSO-$d_6$): 8.14 (d, J=7.8 Hz, 1H), 7.48 (dd, J=8.1, 1.2 Hz, 1H), 7.31 (td, J=7.5, 1.1 Hz, 1H), 7.16 (td, J=7.4, 1.2 Hz, 1H), 6.64 (s, 2H), 4.44 (q, J=7.2 Hz, 2H), 4.30 (d, J=12.2 Hz, 1H), 3.71 (m, 3H), 3.12 (t, J=12.4 Hz, 1H), 2.60 (t, J=12.8 Hz, 1H), 2.00 (s, 3H), 1.93 (m, 4H), 1.48 (t, J=7.1 Hz, 3H); MS (EI) m/z 370 (M+H)+; Anal. calcd for $C_{20}H_{24}FN_5O$: C, 65.02; H, 6.55; N, 18.96. Found: C, 65.07; H, 6.32; N, 19.12.

Example 25

4-[(4-Amino-2-ethyl-2H-pyrazolo[3,4-c]quinolin-1-yl)methyl]-4-fluoro-N-isopropylpiperidine-1-carboxamide

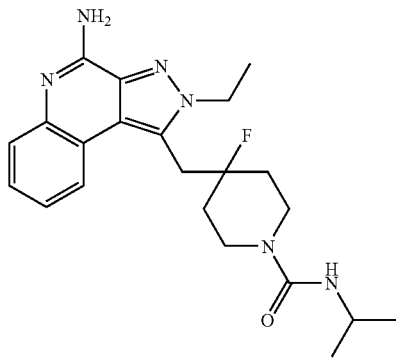

Part A

Triethylamine (2.23 mL, 16.0 mmol) and isopropyl isocyanate (1.01 mL, 10.4 mmol) were sequentially added to a mixture of 4-bromo-1-ethyl-5-[(4-fluoropiperidin-4-yl)methyl-1H-pyrazole-3-carbonitrile hydrochloride (2.52 g, 8.0 mmol) and dichloromethane (40 mL). The reaction was stirred for 1.5 hours and diluted with dichloromethane (250 mL), washed with water (100 mL), dried over magnesium sulfate, filtered, and concentrated under reduced pressure to provide a brown foam. The foam was purified by automated flash chromatography (eluting with a gradient of 0-10% CMA in chloroform over 8 column volumes). The resulting off-white foam was concentrated from 1,2-dimethoxyethane (50 mL), and dried under high vacuum to provide 1.6 g of 4-[(4-bromo-5-cyano-2-ethyl-2H-pyrazol-3-yl)methyl]-4-fluoro-N-isopropylpiperidine-1-carboxamide.

Part B

The reaction conditions described in Part J of Example 7 were used to treat the material from Part A. Following chromatographic purification using the conditions described in Part B of Example 24, the resulting brown solid was recrystallized from ethanol and dried to provide 93 mg of 4-[(4-amino-2-ethyl-2H-pyrazolo[3,4-c]quinolin-1-yl)methyl]-4-fluoro-N-isopropylpiperidine-1-carboxamide as a white solid, mp 205-207° C. $^1$H NMR (300 MHz, DMSO-$d_6$): 8.14 (d, J=7.8 Hz, 1H), 7.48 (dd, J=8.1, 1.1 Hz, 1H), 7.31 (td, J=7.5, 1.1 Hz, 1H), 7.16 (td, J=7.4, 1.2 Hz, 1H), 6.63 (s, 2H), 6.17 (d, J=7.6 Hz, 1H), 4.44 (q, J=7.2 Hz, 2H), 3.78 (m, 5H), 2.73 (t, J=12.1 Hz, 2H), 1.81 (m, 4H), 1.47 (t, J=7.1 Hz, 3H), 1.03 (6, J=6.6 Hz, 6H); MS (EI) m/z 413 (M+H)+; Anal. calcd for $C_{22}H_{29}FN_6O$: C, 64.06; H, 7.09; N, 20.37. Found: C, 63.93; H, 7.17; N, 20.30.

Example 26

1-{[4-Fluoro-1-(methylsulfonyl)piperidin-4-yl]methyl}-2-propyl-2H-pyrazolo[3,4-c]quinolin-4-amine

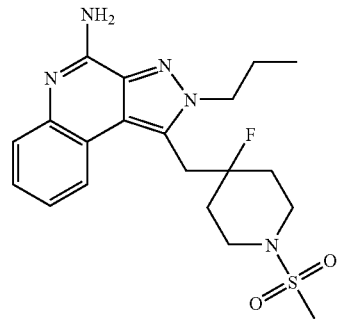

Part A

Starting with tert-butyl 4-(2-oxopropylidene)piperidine-1-carboxylate (20.0 g, 83.6 mmol) in lieu of 1-tetrahydro-4H-pyran-4-ylideneacetone and propyl hydrazine oxalate (34.3 g, 2.5 eq.) in lieu of methyl hydrazine, the general methods of Parts B through F of Example 7 were followed to provide tert-butyl 4-[(5-carbamoyl-2-propyl-2H-pyrazol-3-yl)methyl]-4-hydroxypiperidine-1-carboxylate (6.20 g, 16.9 mmol), which was treated with triethylamine and trifluoroacetic anhydride according to the method of Part G of Example 7. The crude yellow oil that was obtained was dissolved in methanol (45 mL), and concentrated ammonium hydroxide (3.4 mL) was added. The reaction was stirred for 1 hour and concentrated under reduced pressure. The residue was partitioned between water (150 mL) and chloroform (200 mL). The organic layer was separated and dried over magnesium sulfate, filtered, and concentrated under reduced pressure. The residue was purified twice by automated flash chromatography (eluting first with a gradient of 0-40% CMA in chloroform over 5 column volumes and second with a gradient of 0-50% ethyl acetate in chloroform over 5 column volumes) to provide 4.52 g of tert-butyl 4-[(5-cyano-2-propyl-2H-pyrazoly-3-yl)methyl]-4-hydroxypiperidine-1-carboxylate as a viscous semisolid, which was converted to tert-butyl 4-[(4-bromo-5-cyano-2-propyl-2H-pyrazol-3-yl)methyl]-4-fluoropiperidine-1-carboxylate according to the methods of Parts H and I of Example 7.

Part B

Hydrochloric acid (3.9 mL of 6 M) was added to a solution of tert-butyl 4-[(4-bromo-5-cyano-2-propyl-2H-pyrazol-3-yl)methyl]-4-fluoropiperidine-1-carboxylate (3.34 g, 7.78 mmol) in ethanol (40 mL), and the reaction was heated at 70° C. for 1.5 hours, allowed to cool to room temperature, and concentrated under reduced pressure to provide 2.9 g of 4-bromo-5-[(4-fluoropiperidin-4-yl)methyl]-1-propyl-1H-pyrazole-3-carbonitrile hydrochloride. The salt was suspended in dichloromethane (40 mL), and triethylamine (4.9 mL, 4.5 eq.) was added. The mixture was stirred for ten minutes to provide a 0.2 M solution of 4-bromo-5-[(4-fluoropiperidin-4-yl)methyl]-1-propyl-1H-pyrazole-3-carbonitrile.

Part C

A portion of the solution from Part B (24 mL) was cooled to 0° C. Methanesulfonyl chloride (0.42 mL, 1.3 eq.) was added dropwise, and the resulting solution was stirred for 1 hour, diluted with dichloromethane (150 mL), and allowed to warm to room temperature. The solution was washed with saturated aqueous sodium bicarbonate (100 mL), dried over magnesium sulfate, filtered, and concentrated under reduced pressure to provide a white foam. The foam was purified by automated flash chromatography (eluting with a gradient of 0-15% CMA in chloroform) to provide 1.5 g of 4-bromo-5-{[4-fluoro-1-(methylsulfonyl)piperidin-4-yl]methyl}-1-propyl-1H-pyrazole-3-carbonitrile as a white foam. The foam was concentrated from 1,2-dimethoxyethane (40 mL) before it was used in Part D.

Part D

The reaction conditions and purification methods described in Part J of Example 7 were used to treat the material from Part C. 1-{[4-Fluoro-1-(methylsulfonyl)piperidin-4-yl]methyl}-2-propyl-2H-pyrazolo[3,4-c]quinolin-4-amine (0.32 g) was obtained as a white powder, mp 268-270° C., dec. $^1$H NMR (300 MHz, DMSO-$d_6$): δ 8.16 (d, J=7.9 Hz, 1H), 7.48 (dd, J=1.2, 8.1 Hz, 1H), 7.32 (m, 1H), 7.17 (m, 1H), 6.64 (br s, 2H), 4.36 (t, J=7.2 Hz, 2H), 3.76 (d, J=22.3 Hz, 2H), 3.46 (m, 2H), 2.85 (s, 3H), 2.80 (m, 2H), 1.80 (m, 6H), 0.90 (t J=7.5 Hz, 3H); MS (ESI) m/z 420 (M+H)$^+$; Anal. calcd for $C_{20}H_{26}FN_5O_2S$: C, 57.26; H, 6.25; N, 16.69. Found: C, 57.03; H, 6.33; N, 16.71.

Example 27

4-[(4-Amino-2-propyl-2H-pyrazolo[3,4-c]quinolin-1-yl)methyl]-4-fluoro-N-isopropylpiperidine-1-carboxamide

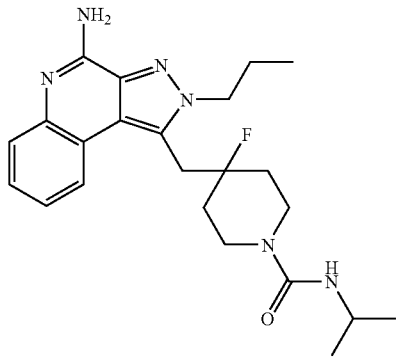

Part A

Isopropyl isocyanate (0.46 mL, 1.3 eq.) was added dropwise to a portion of the solution from Part B of Example 26 (21 mL) at room temperature. The resulting solution was stirred for 1 hour, diluted with dichloromethane (100 mL), washed with water (70 mL), dried over magnesium sulfate, filtered, and concentrated under reduced pressure to provide 1.48 g of a tan foam. The foam was purified by automated flash chromatography (eluting with a gradient of 0-10% CMA in chloroform over 8 column volumes) to provide 1.05 g of 4-(4-bromo-5-cyano-2-propyl-2H-pyrazol-3-ylmethyl)-4-fluoro-N-isopropylpiperidine-1-carboxamide as a white foam.

Part B

The reaction conditions and purification methods described in Part J of Example 7 were used to treat the material from Part A. 4-[(4-Amino-2-propyl-2H-pyrazolo[3,4-c]quinolin-1-yl)methyl]-4-fluoro-N-isopropylpiperidine-1-carboxamide (105 mg) was obtained as a white powder, mp 227-229° C., dec. $^1$H NMR (300 MHz, DMSO-$d_6$): δ 8.13 (d, J=7.6 Hz, 1H), 7.47 (dd, J=1.1, 8.1 Hz, 1H), 7.31 (m, 1H), 7.16 (m, 1H), 6.63 (br s, 2H), 6.17 (d, J=7.6 Hz, 1H), 4.36 (t, J=7.6 Hz, 2H), 3.68-3.89 (m, 5H), 2.72 (t, J=11.9 Hz, 2H), 1.62-1.98 (m, 6H), 1.03 (d, J=6.6 Hz, 6H), 0.09 (t, J=7.6 Hz, 3H); MS (ESI) m/z 427 (M+H)$^+$; Anal. calcd for $C_{23}H_{31}FN_6O$: C, 64.77; H, 7.33; N, 19.70. Found: C, 64.67; H, 7.23; N, 19.65.

Exemplary Compounds

Certain exemplary compounds, including some of those described above in the Examples, have the following Formulas (III-1, IV-1, V-1, or VIII-1) and the following $R_2$, Z, $R_1$, and m substituents or variables, wherein each line of the table is matched with Formula III-1, IV-1, V-1, or VIII-1 to represent a specific embodiment of the invention.

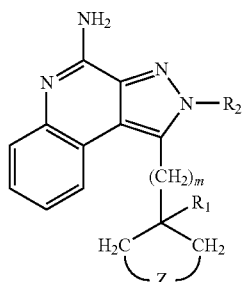

III-1

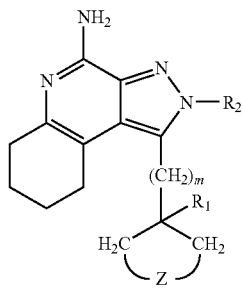

IV-1

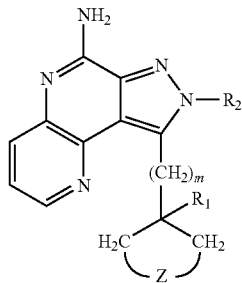

V-1

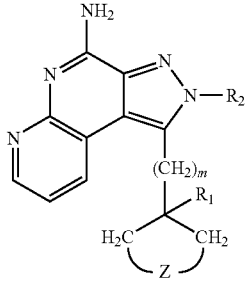

VIII-1

| R₂ | Z | R₁ | m |
|---|---|---|---|
| methyl | Bond | —OH | 1 |
| methyl | Bond | —OH | 2 |
| methyl | Bond | —OCH₃ | 1 |
| methyl | Bond | —OCH₃ | 2 |
| methyl | Bond | —F | 1 |
| methyl | Bond | —F | 2 |
| methyl | —CH₂— | —OH | 1 |
| methyl | —CH₂— | —OH | 2 |
| methyl | —CH₂— | —OCH₃ | 1 |
| methyl | —CH₂— | —OCH₃ | 2 |
| methyl | —CH₂— | —F | 1 |
| methyl | —CH₂— | —F | 2 |
| methyl | —CH₂CH₂— | —OH | 1 |
| methyl | —CH₂CH₂— | —OH | 2 |
| methyl | —CH₂CH₂— | —OCH₃ | 1 |
| methyl | —CH₂CH₂— | —OCH₃ | 2 |
| methyl | —CH₂CH₂— | —F | 1 |
| methyl | —CH₂CH₂— | —F | 2 |
| methyl | —CH₂CH₂CH₂— | —OH | 1 |
| methyl | —CH₂CH₂CH₂— | —OH | 2 |
| methyl | —CH₂CH₂CH₂— | —OCH₃ | 1 |
| methyl | —CH₂CH₂CH₂— | —OCH₃ | 2 |
| methyl | —CH₂CH₂CH₂— | —F | 1 |
| methyl | —CH₂CH₂CH₂— | —F | 2 |
| methyl | —CH₂—O—CH₂— | —OH | 1 |
| methyl | —CH₂—O—CH₂— | —OH | 2 |
| methyl | —CH₂—O—CH₂— | —OCH₃ | 1 |
| methyl | —CH₂—O—CH₂— | —OCH₃ | 2 |
| methyl | —CH₂—O—CH₂— | —F | 1 |
| methyl | —CH₂—O—CH₂— | —F | 2 |
| ethyl | Bond | —OH | 1 |
| ethyl | Bond | —OH | 2 |
| ethyl | Bond | —OCH₃ | 1 |
| ethyl | Bond | —OCH₃ | 2 |
| ethyl | Bond | —F | 1 |
| ethyl | Bond | —F | 2 |
| ethyl | —CH₂— | —OH | 1 |
| ethyl | —CH₂— | —OH | 2 |
| ethyl | —CH₂— | —OCH₃ | 1 |
| ethyl | —CH₂— | —OCH₃ | 2 |
| ethyl | —CH₂— | —F | 1 |
| ethyl | —CH₂— | —F | 2 |
| ethyl | —CH₂CH₂— | —OH | 1 |
| ethyl | —CH₂CH₂— | —OH | 2 |
| ethyl | —CH₂CH₂— | —OCH₃ | 1 |
| ethyl | —CH₂CH₂— | —OCH₃ | 2 |
| ethyl | —CH₂CH₂— | —F | 1 |
| ethyl | —CH₂CH₂— | —F | 2 |
| ethyl | —CH₂CH₂CH₂— | —OH | 1 |
| ethyl | —CH₂CH₂CH₂— | —OH | 2 |
| ethyl | —CH₂CH₂CH₂— | —OCH₃ | 1 |
| ethyl | —CH₂CH₂CH₂— | —OCH₃ | 2 |
| ethyl | —CH₂CH₂CH₂— | —F | 1 |
| ethyl | —CH₂CH₂CH₂— | —F | 2 |
| ethyl | —CH₂—O—CH₂— | —OH | 1 |
| ethyl | —CH₂—O—CH₂— | —OH | 2 |
| ethyl | —CH₂—O—CH₂— | —OCH₃ | 1 |
| ethyl | —CH₂—O—CH₂— | —OCH₃ | 2 |
| ethyl | —CH₂—O—CH₂— | —F | 1 |
| ethyl | —CH₂—O—CH₂— | —F | 2 |
| n-propyl | Bond | —OH | 1 |
| n-propyl | Bond | —OH | 2 |
| n-propyl | Bond | —OCH₃ | 1 |
| n-propyl | Bond | —OCH₃ | 2 |
| n-propyl | Bond | —F | 1 |
| n-propyl | Bond | —F | 2 |
| n-propyl | —CH₂— | —OH | 1 |
| n-propyl | —CH₂— | —OH | 2 |
| n-propyl | —CH₂— | —OCH₃ | 1 |
| n-propyl | —CH₂— | —OCH₃ | 2 |
| n-propyl | —CH₂— | —F | 1 |
| n-propyl | —CH₂— | —F | 2 |
| n-propyl | —CH₂CH₂— | —OH | 1 |
| n-propyl | —CH₂CH₂— | —OH | 2 |
| n-propyl | —CH₂CH₂— | —OCH₃ | 1 |
| n-propyl | —CH₂CH₂— | —OCH₃ | 2 |
| n-propyl | —CH₂CH₂— | —F | 1 |
| n-propyl | —CH₂CH₂— | —F | 2 |
| n-propyl | —CH₂CH₂CH₂— | —OH | 1 |
| n-propyl | —CH₂CH₂CH₂— | —OH | 2 |
| n-propyl | —CH₂CH₂CH₂— | —OCH₃ | 1 |
| n-propyl | —CH₂CH₂CH₂— | —OCH₃ | 2 |
| n-propyl | —CH₂CH₂CH₂— | —F | 1 |
| n-propyl | —CH₂CH₂CH₂— | —F | 2 |
| n-propyl | —CH₂—O—CH₂— | —OH | 1 |
| n-propyl | —CH₂—O—CH₂— | —OH | 2 |
| n-propyl | —CH₂—O—CH₂— | —OCH₃ | 1 |
| n-propyl | —CH₂—O—CH₂— | —OCH₃ | 2 |
| yn-propyl | —CH₂—O—CH₂— | —F | 1 |
| n-propyl | —CH₂—O—CH₂— | —F | 2 |
| n-butyl | Bond | —OH | 1 |
| n-butyl | Bond | —OH | 2 |
| n-butyl | Bond | —OCH₃ | 1 |
| n-butyl | Bond | —OCH₃ | 2 |
| n-butyl | Bond | —F | 1 |
| n-bulyl | Bond | —F | 2 |
| n-butyl | —CH₂— | —OH | 1 |
| n-butyl | —CH₂— | —OH | 2 |
| n-butyl | —CH₂— | —OCH₃ | 1 |
| n-butyl | —CH₂— | —OCH₃ | 2 |
| n-butyl | —CH₂— | —F | 1 |
| n-butyl | —CH₂— | —F | 2 |
| n-butyl | —CH₂CH₂— | —OH | 1 |
| n-butyl | —CH₂CH₂— | —OH | 2 |
| n-butyl | —CH₂CH₂— | —OCH₃ | 1 |
| n-butyl | —CH₂CH₂— | —OCH₃ | 2 |
| n-butyl | —CH₂CH₂— | —F | 1 |
| n-butyl | —CH₂CH₂— | —F | 2 |
| n-butyl | —CH₂CH₂CH₂— | —OH | 1 |
| n-butyl | —CH₂CH₂CH₂— | —OH | 2 |
| n-butyl | —CH₂CH₂CH₂— | —OCH₃ | 1 |
| n-butyl | —CH₂CH₂CH₂— | —OCH₃ | 2 |
| n-butyl | —CH₂CH₂CH₂— | —F | 1 |
| n-butyl | —CH₂CH₂CH₂— | —F | 2 |
| n-butyl | —CH₂—O—CH₂— | —OH | 1 |
| n-butyl | —CH₂—O—CH₂— | —OH | 2 |
| n-butyl | —CH₂—O—CH₂— | —OCH₃ | 1 |
| n-butyl | —CH₂—O—CH₂— | —OCH₃ | 2 |
| n-butyl | —CH₂—O—CH₂— | —F | 1 |
| n-butyl | —CH₂—O—CH₂— | —F | 2 |
| 2-hydroxyethyl | Bond | —OH | 1 |
| 2-hydroxyethyl | Bond | —OH | 2 |
| 2-hydroxyethyl | Bond | —OCH₃ | 1 |
| 2-hydroxyethyl | Bond | —OCH₃ | 2 |
| 2-hydroxyethyl | Bond | —F | 1 |
| 2-hydroxyethyl | Bond | —F | 2 |
| 2-hydroxyethyl | —CH₂— | —OH | 1 |
| 2-hydroxyethyl | —CH₂— | —OH | 2 |
| 2-hydroxyethyl | —CH₂— | —OCH₃ | 1 |
| 2-hydroxyethyl | —CH₂— | —OCH₃ | 2 |
| 2-hydroxyethyl | —CH₂— | —F | 1 |
| 2-hydroxyethyl | —CH₂— | —F | 2 |
| 2-hydroxyethyl | —CH₂CH₂— | —OH | 1 |
| 2-hydroxyethyl | —CH₂CH₂— | —OH | 2 |
| 2-hydroxyethyl | —CH₂CH₂— | —OCH₃ | 1 |
| 2-hydroxyethyl | —CH₂CH₂— | —OCH₃ | 2 |
| 2-hydroxyethyl | —CH₂CH₂— | —F | 1 |
| 2-hydroxyethyl | —CH₂CH₂— | —F | 2 |
| 2-hydroxyethyl | —CH₂CH₂CH₂— | —OH | 1 |
| 2-hydroxyethyl | —CH₂CH₂CH₂— | —OH | 2 |
| 2-hydroxyethyl | —CH₂CH₂CH₂— | —OCH₃ | 1 |
| 2-hydroxyethyl | —CH₂CH₂CH₂— | —OCH₃ | 2 |
| 2-hydroxyethyl | —CH₂CH₂CH₂— | —F | 1 |
| 2-hydroxyethyl | —CH₂CH₂CH₂— | —F | 2 |
| 2-hydroxyethyl | —CH₂—O—CH₂— | —OH | 1 |
| 2-hydroxyethyl | —CH₂—O—CH₂— | —OH | 2 |
| 2-hydroxyethyl | —CH₂—O—CH₂— | —OCH₃ | 1 |
| 2-hydroxyethyl | —CH₂—O—CH₂— | —OCH₃ | 2 |
| 2-hydroxyethyl | —CH₂—O—CH₂— | —F | 1 |
| 2-hydroxyethyl | —CH₂—O—CH₂— | —F | 2 |
| 2-methoxyethyl | Bond | —OH | 1 |
| 2-methoxyethyl | Bond | —OH | 2 |
| 2-methoxyethyl | Bond | —OCH₃ | 1 |
| 2-methoxyethyl | Bond | —OCH₃ | 2 |
| 2-methoxyethyl | Bond | —F | 1 |
| 2-methoxyethyl | Bond | —F | 2 |
| 2-methoxyethyl | —CH₂— | —OH | 1 |

| | | | |
|---|---|---|---|
| 2-methoxyethyl | —CH₂— | —OH | 2 |
| 2-methoxyethyl | —CH₂— | —OCH₃ | 1 |
| 2-methoxyethyl | —CH₂— | —OCH₃ | 2 |
| 2-methoxyethyl | —CH₂— | —F | 1 |
| 2-methoxyethyl | —CH₂— | —F | 2 |
| 2-methoxyethyl | —CH₂CH₂— | —OH | 1 |
| 2-methoxyethyl | —CH₂CH₂— | —OH | 2 |
| 2-methoxyethyl | —CH₂CH₂— | —OCH₃ | 1 |
| 2-methoxyethyl | —CH₂CH₂— | —OCH₃ | 2 |
| 2-methoxyethyl | —CH₂CH₂— | —F | 1 |
| 2-methoxyethyl | —CH₂CH₂— | —F | 2 |
| 2-methoxyethyl | —CH₂CH₂CH₂— | —OH | 1 |
| 2-methoxyethyl | —CH₂CH₂CH₂— | —OH | 2 |
| 2-methoxyethyl | —CH₂CH₂CH₂— | —OCH₃ | 1 |
| 2-methoxyethyl | —CH₂CH₂CH₂— | —OCH₃ | 2 |
| 2-methoxyethyl | —CH₂CH₂CH₂— | —F | 1 |
| 2-methoxyethyl | —CH₂CH₂CH₂— | —F | 2 |
| 2-methoxyethyl | —CH₂—O—CH₂— | —OH | 1 |
| 2-methoxyethyl | —CH₂—O—CH₂— | —OH | 2 |
| 2-methoxyethyl | —CH₂—O—CH₂— | —OCH₃ | 1 |
| 2-methoxyethyl | —CH₂—O—CH₂— | —OCH₃ | 2 |
| 2-methoxyethyl | —CH₂—O—CH₂— | —F | 1 |
| 2-methoxyethyl | —CH₂—O—CH₂— | —F | 2 |

Certain exemplary compounds, including some of those described above in the Examples, have the following Formulas (III-2, IV-2, V-2, and VIII-2) wherein $R_2$, Q, $R_4$, $R_1$, and m are defined immediately below in the table. Each row of the table is matched with Formula III-2, IV-2, V-2, or VIII-2 to represent a specific embodiment of the invention.

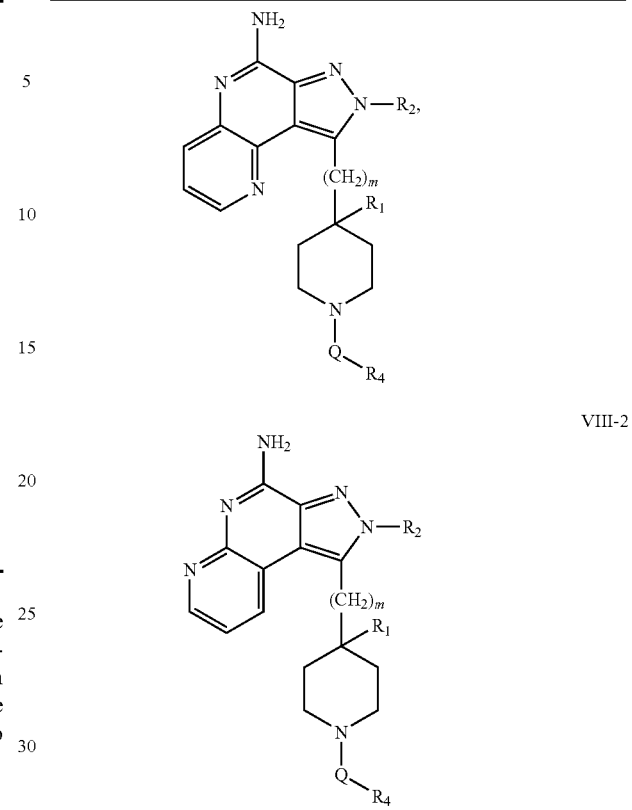

| $R_2$ | Q | $R_4$ | $R_1$ | m |
|---|---|---|---|---|
| methyl | Bond | methyl | —OH | 1 |
| methyl | Bond | methyl | —OH | 2 |
| methyl | Bond | methyl | —OCH₃ | 1 |
| methyl | Bond | methyl | —OCH₃ | 2 |
| methyl | Bond | ethyl | —OH | 1 |
| methyl | Bond | ethyl | —OH | 2 |
| methyl | Bond | ethyl | —OCH₃ | 1 |
| methyl | Bond | ethyl | —OCH₃ | 2 |
| methyl | Bond | isopropyl | —OH | 1 |
| methyl | Bond | isopropyl | —OH | 2 |
| methyl | Bond | isopropyl | —OCH₃ | 1 |
| methyl | Bond | isopropyl | —OCH₃ | 2 |
| methyl | Bond | phenyl | —OH | 1 |
| methyl | Bond | phenyl | —OH | 2 |
| methyl | Bond | phenyl | —OCH₃ | 1 |
| methyl | Bond | phenyl | —OCH₃ | 2 |
| methyl | —C(O)— | methyl | —OH | 1 |
| methyl | —C(O)— | methyl | —OH | 2 |
| methyl | —C(O)— | methyl | —OCH₃ | 1 |
| methyl | —C(O)— | methyl | —OCH₃ | 2 |
| methyl | —C(O)— | ethyl | —OH | 1 |
| methyl | —C(O)— | ethyl | —OH | 2 |
| methyl | —C(O)— | ethyl | —OCH₃ | 1 |
| methyl | —C(O)— | ethyl | —OCH₃ | 2 |
| methyl | —C(O)— | isopropyl | —OH | 1 |
| methyl | —C(O)— | isopropyl | —OH | 2 |
| methyl | —C(O)— | isopropyl | —OCH₃ | 1 |
| methyl | —C(O)— | isopropyl | —OCH₃ | 2 |
| methyl | —C(O)— | phenyl | —OH | 1 |
| methyl | —C(O)— | phenyl | —OH | 2 |
| methyl | —C(O)— | phenyl | —OCH₃ | 1 |
| methyl | —C(O)— | phenyl | —OCH₃ | 2 |
| methyl | —S(O)₂— | methyl | —OH | 1 |
| methyl | —S(O)₂— | methyl | —OH | 2 |
| methyl | —S(O)₂— | methyl | —OCH₃ | 1 |
| methyl | —S(O)₂— | methyl | —OCH₃ | 2 |
| methyl | —S(O)₂— | ethyl | —OH | 1 |
| methyl | —S(O)₂— | ethyl | —OH | 2 |
| methyl | —S(O)₂— | ethyl | —OCH₃ | 1 |

| | | | | |
|---|---|---|---|---|
| methyl | —S(O)₂— | ethyl | —OCH₃ | 2 |
| methyl | —S(O)₂— | isopropyl | —OH | 1 |
| methyl | —S(O)₂— | isopropyl | —OH | 2 |
| methyl | —S(O)₂— | isopropyl | —OCH₃ | 1 |
| methyl | —S(O)₂— | isopropyl | —OCH₃ | 2 |
| methyl | —S(O)₂— | phenyl | —OH | 1 |
| methyl | —S(O)₂— | phenyl | —OH | 2 |
| methyl | —S(O)₂— | phenyl | —OCH₃ | 1 |
| methyl | —S(O)₂— | phenyl | —OCH₃ | 2 |
| methyl | —C(O)—NH— | methyl | —OH | 1 |
| methyl | —C(O)—NH— | methyl | —OH | 2 |
| methyl | —C(O)—NH— | methyl | —OCH₃ | 1 |
| methyl | —C(O)—NH— | methyl | —OCH₃ | 2 |
| methyl | —C(O)—NH— | ethyl | —OH | 1 |
| methyl | —C(O)—NH— | ethyl | —OH | 2 |
| methyl | —C(O)—NH— | ethyl | —OCH₃ | 1 |
| methyl | —C(O)—NH— | ethyl | —OCH₃ | 2 |
| methyl | —C(O)—NH— | isopropyl | —OH | 1 |
| methyl | —C(O)—NH— | isopropyl | —OH | 2 |
| methyl | —C(O)—NH— | isopropyl | —OCH₃ | 1 |
| methyl | —C(O)—NH— | isopropyl | —OCH₃ | 2 |
| methyl | —C(O)—NH— | phenyl | —OH | 1 |
| methyl | —C(O)—NH— | phenyl | —OH | 2 |
| methyl | —C(O)—NH— | phenyl | —OCH₃ | 1 |
| methyl | —C(O)—NH— | phenyl | —OCH₃ | 2 |
| ethyl | Bond | methyl | —OH | 1 |
| ethyl | Bond | methyl | —OH | 2 |
| ethyl | Bond | methyl | —OCH₃ | 1 |
| ethyl | Bond | methyl | —OCH₃ | 2 |
| ethyl | Bond | ethyl | —OH | 1 |
| ethyl | Bond | ethyl | —OH | 2 |
| ethyl | Bond | ethyl | —OCH₃ | 1 |
| ethyl | Bond | ethyl | —OCH₃ | 2 |
| ethyl | Bond | isopropyl | —OH | 1 |
| ethyl | Bond | isopropyl | —OH | 2 |
| ethyl | Bond | isopropyl | —OCH₃ | 1 |
| ethyl | Bond | isopropyl | —OCH₃ | 2 |
| ethyl | Bond | phenyl | —OH | 1 |
| ethyl | Bond | phenyl | —OH | 2 |
| ethyl | Bond | phenyl | —OCH₃ | 1 |
| ethyl | Bond | phenyl | —OCH₃ | 2 |
| ethyl | —C(O)— | methyl | —OH | 1 |
| ethyl | —C(O)— | methyl | —OH | 2 |
| ethyl | —C(O)— | methyl | —OCH₃ | 1 |
| ethyl | —C(O)— | methyl | —OCH₃ | 2 |
| ethyl | —C(O)— | ethyl | —OH | 1 |
| ethyl | —C(O)— | ethyl | —OH | 2 |
| ethyl | —C(O)— | ethyl | —OCH₃ | 1 |
| ethyl | —C(O)— | ethyl | —OCH₃ | 2 |
| ethyl | —C(O)— | isopropyl | —OH | 1 |
| ethyl | —C(O)— | isopropyl | —OH | 2 |
| ethyl | —C(O)— | isopropyl | —OCH₃ | 1 |
| ethyl | —C(O)— | isopropyl | —OCH₃ | 2 |
| ethyl | —C(O)— | phenyl | —OH | 1 |
| ethyl | —C(O)— | phenyl | —OH | 2 |
| ethyl | —C(O)— | phenyl | —OCH₃ | 1 |
| ethyl | —C(O)— | phenyl | —OCH₃ | 2 |
| ethyl | —S(O)₂— | methyl | —OH | 1 |
| ethyl | —S(O)₂— | methyl | —OH | 2 |
| ethyl | —S(O)₂— | methyl | —OCH₃ | 1 |
| ethyl | —S(O)₂— | methyl | —OCH₃ | 2 |
| ethyl | —S(O)₂— | ethyl | —OH | 1 |
| ethyl | —S(O)₂— | ethyl | —OH | 2 |
| ethyl | —S(O)₂— | ethyl | —OCH₃ | 1 |
| ethyl | —S(O)₂— | ethyl | —OCH₃ | 2 |
| ethyl | —S(O)₂— | isopropyl | —OH | 1 |
| ethyl | —S(O)₂— | isopropyl | —OH | 2 |
| ethyl | —S(O)₂— | isopropyl | —OCH₃ | 1 |
| ethyl | —S(O)₂— | isopropyl | —OCH₃ | 2 |
| ethyl | —S(O)₂— | phenyl | —OH | 1 |
| ethyl | —S(O)₂— | phenyl | —OH | 2 |
| ethyl | —S(O)₂— | phenyl | —OCH₃ | 1 |
| ethyl | —S(O)₂— | phenyl | —OCH₃ | 2 |
| ethyl | —C(O)—NH— | methyl | —OH | 1 |
| ethyl | —C(O)—NH— | methyl | —OH | 2 |
| ethyl | —C(O)—NH— | methyl | —OCH₃ | 1 |
| ethyl | —C(O)—NH— | methyl | —OCH₃ | 2 |
| ethyl | —C(O)—NH— | ethyl | —OH | 1 |
| ethyl | —C(O)—NH— | ethyl | —OH | 2 |
| ethyl | —C(O)—NH— | ethyl | —OCH₃ | 1 |
| ethyl | —C(O)—NH— | ethyl | —OCH₃ | 2 |
| ethyl | —C(O)—NH— | isopropyl | —OH | 1 |
| ethyl | —C(O)—NH— | isopropyl | —OH | 2 |
| ethyl | —C(O)—NH— | isopropyl | —OCH₃ | 1 |
| ethyl | —C(O)—NH— | isopropyl | —OCH₃ | 2 |
| ethyl | —C(O)—NH— | phenyl | —OH | 1 |
| ethyl | —C(O)—NH— | phenyl | —OH | 2 |
| ethyl | —C(O)—NH— | phenyl | —OCH₃ | 1 |
| ethyl | —C(O)—NH— | phenyl | —OCH₃ | 2 |
| n-propyl | Bond | methyl | —OH | 1 |
| n-propyl | Bond | methyl | —OH | 2 |
| n-propyl | Bond | methyl | —OCH₃ | 1 |
| n-propyl | Bond | methyl | —OCH₃ | 2 |
| n-propyl | Bond | ethyl | —OH | 1 |
| n-propyl | Bond | ethyl | —OH | 2 |
| n-propyl | Bond | ethyl | —OCH₃ | 1 |
| n-propyl | Bond | ethyl | —OCH₃ | 2 |
| n-propyl | Bond | isopropyl | —OH | 1 |
| n-propyl | Bond | isopropyl | —OH | 2 |
| n-propyl | Bond | isopropyl | —OCH₃ | 1 |
| n-propyl | Bond | isopropyl | —OCH₃ | 2 |
| n-propyl | Bond | phenyl | —OH | 1 |
| n-propyl | Bond | phenyl | —OH | 2 |
| n-propyl | Bond | phenyl | —OCH₃ | 1 |
| n-propyl | Bond | phenyl | —OCH₃ | 2 |
| n-propyl | —C(O)— | methyl | —OH | 1 |
| n-propyl | —C(O)— | methyl | —OH | 2 |
| n-propyl | —C(O)— | methyl | —OCH₃ | 1 |
| n-propyl | —C(O)— | methyl | —OCH₃ | 2 |
| n-propyl | —C(O)— | ethyl | —OH | 1 |
| n-propyl | —C(O)— | ethyl | —OH | 2 |
| n-propyl | —C(O)— | ethyl | —OCH₃ | 1 |
| n-propyl | —C(O)— | ethyl | —OCH₃ | 2 |
| n-propyl | —C(O)— | isopropyl | —OH | 1 |
| n-propyl | —C(O)— | isopropyl | —OH | 2 |
| n-propyl | —C(O)— | isopropyl | —OCH₃ | 1 |
| n-propyl | —C(O)— | isopropyl | —OCH₃ | 2 |
| n-propyl | —C(O)— | phenyl | —OH | 1 |
| n-propyl | —C(O)— | phenyl | —OH | 2 |
| n-propyl | —C(O)— | phenyl | —OCH₃ | 1 |
| n-propyl | —C(O)— | phenyl | —OCH₃ | 2 |
| n-propyl | —S(O)₂— | methyl | —OH | 1 |
| n-propyl | —S(O)₂— | methyl | —OH | 2 |
| n-propyl | —S(O)₂— | methyl | —OCH₃ | 1 |
| n-propyl | —S(O)₂— | methyl | —OCH₃ | 2 |
| n-propyl | —S(O)₂— | ethyl | —OH | 1 |
| n-propyl | —S(O)₂— | ethyl | —OH | 2 |
| n-propyl | —S(O)₂— | ethyl | —OCH₃ | 1 |
| n-propyl | —S(O)₂— | ethyl | —OCH₃ | 2 |
| n-propyl | —S(O)₂— | isopropyl | —OH | 1 |
| n-propyl | —S(O)₂— | isopropyl | —OH | 2 |
| n-propyl | —S(O)₂— | isopropyl | —OCH₃ | 1 |
| n-propyl | —S(O)₂— | isopropyl | —OCH₃ | 2 |
| n-propyl | —S(O)₂— | phenyl | —OH | 1 |
| n-propyl | —S(O)₂— | phenyl | —OH | 2 |
| n-propyl | —S(O)₂— | phenyl | —OCH₃ | 1 |
| n-propyl | —S(O)₂— | phenyl | —OCH₃ | 2 |
| n-propyl | —C(O)—NH— | methyl | —OH | 1 |
| n-propyl | —C(O)—NH— | methyl | —OH | 2 |
| n-propyl | —C(O)—NH— | methyl | —OCH₃ | 1 |
| n-propyl | —C(O)—NH— | methyl | —OCH₃ | 2 |
| n-propyl | —C(O)—NH— | ethyl | —OH | 1 |
| n-propyl | —C(O)—NH— | ethyl | —OH | 2 |
| n-propyl | —C(O)—NH— | ethyl | —OCH₃ | 1 |
| n-propyl | —C(O)—NH— | ethyl | —OCH₃ | 2 |
| n-propyl | —C(O)—NH— | isopropyl | —OH | 1 |
| n-propyl | —C(O)—NH— | isopropyl | —OH | 2 |
| n-propyl | —C(O)—NH— | isopropyl | —OCH₃ | 1 |
| n-propyl | —C(O)—NH— | isopropyl | —OCH₃ | 2 |
| n-propyl | —C(O)—NH— | phenyl | —OH | 1 |
| n-propyl | —C(O)—NH— | phenyl | —OH | 2 |
| n-propyl | —C(O)—NH— | phenyl | —OCH₃ | 1 |
| n-propyl | —C(O)—NH— | phenyl | —OCH₃ | 2 |
| n-butyl | Bond | methyl | —OH | 1 |
| n-butyl | Bond | methyl | —OH | 2 |
| n-butyl | Bond | methyl | —OCH₃ | 1 |
| n-butyl | Bond | methyl | —OCH₃ | 2 |
| n-butyl | Bond | ethyl | —OH | 1 |
| n-butyl | Bond | ethyl | —OH | 2 |
| n-butyl | Bond | ethyl | —OH | 3 |

| | | | | |
|---|---|---|---|---|
| n-butyl | Bond | ethyl | —OCH₃ | 1 |
| n-butyl | Bond | ethyl | —OCH₃ | 2 |
| n-butyl | Bond | isopropyl | —OH | 1 |
| n-butyl | Bond | isopropyl | —OH | 2 |
| n-butyl | Bond | isopropyl | —OCH₃ | 1 |
| n-butyl | Bond | isopropyl | —OCH₃ | 2 |
| n-butyl | Bond | phenyl | —OH | 1 |
| n-butyl | Bond | phenyl | —OH | 2 |
| n-butyl | Bond | phenyl | —OCH₃ | 1 |
| n-butyl | Bond | phenyl | —OCH₃ | 2 |
| n-butyl | —C(O)— | methyl | —OH | 1 |
| n-butyl | —C(O)— | methyl | —OH | 2 |
| n-butyl | —C(O)— | methyl | —OCH₃ | 1 |
| n-butyl | —C(O)— | methyl | —OCH₃ | 2 |
| n-butyl | —C(O)— | ethyl | —OH | 1 |
| n-butyl | —C(O)— | ethyl | —OH | 2 |
| n-butyl | —C(O)— | ethyl | —OCH₃ | 1 |
| n-butyl | —C(O)— | ethyl | —OCH₃ | 2 |
| n-butyl | —C(O)— | isopropyl | —OH | 1 |
| n-butyl | —C(O)— | isopropyl | —OH | 2 |
| n-butyl | —C(O)— | isopropyl | —OCH₃ | 1 |
| n-butyl | —C(O)— | isopropyl | —OCH₃ | 2 |
| n-butyl | —C(O)— | phenyl | —OH | 1 |
| n-butyl | —C(O)— | phenyl | —OH | 2 |
| n-butyl | —C(O)— | phenyl | —OCH₃ | 1 |
| n-butyl | —C(O)— | phenyl | —OCH₃ | 2 |
| n-butyl | —S(O)₂— | methyl | —OH | 1 |
| n-butyl | —S(O)₂— | methyl | —OH | 2 |
| n-butyl | —S(O)₂— | methyl | —OCH₃ | 1 |
| n-butyl | —S(O)₂— | methyl | —OCH₃ | 2 |
| n-butyl | —S(O)₂— | ethyl | —OH | 1 |
| n-butyl | —S(O)₂— | ethyl | —OH | 2 |
| n-butyl | —S(O)₂— | ethyl | —OCH₃ | 1 |
| n-butyl | —S(O)₂— | ethyl | —OCH₃ | 2 |
| n-butyl | —S(O)₂— | isopropyl | —OH | 1 |
| n-butyl | —S(O)₂— | isopropyl | —OH | 2 |
| n-butyl | —S(O)₂— | isopropyl | —OCH₃ | 1 |
| n-butyl | —S(O)₂— | isopropyl | —OCH₃ | 2 |
| n-butyl | —S(O)₂— | phenyl | —OH | 1 |
| n-butyl | —S(O)₂— | phenyl | —OH | 2 |
| n-butyl | —S(O)₂— | phenyl | —OCH₃ | 1 |
| n-butyl | —S(O)₂— | phenyl | —OCH₃ | 2 |
| n-butyl | —C(O)—NH— | methyl | —OH | 1 |
| n-butyl | —C(O)—NH— | methyl | —OH | 2 |
| n-butyl | —C(O)—NH— | methyl | —OCH₃ | 1 |
| n-butyl | —C(O)—NH— | methyl | —OCH₃ | 2 |
| n-butyl | —C(O)—NH— | ethyl | —OH | 1 |
| n-butyl | —C(O)—NH— | ethyl | —OH | 2 |
| n-butyl | —C(O)—NH— | ethyl | —OCH₃ | 1 |
| n-butyl | —C(O)—NH— | ethyl | —OCH₃ | 2 |
| n-butyl | —C(O)—NH— | isopropyl | —OH | 1 |
| n-butyl | —C(O)—NH— | isopropyl | —OH | 2 |
| n-butyl | —C(O)—NH— | isopropyl | —OCH₃ | 1 |
| n-butyl | —C(O)—NH— | isopropyl | —OCH₃ | 2 |
| n-butyl | —C(O)—NH— | phenyl | —OH | 1 |
| n-butyl | —C(O)—NH— | phenyl | —OH | 2 |
| n-butyl | —C(O)—NH— | phenyl | —OCH₃ | 1 |
| n-butyl | —C(O)—NH— | phenyl | —OCH₃ | 2 |
| 2-hydroxyethyl | Bond | methyl | —OH | 1 |
| 2-hydroxyethyl | Bond | methyl | —OH | 2 |
| 2-hydroxyethyl | Bond | methyl | —OCH₃ | 1 |
| 2-hydroxyethyl | Bond | methyl | —OCH₃ | 2 |
| 2-hydroxyethyl | Bond | ethyl | —OH | 1 |
| 2-hydroxyethyl | Bond | ethyl | —OH | 2 |
| 2-hydroxyethyl | Bond | ethyl | —OCH₃ | 1 |
| 2-hydroxyethyl | Bond | ethyl | —OCH₃ | 2 |
| 2-hydroxyethyl | Bond | isopropyl | —OH | 1 |
| 2-hydroxyethyl | Bond | isopropyl | —OH | 2 |
| 2-hydroxyethyl | Bond | isopropyl | —OCH₃ | 1 |
| 2-hydroxyethyl | Bond | isopropyl | —OCH₃ | 2 |
| 2-hydroxyethyl | Bond | phenyl | —OH | 1 |
| 2-hydroxyethyl | Bond | phenyl | —OH | 2 |
| 2-hydroxyethyl | Bond | phenyl | —OCH₃ | 1 |
| 2-hydroxyethyl | Bond | phenyl | —OCH₃ | 2 |
| 2-hydroxyethyl | —C(O)— | methyl | —OH | 1 |
| 2-hydroxyethyl | —C(O)— | methyl | —OH | 2 |
| 2-hydroxyethyl | —C(O)— | methyl | —OCH₃ | 1 |
| 2-hydroxyethyl | —C(O)— | methyl | —OCH₃ | 2 |
| 2-hydroxyethyl | —C(O)— | ethyl | —OH | 1 |
| 2-hydroxyethyl | —C(O)— | ethyl | —OH | 2 |
| 2-hydroxyethyl | —C(O)— | ethyl | —OCH₃ | 1 |
| 2-hydroxyethyl | —C(O)— | ethyl | —OCH₃ | 2 |
| 2-hydroxyethyl | —C(O)— | isopropyl | —OH | 1 |
| 2-hydroxyethyl | —C(O)— | isopropyl | —OH | 2 |
| 2-hydroxyethyl | —C(O)— | isopropyl | —OCH₃ | 1 |
| 2-hydroxyethyl | —C(O)— | isopropyl | —OCH₃ | 2 |
| 2-hydroxyethyl | —C(O)— | phenyl | —OH | 1 |
| 2-hydroxyethyl | —C(O)— | phenyl | —OH | 2 |
| 2-hydroxyethyl | —C(O)— | phenyl | —OCH₃ | 1 |
| 2-hydroxyethyl | —C(O)— | phenyl | —OCH₃ | 2 |
| 2-hydroxyethyl | —S(O)₂— | methyl | —OH | 1 |
| 2-hydroxyethyl | —S(O)₂— | methyl | —OH | 2 |
| 2-hydroxyethyl | —S(O)₂— | methyl | —OCH₃ | 1 |
| 2-hydroxyethyl | —S(O)₂— | methyl | —OCH₃ | 2 |
| 2-hydroxyethyl | —S(O)₂— | ethyl | —OH | 1 |
| 2-hydroxyethyl | —S(O)₂— | ethyl | —OH | 2 |
| 2-hydroxyethyl | —S(O)₂— | ethyl | —OCH₃ | 1 |
| 2-hydroxyethyl | —S(O)₂— | ethyl | —OCH₃ | 2 |
| 2-hydroxyethyl | —S(O)₂— | isopropyl | —OH | 1 |
| 2-hydroxyethyl | —S(O)₂— | isopropyl | —OH | 2 |
| 2-hydroxyethyl | —S(O)₂— | isopropyl | —OCH₃ | 1 |
| 2-hydroxyethyl | —S(O)₂— | isopropyl | —OCH₃ | 2 |
| 2-hydroxyethyl | —S(O)₂— | phenyl | —OH | 1 |
| 2-hydroxyethyl | —S(O)₂— | phenyl | —OH | 2 |
| 2-hydroxyethyl | —S(O)₂— | phenyl | —OCH₃ | 1 |
| 2-hydroxyethyl | —S(O)₂— | phenyl | —OCH₃ | 2 |
| 2-hydroxyethyl | —C(O)—NH— | methyl | —OH | 1 |
| 2-hydroxyethyl | —C(O)—NH— | methyl | —OH | 2 |
| 2-hydroxyethyl | —C(O)—NH— | methyl | —OCH₃ | 1 |
| 2-hydroxyethyl | —C(O)—NH— | methyl | —OCH₃ | 2 |
| 2-hydroxyethyl | —C(O)—NH— | ethyl | —OH | 1 |
| 2-hydroxyethyl | —C(O)—NH— | ethyl | —OH | 2 |
| 2-hydroxyethyl | —C(O)—NH— | ethyl | —OCH₃ | 1 |
| 2-hydroxyethyl | —C(O)—NH— | ethyl | —OCH₃ | 2 |
| 2-hydroxyethyl | —C(O)—NH— | isopropyl | —OH | 1 |
| 2-hydroxyethyl | —C(O)—NH— | isopropyl | —OH | 2 |
| 2-hydroxyethyl | —C(O)—NH— | isopropyl | —OCH₃ | 1 |
| 2-hydroxyethyl | —C(O)—NH— | isopropyl | —OCH₃ | 2 |
| 2-hydroxyethyl | —C(O)—NH— | phenyl | —OH | 1 |
| 2-hydroxyethyl | —C(O)—NH— | phenyl | —OH | 2 |
| 2-hydroxyethyl | —C(O)—NH— | phenyl | —OCH₃ | 1 |
| 2-hydroxyethyl | —C(O)—NH— | phenyl | —OCH₃ | 2 |
| 2-methoxyethyl | Bond | methyl | —OH | 1 |
| 2-methoxyethyl | Bond | methyl | —OH | 2 |
| 2-methoxyethyl | Bond | methyl | —OCH₃ | 1 |
| 2-methoxyethyl | Bond | methyl | —OCH₃ | 2 |
| 2-methoxyethyl | Bond | ethyl | —OH | 1 |
| 2-methoxyethyl | Bond | ethyl | —OH | 2 |
| 2-methoxyethyl | Bond | ethyl | —OCH₃ | 1 |
| 2-methoxyethyl | Bond | ethyl | —OCH₃ | 2 |
| 2-methoxyethyl | Bond | isopropyl | —OH | 1 |
| 2-methoxyethyl | Bond | isopropyl | —OH | 2 |
| 2-methoxyethyl | Bond | isopropyl | —OCH₃ | 1 |
| 2-methoxyethyl | Bond | isopropyl | —OCH₃ | 2 |
| 2-methoxyethyl | Bond | phenyl | —OH | 1 |
| 2-methoxyethyl | Bond | phenyl | —OH | 2 |
| 2-methoxyethyl | Bond | phenyl | —OCH₃ | 1 |
| 2-methoxyethyl | Bond | phenyl | —OCH₃ | 2 |
| 2-methoxyethyl | —C(O)— | methyl | —OH | 1 |
| 2-methoxyethyl | —C(O)— | methyl | —OH | 2 |
| 2-methoxyethyl | —C(O)— | methyl | —OCH₃ | 1 |
| 2-methoxyethyl | —C(O)— | methyl | —OCH₃ | 2 |
| 2-methoxyethyl | —C(O)— | ethyl | —OH | 1 |
| 2-methoxyethyl | —C(O)— | ethyl | —OH | 2 |
| 2-methoxyethyl | —C(O)— | ethyl | —OCH₃ | 1 |
| 2-methoxyethyl | —C(O)— | ethyl | —OCH₃ | 2 |
| 2-methoxyethyl | —C(O)— | isopropyl | —OH | 1 |
| 2-methoxyethyl | —C(O)— | isopropyl | —OH | 2 |
| 2-methoxyethyl | —C(O)— | isopropyl | —OCH₃ | 1 |
| 2-methoxyethyl | —C(O)— | isopropyl | —OCH₃ | 2 |
| 2-methoxyethyl | —C(O)— | phenyl | —OH | 1 |
| 2-methoxyethyl | —C(O)— | phenyl | —OH | 2 |
| 2-methoxyethyl | —C(O)— | phenyl | —OCH₃ | 1 |
| 2-methoxyethyl | —C(O)— | phenyl | —OCH₃ | 2 |
| 2-methoxyethyl | —S(O)₂— | methyl | —OH | 1 |
| 2-methoxyethyl | —S(O)₂— | methyl | —OH | 2 |
| 2-methoxyethyl | —S(O)₂— | methyl | —OCH₃ | 1 |
| 2-methoxyethyl | —S(O)₂— | methyl | —OCH₃ | 2 |
| 2-methoxyethyl | —S(O)₂— | ethyl | —OH | 1 |
| 2-methoxyethyl | —S(O)₂— | ethyl | —OH | 2 |

| | | | | |
|---|---|---|---|---|
| 2-methoxyethyl | —S(O)$_2$— | ethyl | —OCH$_3$ | 1 |
| 2-methoxyethyl | —S(O)$_2$— | ethyl | —OCH$_3$ | 2 |
| 2-methoxyethyl | —S(O)$_2$— | isopropyl | —OH | 1 |
| 2-methoxyethyl | —S(O)$_2$— | isopropyl | —OH | 2 |
| 2-methoxyethyl | —S(O)$_2$— | isopropyl | —OCH$_3$ | 1 |
| 2-methoxyethyl | —S(O)$_2$— | isopropyl | —OCH$_3$ | 2 |
| 2-methoxyethyl | —S(O)$_2$— | phenyl | —OH | 1 |
| 2-methoxyethyl | —S(O)$_2$— | phenyl | —OH | 2 |
| 2-methoxyethyl | —S(O)$_2$— | phenyl | —OCH$_3$ | 1 |
| 2-methoxyethyl | —S(O)$_2$— | phenyl | —OCH$_3$ | 2 |
| 2-methoxyethyl | —C(O)—NH— | methyl | —OH | 1 |
| 2-methoxyethyl | —C(O)—NH— | methyl | —OH | 2 |
| 2-methoxyethyl | —C(O)—NH— | methyl | —OCH$_3$ | 1 |
| 2-methoxyethyl | —C(O)—NH— | methyl | —OCH$_3$ | 2 |
| 2-methoxyethyl | —C(O)—NH— | ethyl | —OH | 1 |
| 2-methoxyethyl | —C(O)—NH— | ethyl | —OH | 2 |
| 2-methoxyethyl | —C(O)—NH— | ethyl | —OCH$_3$ | 1 |
| 2-methoxyethyl | —C(O)—NH— | ethyl | —OCH$_3$ | 2 |
| 2-methoxyethyl | —C(O)—NH— | isopropyl | —OH | 1 |
| 2-methoxyethyl | —C(O)—NH— | isopropyl | —OH | 2 |
| 2-methoxyethyl | —C(O)—NH— | isopropyl | —OCH$_3$ | 1 |
| 2-methoxyethyl | —C(O)—NH— | isopropyl | —OCH$_3$ | 2 |
| 2-methoxyethyl | —C(O)—NH— | phenyl | —OH | 1 |
| 2-methoxyethyl | —C(O)—NH— | phenyl | —OH | 2 |
| 2-methoxyethyl | —C(O)—NH— | phenyl | —OCH$_3$ | 1 |
| 2-methoxyethyl | —C(O)—NH— | phenyl | —OCH$_3$ | 2 |

Certain exemplary compounds, including some of those described above in the Examples, have the following Formulas (III-3, IV-3, V-3, and VIII-3) wherein R$_2$, Q, Z, R$_4$, and m are defined immediately below in the table. Each row of the table is matched with Formula III-3, IV-3, V-3, or VIII-3 to represent a specific embodiment of the invention.

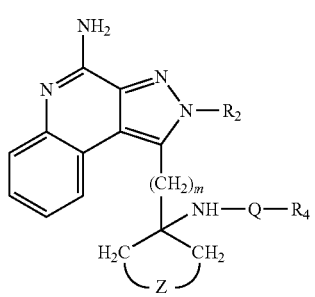

III-3

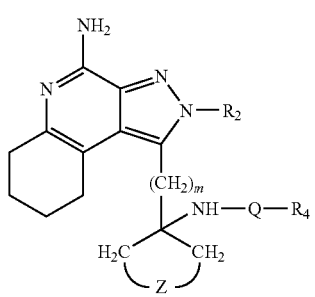

IV-3

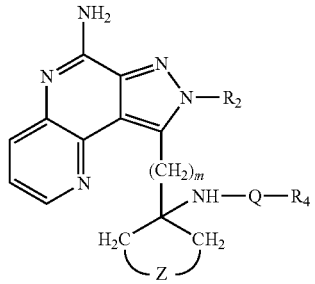

V-3

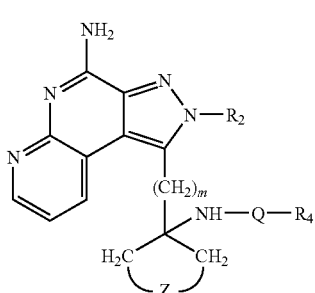

VIII-3

| R$_3$ | Q | Z | R$_4$ | m |
|---|---|---|---|---|
| methyl | Bond | —CH$_2$— | methyl | 1 |
| methyl | Bond | —CH$_2$— | methyl | 2 |
| methyl | Bond | —CH$_2$— | ethyl | 1 |
| methyl | Bond | —CH$_2$— | ethyl | 2 |
| methyl | Bond | —CH$_2$CH$_2$CH$_2$— | methyl | 1 |
| methyl | Bond | —CH$_2$CH$_2$CH$_2$— | methyl | 2 |
| methyl | Bond | —CH$_2$CH$_2$CH$_2$— | ethyl | 1 |
| methyl | Bond | —CH$_2$CH$_2$CH$_2$— | ethyl | 2 |
| methyl | Bond | —CH$_2$—O—CH$_2$— | methyl | 1 |
| methyl | Bond | —CH$_2$—O—CH$_2$— | methyl | 2 |
| methyl | Bond | —CH$_2$—O—CH$_2$— | ethyl | 1 |
| methyl | Bond | —CH$_2$—O—CH$_2$— | ethyl | 2 |
| methyl | —C(O)— | —CH$_2$— | methyl | 1 |
| methyl | —C(O)— | —CH$_2$— | methyl | 2 |
| methyl | —C(O)— | —CH$_2$— | ethyl | 1 |
| methyl | —C(O)— | —CH$_2$— | ethyl | 2 |
| methyl | —C(O)— | —CH$_2$CH$_2$CH$_2$— | methyl | 1 |
| methyl | —C(O)— | —CH$_2$CH$_2$CH$_2$— | methyl | 2 |
| methyl | —C(O)— | —CH$_2$CH$_2$CH$_2$— | ethyl | 1 |
| methyl | —C(O)— | —CH$_2$CH$_2$CH$_2$— | ethyl | 2 |
| methyl | —C(O)— | —CH$_2$—O—CH$_2$— | methyl | 1 |
| methyl | —C(O)— | —CH$_2$—O—CH$_2$— | methyl | 2 |
| methyl | —C(O)— | —CH$_2$—O—CH$_2$— | ethyl | 1 |
| methyl | —C(O)— | —CH$_2$—O—CH$_2$— | ethyl | 2 |
| methyl | —S(O)$_2$— | —CH$_2$— | methyl | 1 |
| methyl | —S(O)$_2$— | —CH$_2$— | methyl | 2 |
| methyl | —S(O)$_2$— | —CH$_2$— | ethyl | 1 |
| methyl | —S(O)$_2$— | —CH$_2$— | ethyl | 2 |
| methyl | —S(O)$_2$— | —CH$_2$CH$_2$CH$_2$— | methyl | 1 |
| methyl | —S(O)$_2$— | —CH$_2$CH$_2$CH$_2$— | methyl | 2 |
| methyl | —S(O)$_2$— | —CH$_2$CH$_2$CH$_2$— | ethyl | 1 |
| methyl | —S(O)$_2$— | —CH$_2$CH$_2$CH$_2$— | ethyl | 2 |
| methyl | —S(O)$_2$— | —CH$_2$—O—CH$_2$— | methyl | 1 |
| methyl | —S(O)$_2$— | —CH$_2$—O—CH$_2$— | methyl | 2 |
| methyl | —S(O)$_2$— | —CH$_2$—O—CH$_2$— | ethyl | 1 |
| methyl | —S(O)$_2$— | —CH$_2$—O—CH$_2$— | ethyl | 2 |
| methyl | —C(O)—NH— | —CH$_2$— | methyl | 1 |
| methyl | —C(O)—NH— | —CH$_2$— | methyl | 2 |
| methyl | —C(O)—NH— | —CH$_2$— | ethyl | 1 |
| methyl | —C(O)—NH— | —CH$_2$— | ethyl | 2 |
| methyl | —C(O)—NH— | —CH$_2$CH$_2$CH$_2$— | methyl | 1 |
| methyl | —C(O)—NH— | —CH$_2$CH$_2$CH$_2$— | methyl | 2 |
| methyl | —C(O)—NH— | —CH$_2$CH$_2$CH$_2$— | ethyl | 1 |
| methyl | —C(O)—NH— | —CH$_2$CH$_2$CH$_2$— | ethyl | 2 |
| methyl | —C(O)—NH— | —CH$_2$—O—CH$_2$— | methyl | 1 |
| methyl | —C(O)—NH— | —CH$_2$—O—CH$_2$— | methyl | 2 |
| methyl | —C(O)—NH— | —CH$_2$—O—CH$_2$— | ethyl | 1 |
| methyl | —C(O)—NH— | —CH$_2$—O—CH$_2$— | ethyl | 2 |

-continued

| | | | | |
|---|---|---|---|---|
| ethyl | Bond | —CH$_2$— | methyl | 1 |
| ethyl | Bond | —CH$_2$— | methyl | 2 |
| ethyl | Bond | —CH$_2$— | ethyl | 1 |
| ethyl | Bond | —CH$_2$— | ethyl | 2 |
| ethyl | Bond | —CH$_2$CH$_2$CH$_2$— | methyl | 1 |
| ethyl | Bond | —CH$_2$CH$_2$CH$_2$— | methyl | 2 |
| ethyl | Bond | —CH$_2$CH$_2$CH$_2$— | ethyl | 1 |
| ethyl | Bond | —CH$_2$CH$_2$CH$_2$— | ethyl | 2 |
| ethyl | Bond | —CH$_2$—O—CH$_2$— | methyl | 1 |
| ethyl | Bond | —CH$_2$—O—CH$_2$— | methyl | 2 |
| ethyl | Bond | —CH$_2$—O—CH$_2$— | ethyl | 1 |
| ethyl | Bond | —CH$_2$—O—CH$_2$— | ethyl | 2 |
| ethyl | —C(O)— | —CH$_2$— | methyl | 1 |
| ethyl | —C(O)— | —CH$_2$— | methyl | 2 |
| ethyl | —C(O)— | —CH$_2$— | ethyl | 1 |
| ethyl | —C(O)— | —CH$_2$— | ethyl | 2 |
| ethyl | —C(O)— | —CH$_2$CH$_2$CH$_2$— | methyl | 1 |
| ethyl | —C(O)— | —CH$_2$CH$_2$CH$_2$— | methyl | 2 |
| ethyl | —C(O)— | —CH$_2$CH$_2$CH$_2$— | ethyl | 1 |
| ethyl | —C(O)— | —CH$_2$CH$_2$CH$_2$— | ethyl | 2 |
| ethyl | —C(O)— | —CH$_2$—O—CH$_2$— | methyl | 1 |
| ethyl | —C(O)— | —CH$_2$—O—CH$_2$— | methyl | 2 |
| ethyl | —C(O)— | —CH$_2$—O—CH$_2$— | ethyl | 1 |
| ethyl | —C(O)— | —CH$_2$—O—CH$_2$— | ethyl | 2 |
| ethyl | —S(O)$_2$— | —CH$_2$— | methyl | 1 |
| ethyl | —S(O)$_2$— | —CH$_2$— | methyl | 2 |
| ethyl | —S(O)$_2$— | —CH$_2$— | ethyl | 1 |
| ethyl | —S(O)$_2$— | —CH$_2$— | ethyl | 2 |
| ethyl | —S(O)$_2$— | —CH$_2$CH$_2$CH$_2$— | methyl | 1 |
| ethyl | —S(O)$_2$— | —CH$_2$CH$_2$CH$_2$— | methyl | 2 |
| ethyl | —S(O)$_2$— | —CH$_2$CH$_2$CH$_2$— | ethyl | 1 |
| ethyl | —S(O)$_2$— | —CH$_2$CH$_2$CH$_2$— | ethyl | 2 |
| ethyl | —S(O)$_2$— | —CH$_2$—O—CH$_2$— | methyl | 1 |
| ethyl | —S(O)$_2$— | —CH$_2$—O—CH$_2$— | methyl | 2 |
| ethyl | —S(O)$_2$— | —CH$_2$—O—CH$_2$— | ethyl | 1 |
| ethyl | —S(O)$_2$— | —CH$_2$—O—CH$_2$— | ethyl | 2 |
| ethyl | —C(O)—NH— | —CH$_2$— | methyl | 1 |
| ethyl | —C(O)—NH— | —CH$_2$— | methyl | 2 |
| ethyl | —C(O)—NH— | —CH$_2$— | ethyl | 1 |
| ethyl | —C(O)—NH— | —CH$_2$— | ethyl | 2 |
| ethyl | —C(O)—NH— | —CH$_2$CH$_2$CH$_2$— | methyl | 1 |
| ethyl | —C(O)—NH— | —CH$_2$CH$_2$CH$_2$— | methyl | 2 |
| ethyl | —C(O)—NH— | —CH$_2$CH$_2$CH$_2$— | ethyl | 1 |
| ethyl | —C(O)—NH— | —CH$_2$CH$_2$CH$_2$— | ethyl | 2 |
| ethyl | —C(O)—NH— | —CH$_2$—O—CH$_2$— | methyl | 1 |
| ethyl | —C(O)—NH— | —CH$_2$—O—CH$_2$— | methyl | 2 |
| ethyl | —C(O)—NH— | —CH$_2$—O—CH$_2$— | ethyl | 1 |
| ethyl | —C(O)—NH— | —CH$_2$—O—CH$_2$— | ethyl | 2 |
| n-propyl | Bond | —CH$_2$— | methyl | 1 |
| n-propyl | Bond | —CH$_2$— | methyl | 2 |
| n-propyl | Bond | —CH$_2$— | ethyl | 1 |
| n-propyl | Bond | —CH$_2$— | ethyl | 2 |
| n-propyl | Bond | —CH$_2$CH$_2$CH$_2$— | methyl | 1 |
| n-propyl | Bond | —CH$_2$CH$_2$CH$_2$— | methyl | 2 |
| n-propyl | Bond | —CH$_2$CH$_2$CH$_2$— | ethyl | 1 |
| n-propyl | Bond | —CH$_2$CH$_2$CH$_2$— | ethyl | 2 |
| n-propyl | Bond | —CH$_2$—O—CH$_2$— | methyl | 1 |
| n-propyl | Bond | —CH$_2$—O—CH$_2$— | methyl | 2 |
| n-propyl | Bond | —CH$_2$—O—CH$_2$— | ethyl | 1 |
| n-propyl | Bond | —CH$_2$—O—CH$_2$— | ethyl | 2 |
| n-propyl | —C(O)— | —CH$_2$— | methyl | 1 |
| n-propyl | —C(O)— | —CH$_2$— | methyl | 2 |
| n-propyl | —C(O)— | —CH$_2$— | ethyl | 1 |
| n-propyl | —C(O)— | —CH$_2$— | ethyl | 2 |
| n-propyl | —C(O)— | —CH$_2$CH$_2$CH$_2$— | methyl | 1 |
| n-propyl | —C(O)— | —CH$_2$CH$_2$CH$_2$— | methyl | 2 |
| n-propyl | —C(O)— | —CH$_2$CH$_2$CH$_2$— | ethyl | 1 |
| n-propyl | —C(O)— | —CH$_2$CH$_2$CH$_2$— | ethyl | 2 |
| n-propyl | —C(O)— | —CH$_2$—O—CH$_2$— | methyl | 1 |
| n-propyl | —C(O)— | —CH$_2$—O—CH$_2$— | methyl | 2 |
| n-propyl | —C(O)— | —CH$_2$—O—CH$_2$— | ethyl | 1 |
| n-propyl | —C(O)— | —CH$_2$—O—CH$_2$— | ethyl | 2 |
| n-propyl | —S(O)$_2$— | —CH$_2$— | methyl | 1 |
| n-propyl | —S(O)$_2$— | —CH$_2$— | methyl | 2 |
| n-propyl | —S(O)$_2$— | —CH$_2$— | ethyl | 1 |
| n-propyl | —S(O)$_2$— | —CH$_2$— | ethyl | 2 |
| n-propyl | —S(O)$_2$— | —CH$_2$CH$_2$CH$_2$— | methyl | 1 |
| n-propyl | —S(O)$_2$— | —CH$_2$CH$_2$CH$_2$— | methyl | 2 |
| n-propyl | —S(O)$_2$— | —CH$_2$CH$_2$CH$_2$— | ethyl | 1 |
| n-propyl | —S(O)$_2$— | —CH$_2$CH$_2$CH$_2$— | ethyl | 2 |
| n-propyl | —S(O)$_2$— | —CH$_2$—O—CH$_2$— | methyl | 1 |
| n-propyl | —S(O)$_2$— | —CH$_2$—O—CH$_2$— | methyl | 2 |
| n-propyl | —S(O)$_2$— | —CH$_2$—O—CH$_2$— | ethyl | 1 |
| n-propyl | —S(O)$_2$— | —CH$_2$—O—CH$_2$— | ethyl | 2 |
| n-propyl | —C(O)—NH— | —CH$_2$— | methyl | 1 |
| n-propyl | —C(O)—NH— | —CH$_2$— | methyl | 2 |
| n-propyl | —C(O)—NH— | —CH$_2$— | ethyl | 1 |
| n-propyl | —C(O)—NH— | —CH$_2$— | ethyl | 2 |
| n-propyl | —C(O)—NH— | —CH$_2$CH$_2$CH$_2$— | methyl | 1 |
| n-propyl | —C(O)—NH— | —CH$_2$CH$_2$CH$_2$— | methyl | 2 |
| n-propyl | —C(O)—NH— | —CH$_2$CH$_2$CH$_2$— | ethyl | 1 |
| n-propyl | —C(O)—NH— | —CH$_2$CH$_2$CH$_2$— | ethyl | 2 |
| n-propyl | —C(O)—NH— | —CH$_2$—O—CH$_2$— | methyl | 1 |
| n-propyl | —C(O)—NH— | —CH$_2$—O—CH$_2$— | methyl | 2 |
| n-propyl | —C(O)—NH— | —CH$_2$—O—CH$_2$— | ethyl | 1 |
| n-propyl | —C(O)—NH— | —CH$_2$—O—CH$_2$— | ethyl | 2 |
| n-butyl | Bond | —CH$_2$— | methyl | 1 |
| n-butyl | Bond | —CH$_2$— | methyl | 2 |
| n-butyl | Bond | —CH$_2$— | ethyl | 1 |
| n-butyl | Bond | —CH$_2$— | ethyl | 2 |
| n-butyl | Bond | —CH$_2$CH$_2$CH$_2$— | methyl | 1 |
| n-butyl | Bond | —CH$_2$CH$_2$CH$_2$— | methyl | 2 |
| n-butyl | Bond | —CH$_2$CH$_2$CH$_2$— | ethyl | 1 |
| n-butyl | Bond | —CH$_2$CH$_2$CH$_2$— | ethyl | 2 |
| n-butyl | Bond | —CH$_2$—O—CH$_2$— | methyl | 1 |
| n-butyl | Bond | —CH$_2$—O—CH$_2$— | methyl | 2 |
| n-butyl | Bond | —CH$_2$—O—CH$_2$— | ethyl | 1 |
| n-butyl | Bond | —CH$_2$—O—CH$_2$— | ethyl | 2 |
| n-butyl | —C(O)— | —CH$_2$— | methyl | 1 |
| n-butyl | —C(O)— | —CH$_2$— | methyl | 2 |
| n-butyl | —C(O)— | —CH$_2$— | ethyl | 1 |
| n-butyl | —C(O)— | —CH$_2$— | ethyl | 2 |
| n-butyl | —C(O)— | —CH$_2$CH$_2$CH$_2$— | methyl | 1 |
| n-butyl | —C(O)— | —CH$_2$CH$_2$CH$_2$— | methyl | 2 |
| n-butyl | —C(O)— | —CH$_2$CH$_2$CH$_2$— | ethyl | 1 |
| n-butyl | —C(O)— | —CH$_2$CH$_2$CH$_2$— | ethyl | 2 |
| n-butyl | —C(O)— | —CH$_2$—O—CH$_2$— | methyl | 1 |
| n-butyl | —C(O)— | —CH$_2$—O—CH$_2$— | methyl | 2 |
| n-butyl | —C(O)— | —CH$_2$—O—CH$_2$— | ethyl | 1 |
| n-butyl | —C(O)— | —CH$_2$—O—CH$_2$— | ethyl | 2 |
| n-butyl | —S(O)$_2$— | —CH$_2$— | methyl | 1 |
| n-butyl | —S(O)$_2$— | —CH$_2$— | methyl | 2 |
| n-butyl | —S(O)$_2$— | —CH$_2$— | ethyl | 1 |
| n-butyl | —S(O)$_2$— | —CH$_2$— | ethyl | 2 |
| n-butyl | —S(O)$_2$— | —CH$_2$CH$_2$CH$_2$— | methyl | 1 |
| n-butyl | —S(O)$_2$— | —CH$_2$CH$_2$CH$_2$— | methyl | 2 |
| n-butyl | —S(O)$_2$— | —CH$_2$CH$_2$CH$_2$— | ethyl | 1 |
| n-butyl | —S(O)$_2$— | —CH$_2$CH$_2$CH$_2$— | ethyl | 2 |
| n-butyl | —S(O)$_2$— | —CH$_2$—O—CH$_2$— | methyl | 1 |
| n-butyl | —S(O)$_2$— | —CH$_2$—O—CH$_2$— | methyl | 2 |
| n-butyl | —S(O)$_2$— | —CH$_2$—O—CH$_2$— | ethyl | 1 |
| n-butyl | —S(O)$_2$— | —CH$_2$—O—CH$_2$— | ethyl | 2 |
| n-butyl | —C(O)—NH— | —CH$_2$— | methyl | 1 |
| n-butyl | —C(O)—NH— | —CH$_2$— | methyl | 2 |
| n-butyl | —C(O)—NH— | —CH$_2$— | ethyl | 1 |
| n-butyl | —C(O)—NH— | —CH$_2$— | ethyl | 2 |
| n-butyl | —C(O)—NH— | —CH$_2$CH$_2$CH$_2$ | methyl | 1 |
| n-butyl | —C(O)—NH— | —CH$_2$CH$_2$CH$_2$ | methyl | 2 |
| n-butyl | —C(O)—NH— | —CH$_2$CH$_2$CH$_2$ | ethyl | 1 |
| n-butyl | —C(O)—NH— | —CH$_2$CH$_2$CH$_2$ | ethyl | 2 |
| n-butyl | —C(O)—NH— | —CH$_2$—O—CH$_2$— | methyl | 1 |
| n-butyl | —C(O)—NH— | —CH$_2$—O—CH$_2$— | methyl | 2 |
| n-butyl | —C(O)—NH— | —CH$_2$—O—CH$_2$— | ethyl | 1 |
| n-butyl | —C(O)—NH— | —CH$_2$—O—CH$_2$— | ethyl | 2 |
| 2-hydroxyethyl | Bond | —CH$_2$— | methyl | 1 |
| 2-hydroxyethyl | Bond | —CH$_2$— | methyl | 2 |
| 2-hydroxyethyl | Bond | —CH$_2$— | ethyl | 1 |
| 2-hydroxyethyl | Bond | —CH$_2$— | ethyl | 2 |
| 2-hydroxyethyl | Bond | —CH$_2$CH$_2$CH$_2$— | methyl | 1 |
| 2-hydroxyethyl | Bond | —CH$_2$CH$_2$CH$_2$— | methyl | 2 |
| 2-hydroxyethyl | Bond | —CH$_2$CH$_2$CH$_2$— | ethyl | 1 |
| 2-hydroxyethyl | Bond | —CH$_2$CH$_2$CH$_2$— | ethyl | 2 |
| 2-hydroxyethyl | Bond | —CH$_2$—O—CH$_2$— | methyl | 1 |
| 2-hydroxyethyl | Bond | —CH$_2$—O—CH$_2$— | methyl | 2 |
| 2-hydroxyethyl | Bond | —CH$_2$—O—CH$_2$— | ethyl | 1 |
| 2-hydroxyethyl | Bond | —CH$_2$—O—CH$_2$— | ethyl | 2 |
| 2-hydroxyethyl | —C(O)— | —CH$_2$— | methyl | 1 |
| 2-hydroxyethyl | —C(O)— | —CH$_2$— | methyl | 2 |
| 2-hydroxyethyl | —C(O)— | —CH$_2$— | ethyl | 1 |
| 2-hydroxyethyl | —C(O)— | —CH$_2$— | ethyl | 2 |

-continued

| | | | | |
|---|---|---|---|---|
| 2-hydroxyethyl | —C(O)— | —CH₂CH₂CH₂— | methyl | 1 |
| 2-hydroxyethyl | —C(O)— | —CH₂CH₂CH₂— | methyl | 2 |
| 2-hydroxyethyl | —C(O)— | —CH₂CH₂CH₂— | ethyl | 1 |
| 2-hydroxyethyl | —C(O)— | —CH₂CH₂CH₂— | ethyl | 2 |
| 2-hydroxyethyl | —C(O)— | —CH₂—O—CH₂— | methyl | 1 |
| 2-hydroxyethyl | —C(O)— | —CH₂—O—CH₂— | methyl | 2 |
| 2-hydroxyethyl | —C(O)— | —CH₂—O—CH₂— | ethyl | 1 |
| 2-hydroxyethyl | —C(O)— | —CH₂—O—CH₂— | ethyl | 2 |
| 2-hydroxyethyl | —S(O)₂— | —CH₂— | methyl | 1 |
| 2-hydroxyethyl | —S(O)₂— | —CH₂— | methyl | 2 |
| 2-hydroxyethyl | —S(O)₂— | —CH₂— | ethyl | 1 |
| 2-hydroxyethyl | —S(O)₂— | —CH₂— | ethyl | 2 |
| 2-hydroxyethyl | —S(O)₂— | —CH₂CH₂CH₂— | methyl | 1 |
| 2-hydroxyethyl | —S(O)₂— | —CH₂CH₂CH₂— | methyl | 2 |
| 2-hydroxyethyl | —S(O)₂— | —CH₂CH₂CH₂— | ethyl | 1 |
| 2-hydroxyethyl | —S(O)₂— | —CH₂CH₂CH₂— | ethyl | 2 |
| 2-hydroxyethyl | —S(O)₂— | —CH₂—O—CH₂— | methyl | 1 |
| 2-hydroxyethyl | —S(O)₂— | —CH₂—O—CH₂— | methyl | 2 |
| 2-hydroxyethyl | —S(O)₂— | —CH₂—O—CH₂— | ethyl | 1 |
| 2-hydroxyethyl | —S(O)₂— | —CH₂—O—CH₂— | ethyl | 2 |
| 2-hydroxyethyl | —C(O)—NH— | —CH₂— | methyl | 1 |
| 2-hydroxyethyl | —C(O)—NH— | —CH₂— | methyl | 2 |
| 2-hydroxyethyl | —C(O)—NH— | —CH₂— | ethyl | 1 |
| 2-hydroxyethyl | —C(O)—NH— | —CH₂— | ethyl | 2 |
| 2-hydroxyethyl | —C(O)—NH— | —CH₂CH₂CH₂— | methyl | 1 |
| 2-hydroxyethyl | —C(O)—NH— | —CH₂CH₂CH₂— | methyl | 2 |
| 2-hydroxyethyl | —C(O)—NH— | —CH₂CH₂CH₂— | ethyl | 1 |
| 2-hydroxyethyl | —C(O)—NH— | —CH₂CH₂CH₂— | ethyl | 2 |
| 2-hydroxyethyl | —C(O)—NH— | —CH₂—O—CH₂— | methyl | 1 |
| 2-hydroxyethyl | —C(O)—NH— | —CH₂—O—CH₂— | methyl | 2 |
| 2-hydroxyethyl | —C(O)—NH— | —CH₂—O—CH₂— | ethyl | 1 |
| 2-hydroxyethyl | —C(O)—NH— | —CH₂—O—CH₂— | ethyl | 2 |
| 2-methoxyethyl | Bond | —CH₂— | methyl | 1 |
| 2-methoxyethyl | Bond | —CH₂— | methyl | 2 |
| 2-methoxyethyl | Bond | —CH₂— | ethyl | 1 |
| 2-methoxyethyl | Bond | —CH₂— | ethyl | 2 |
| 2-methoxyethyl | Bond | —CH₂CH₂CH₂— | methyl | 1 |
| 2-methoxyethyl | Bond | —CH₂CH₂CH₂— | methyl | 2 |
| 2-methoxyethyl | Bond | —CH₂CH₂CH₂— | ethyl | 1 |
| 2-methoxyethyl | Bond | —CH₂CH₂CH₂— | ethyl | 2 |
| 2-methoxyethyl | Bond | —CH₂—O—CH₂— | methyl | 1 |
| 2-methoxyethyl | Bond | —CH₂—O—CH₂— | methyl | 2 |
| 2-methoxyethyl | Bond | —CH₂—O—CH₂— | ethyl | 1 |
| 2-methoxyethyl | Bond | —CH₂—O—CH₂— | ethyl | 2 |
| 2-methoxyethyl | —C(O)— | —CH₂— | methyl | 1 |
| 2-methoxyethyl | —C(O)— | —CH₂— | methyl | 2 |
| 2-methoxyethyl | —C(O)— | —CH₂— | ethyl | 1 |
| 2-methoxyethyl | —C(O)— | —CH₂— | ethyl | 2 |
| 2-methoxyethyl | —C(O)— | —CH₂CH₂CH₂— | methyl | 1 |
| 2-methoxyethyl | —C(O)— | —CH₂CH₂CH₂— | methyl | 2 |
| 2-methoxyethyl | —C(O)— | —CH₂CH₂CH₂— | ethyl | 1 |
| 2-methoxyethyl | —C(O)— | —CH₂CH₂CH₂— | ethyl | 2 |
| 2-methoxyethyl | —C(O)— | —CH₂—O—CH₂— | methyl | 1 |
| 2-methoxyethyl | —C(O)— | —CH₂—O—CH₂— | methyl | 2 |
| 2-methoxyethyl | —C(O)— | —CH₂—O—CH₂— | ethyl | 1 |
| 2-methoxyethyl | —C(O)— | —CH₂—O—CH₂— | ethyl | 2 |
| 2-methoxyethyl | —S(O)₂— | —CH₂— | methyl | 1 |
| 2-methoxyethyl | —S(O)₂— | —CH₂— | methyl | 2 |
| 2-methoxyethyl | —S(O)₂— | —CH₂— | ethyl | 1 |
| 2-methoxyethyl | —S(O)₂— | —CH₂— | ethyl | 2 |
| 2-methoxyethyl | —S(O)₂— | —CH₂CH₂CH₂— | methyl | 1 |
| 2-methoxyethyl | —S(O)₂— | —CH₂CH₂CH₂— | methyl | 2 |
| 2-methoxyethyl | —S(O)₂— | —CH₂CH₂CH₂— | ethyl | 1 |
| 2-methoxyethyl | —S(O)₂— | —CH₂CH₂CH₂— | ethyl | 2 |
| 2-methoxyethyl | —S(O)₂— | —CH₂—O—CH₂— | methyl | 1 |
| 2-methoxyethyl | —S(O)₂— | —CH₂—O—CH₂— | methyl | 2 |
| 2-methoxyethyl | —S(O)₂— | —CH₂—O—CH₂— | ethyl | 1 |
| 2-methoxyethyl | —S(O)₂— | —CH₂—O—CH₂— | ethyl | 2 |
| 2-methoxyethyl | —C(O)—NH— | —CH₂— | methyl | 1 |
| 2-methoxyethyl | —C(O)—NH— | —CH₂— | methyl | 2 |
| 2-methoxyethyl | —C(O)—NH— | —CH₂— | ethyl | 1 |
| 2-methoxyethyl | —C(O)—NH— | —CH₂— | ethyl | 2 |
| 2-methoxyethyl | —C(O)—NH— | —CH₂CH₂CH₂— | methyl | 1 |
| 2-methoxyethyl | —C(O)—NH— | —CH₂CH₂CH₂— | methyl | 2 |
| 2-methoxyethyl | —C(O)—NH— | —CH₂CH₂CH₂— | ethyl | 1 |
| 2-methoxyethyl | —C(O)—NH— | —CH₂CH₂CH₂— | ethyl | 2 |
| 2-methoxyethyl | —C(O)—NH— | —CH₂—O—CH₂— | methyl | 1 |
| 2-methoxyethyl | —C(O)—NH— | —CH₂—O—CH₂— | methyl | 2 |
| 2-methoxyethyl | —C(O)—NH— | —CH₂—O—CH₂— | ethyl | 1 |
| 2-methoxyethyl | —C(O)—NH— | —CH₂—O—CH₂— | ethyl | 2 |

Certain exemplary compounds, including some of those described above in the Examples, have the following Formulas (III-4, IV-4, V-4, and VIII-4) wherein $R_2$ and m are defined immediately below in the table. Each row of the table is matched with Formula III-4, IV-4, V-4, or VIII-4 to represent a specific embodiment of the invention.

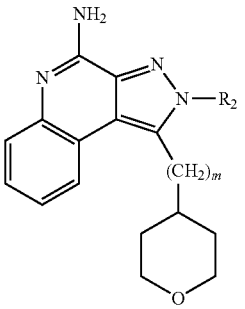

III-4

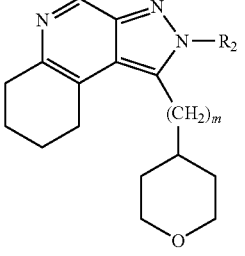

IV-4

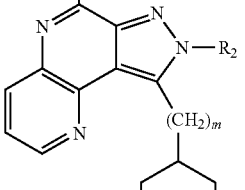

V-4

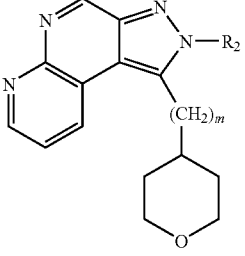

VIII-4

-continued

| $R_2$ | m |
|---|---|
| methyl | 1 |
| methyl | 2 |
| ethyl | 1 |
| ethyl | 2 |
| n-propyl | 1 |
| n-propyl | 2 |
| n-butyl | 1 |
| n-butyl | 2 |
| 2-hydroxyethyl | 1 |
| 2-hydroxyethyl | 2 |
| 2-methoxyethyl | 1 |
| 2-methoxyethyl | 2 |

Compounds of the invention have been found to modulate cytokine biosynthesis by inducing the production of interferon α and/or tumor necrosis factor α in human cells when tested using one of the methods described below.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et al. in "Cytokine Induction by the Immunomodulators Imiquimod and S-27609," *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 hours to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30° C. to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype calorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN to International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin 1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at 4×10⁶ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30 μM-0.014 μM) and the DMSO concentration to 0.4%. The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30° C. to −70° C. until analysis.

Interferon-α and Tumor Necrosis Factor-αAnalysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemiluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above-mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the Formula I:

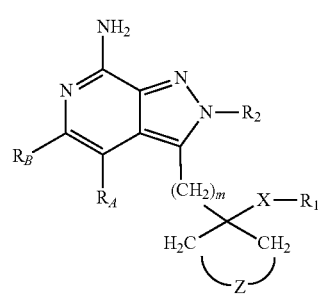

wherein:

Z is selected from the group consisting of:

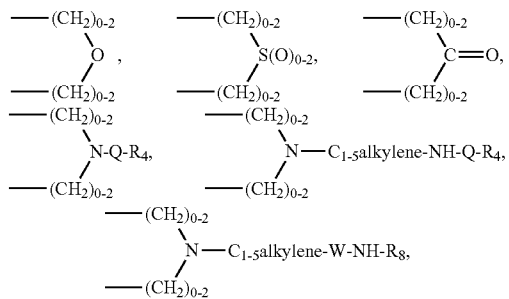

a bond,
$C_{1-5}$alkylene,

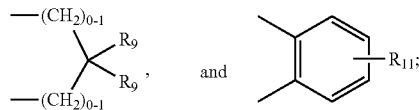

X is selected from the group consisting of a bond, —$C_{2-3}$ alkylene-, and —O—$C_{2-3}$ alkylene-;

$R_1$ is selected from the group consisting of:
hydrogen,
hydroxy,
fluorine,
alkoxy,
—$N(R_9)_2$,
—NH-Q$R_4$,
—$S(O)_{0-2}$-alkyl,
—$S(O)_2$—NH—$R_9$,
—$C(R_6)$—$N(R_8)$—$R_4$,
—O—$C(R_6)$—$N(R_8)$—$R_4$,
—$C(R_6)$—O-alkyl,
—O—$C(R_6)$—$R_4$, and

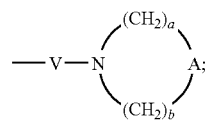

with the proviso that when Z is a bond, $C_{1-5}$ alkylene,

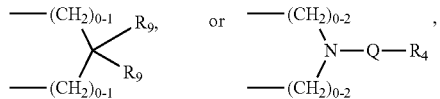

and X is a bond,
then $R_1$ is other than hydrogen;
m is an integer from 1 to 5;
$R_A$ and $R_B$ taken together form a fused benzo ring unsubstituted or substituted by one or more R groups;
R is selected from the group consisting of:
halogen,
hydroxy,
alkyl,
haloalkyl,
alkoxy, and
—$N(R_9)_2$;

$R_2$ is selected from the group consisting of:
hydrogen,
alkyl,
alkoxyalkylenyl,
hydroxyalkylenyl,
haloalkylenyl, and
$R_4$—$C(R_6)$—O—$C_{1-4}$ alkylenyl;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_6$ is selected from the group consisting of =O and =S;

$R_8$ is selected from the group consisting of hydrogen, alkyl, alkoxyalkylenyl, and arylalkylenyl;

$R_9$ is selected from the group consisting of hydrogen and alkyl;

$R_{11}$ is selected from the group consisting of hydrogen, alkyl, halogen, and trifluoromethyl;

A is selected from the group consisting of —O—, —C(O)—, —$S(O)_{0-2}$—, —$CH_2$—, and —$N(R_4)$—;

Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, and —$C(R_6)$—$N(OR_9)$—;

V is selected from the group consisting of —$C(R_6)$—, —O—$C(R_6)$—, —$N(R_8)$—$C(R_6)$—, and —$S(O)_2$—;

W is selected from the group consisting of a bond, —C(O)—, and —$S(O)_2$—; and a and b are independently integers from 1 to 6 with the proviso that a +b is ≦7;

or a pharmaceutically acceptable salt thereof

2. A compound of the Formula III:

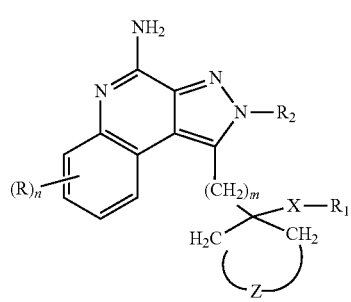

wherein:

Z is selected from the group consisting of:

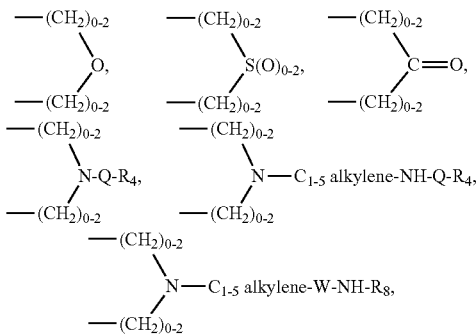

a bond, $C_{1-5}$ alkylene,

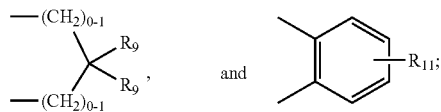

X is selected from the group consisting of a bond, —$C_{2-3}$ alkylene-, and —O—$C_{2-3}$ alkylene-;

$R_1$ is selected from the group consisting of:
hydrogen,
hydroxy,
fluorine,
alkoxy,
—$N(R_9)_2$,
—NH-Q-$R_4$,
—$S(O)_{0-2}$-alkyl,
—$S(O)_2$—NH—$R_9$,
—$C(R_6)$—$N(R_8)$—$R_4$,
—O—$C(R_6)$—$N(R_8)$—$R_4$,
—$C(R_6)$—O-alkyl,
—O—$C(R_6)$—$R_4$, and

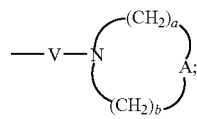

with the proviso that when Z is a bond, $C_{1-5}$ alkylene,

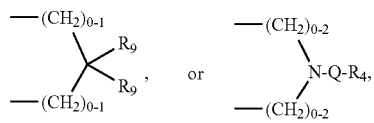

and X is a bond,
then $R_1$ is other than hydrogen;
m is an integer from 1 to 5;
R is selected from the group consisting of:
halogen,
hydroxy,
alkyl,
haloalkyl,
alkoxy, and
—$N(R_9)_2$;

n is an integer from 0 to 4;

$R_2$ is selected from the group consisting of:
hydrogen,
alkyl,
alkoxyalkylenyl,
hydroxyalkylenyl,
haloalkylenyl, and
$R_4$—$C(R_6)$—O—$C_{1-4}$ alkylenyl;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_6$ is selected from the group consisting of =O and =S;

$R_8$ is selected from the group consisting of hydrogen, alkyl, alkoxyalkylenyl, and arylalkylenyl;

$R_9$ is selected from the group consisting of hydrogen and alkyl;

$R_{11}$ is selected from the group consisting of hydrogen, alkyl, halogen, and trifluoromethyl;

A is selected from the group consisting of —O—, —C(O)—, —$S(O)_{0-2}$—, —$CH_2$—, and —$N(R_4)$—;

Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, and —$C(R_6)$—$N(OR_9)$—;

V is selected from the group consisting of —$C(R_6)$—, —O—$C(R_6)$—, —$N(R_8)$—$C(R_6)$—, and —$S(O)_2$—;

W is selected from the group consisting of a bond, —C(O)—, and —$S(O)_2$—; and a and b are independently integers from 1 to 6 with the proviso that a +b is $\leq 7$;

or a pharmaceutically acceptable salt thereof.

3. A compound of the Formula XIV:

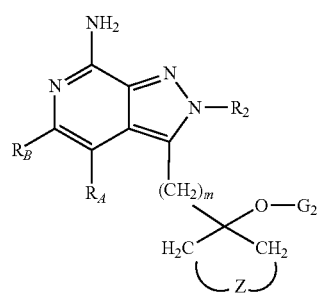

XIV wherein:

Z is selected from the group consisting of:

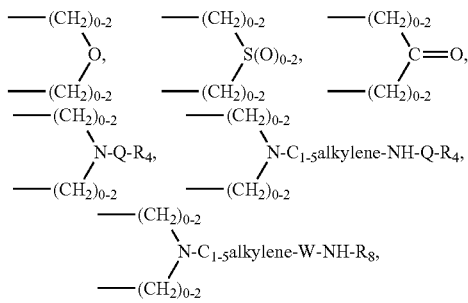

a bond,
$C_{1-5}$alkylene,

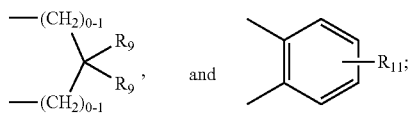

m is an integer from 1 to 5;

$R_A$ and $R_B$ taken together form a fused benzo ring unsubstituted or substituted by one or more R groups:

R is selected from the group consisting of:
halogen,
hydroxy,
alkyl,
haloalkyl,
alkoxy, and
—$N(R_9)_2$;

$R_2$ is selected from the group consisting of:
hydrogen,
alkyl,
alkoxyalkylenyl,
hydroxyalkylenyl,
haloalkylenyl, and
$R_4$—$C(R_6)$—O—$C_{1-4}$ alkylenyl;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, acetylamino, alkylamino, dialkylamino, (dialkylamino)alkyleneoxy, and in the case of alkyl, alkenyl, alkynyl, and heterocyclyl, oxo;

$R_6$ is selected from the group consisting of =O and =S;

$R_8$ is selected from the group consisting of hydrogen, alkyl, alkoxyalkylenyl, and arylalkylenyl;

$R_9$ is selected from the group consisting of hydrogen and alkyl;

$R_{11}$ is selected from the group consisting of hydrogen, alkyl, halogen, and trifluoromethyl;

Q is selected from the group consisting of a bond, —$C(R_6)$—, —$C(R_6)$—$C(R_6)$—, —$S(O)_2$—, —$C(R_6)$—$N(R_8)$—W—, —$S(O)_2$—$N(R_8)$—, —$C(R_6)$—O—, and —$C(R_6)$—$N(OR_9)$—;

W is selected from the group consisting of a bond, —C(O)—, and —$S(O)_2$—;

$G_2$ is selected from the group consisting of:
—$X_2$—C(O)—R',
α-aminoacyl,
α-aminoacyl-α-aminoacyl,
—$X_2$—C(O)—O—R',
—C(O)—N(R")R', and
—$S(O)_2$—R';

$X_2$ is selected from the group consisting of a bond; —$CH_2$—O—; —$CH(CH_3)$—O—; —$C(CH_3)_2$—O—; and, in the case of —$X_2$—C(O)—O—R', —$CH_2$—NH—;

R' and R" are independently selected from the group consisting of $C_{1-10}$ alkyl, $C_{3-7}$ cycloalkyl, phenyl, and benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$, with the proviso that R" can also be hydrogen; and α-aminoacyl is an α-aminoacyl group derived from an amino acid selected from the group consisting of racemic, D-, and L-amino acids;

or a pharmaceutically acceptable salt thereof.

4. The compound or salt of claim 2 wherein R is hydroxy.

5. The compound or salt of claim 2 wherein n is 0.

6. The compound or salt of any one of claims 1, 2, 3, 4, and 5, wherein m is an integer from 1 to 3.

7. The compound or salt of claim 6 wherein m is 1.

8. The compound or salt of any one of claims 1, 2, 3, 4, and 5, wherein Z is selected from the group consisting of a bond and $C_{1-3}$ alkylene.

9. The compound or salt of any one of claims 1, 2, 3, 4, and 5, wherein Z is selected from the group consisting of:

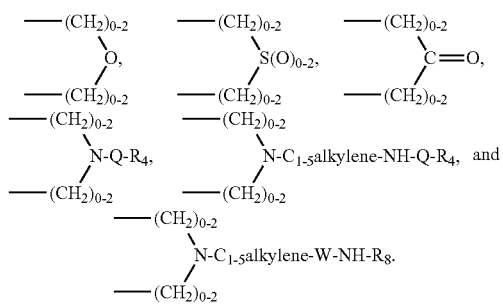

10. The compound or salt of claim 9 wherein Z is

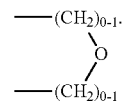

11. The compound or salt of claim 9 wherein Z is

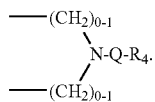

12. The compound or salt of any one of claims 2, 3, 4, and 5, wherein Q is selected from the group consisting of —C(O)—, —C(O)—O—, —S(O)$_2$—, and —C(R$_6$)—N(R$_8$)—.

13. The compound or salt of claim 12 wherein R$_4$ is selected from the group consisting of alkyl, aryl, arylalkylenyl, heteroaryl, and heterocyclyl, wherein the aryl group can be unsubstituted or substituted by one or more substituents independently selected from the group consisting of acetylamino, alkyl, alkoxy, cyano, and halogen.

14. The compound or salt of any one of claims 1, 2, 4, and 5, wherein X is a bond.

15. The compound or salt of any one of claims 1, 2, 4, and 5, wherein R$_1$ is selected from the group consisting of hydroxy and methoxy.

16. The compound or salt of any one of claims 1, 2, 4, and 5, wherein R$_1$ is fluoro.

17. The compound or salt of any one of claims 1, 2, 4, and 5, wherein R$_1$ is selected from the group consisting of —NH$_2$, —NH-Q-R$_4$, —C(O)—NH$_2$, and —C(O)—N(R$_8$)—R$_4$, wherein:

Q is selected from the group consisting of —C(O)—, —S(O)$_2$—, —C(O)—O—, and —C(O)—NH—, R$_8$ is selected from the group consisting of hydrogen and alkyl, and R$_4$ is selected from the group consisting of alkyl and alkoxyalkylenyl.

18. The compound or salt of any one of claims 1, 2, 4, and 5, wherein Z is

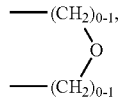

X is a bond, and R$_1$ is hydrogen.

19. The compound or salt of claim 5, wherein Z is

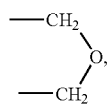

X is a bond, and R$_1$, is hydrogen.

20. The compound or salt of any one of claims 1, 2, 3, 4, and 5, wherein R$_2$ is selected from the group consisting of C$_{1-4}$ alkyl, C$_{1-4}$ alkyl-O—C$_{2-4}$ alkylenyl, and hydroxyC$_{2-4}$ alkylenyl.

21. The compound of salt of claim 20 wherein R$_2$ is selected from the group consisting of methyl, ethyl, n-propyl, n-butyl, 2-methoxyethyl, and 2-hydroxyethyl.

22. A pharmaceutical composition comprising a therapeutically effective amount of a compound or salt of any one of the preceding claims in combination with a pharmaceutically acceptable carrier.

* * * * *